(12) United States Patent
Kletzmayr et al.

(10) Patent No.: US 11,707,470 B2
(45) Date of Patent: Jul. 25, 2023

(54) INOSITOL DERIVATIVES FOR USE IN PATHOLOGICAL CRYSTALLIZATION

(71) Applicants: ETH Zurich, Zurich (CH); UNIVERSITAT BERN, Bern (CH)

(72) Inventors: Anna Kletzmayr, Zürich (CH); Makoto Kuro-o, Zürich (CH); Hirosaka Hayashi, Zürich (CH); Mattias E. Ivarsson, Zürich (CH); Jean-Christophe Leroux, Zürich (CH)

(73) Assignees: ETH Zurich, Zurich (CH); Universitat Bern, Bern (CH)

( * ) Notice: Subject to any disclaimer, the term of this patent is extended or adjusted under 35 U.S.C. 154(b) by 0 days.

(21) Appl. No.: 17/340,163

(22) Filed: Jun. 7, 2021

(65) Prior Publication Data

US 2021/0290643 A1 Sep. 23, 2021

Related U.S. Application Data

(63) Continuation-in-part of application No. 16/852,587, filed on Apr. 20, 2020, now Pat. No. 11,028,112, which is a continuation-in-part of application No. 16/060,980, filed as application No. PCT/EP2016/080657 on Dec. 12, 2016, now Pat. No. 10,624,909.

(30) Foreign Application Priority Data

| Dec. 11, 2015 | (EP) | 15199682 |
| Apr. 7, 2016 | (EP) | 16164299 |
| Jun. 7, 2016 | (EP) | 16173422 |
| Nov. 20, 2020 | (EP) | 20209090 |

(51) Int. Cl.
*A61K 31/6615* (2006.01)
*A61P 13/04* (2006.01)

(52) U.S. Cl.
CPC ......... *A61K 31/6615* (2013.01); *A61P 13/04* (2018.01)

(58) Field of Classification Search
None
See application file for complete search history.

(56) References Cited

U.S. PATENT DOCUMENTS

| 2010/0048730 A1 | 2/2010 | Li et al. |
| 2014/0271915 A1 | 9/2014 | Perello Bestard et al. |

FOREIGN PATENT DOCUMENTS

| EP | 0269105 | 6/1988 |
| EP | 2022501 | 2/2009 |
| EP | 2324835 | 5/2011 |
| WO | 2010018278 | 2/2010 |
| WO | 2010049921 | 5/2010 |
| WO | 2012138963 | 10/2012 |
| WO | 2013045107 | 4/2013 |

OTHER PUBLICATIONS

Grases F Et Al: "Phytate (IP6) Is a Prowerful Agent for Preventing Calcifications in Biological Fluids: Usefulness in Renal Lithiasis Treatment", Anticancer Research—International Journal of Cancer Research and Treatment, International Institute of Anticancer Reasearch, GR, vol. 19, No. 5A, Jan. 1, 1999, pp. 3717-3722.

Neil S. Keddie Et Al: "Development of inositol-based antagonists for the D-myo-inositol 1,4,5-trisphosphate receptor", Chemical Communications—CHEMCOM., vol. 47, No. 1, Jan. 1, 2011, pp. 242-244.

Elisabeth V. Giger Et Al: "siRNA Transfection with Calcium Phosphate Nanoparticles Stabilized with PEGylated Chelators", Advanced Healthcare Materials, vol. 2, No. 1, Jan. 1, 2013, pp. 134-144.

Felix Grases Et Al: "Phytate (Myo-inositol hexakisphosphate) inhibits cardiovascular calcifications in rats", Frontiers in Bioscience, vol. 11, No. 1, Jan. 1, 2006, pp. 136-142.

Mattheolabakis G Et Al: "Pegylation improves the pharmacokinetics and bioavailability of small-molecule drugs hydrolyzable by esterases: A study of phosph-ibuprofen", Journal of Pharmacology and Experimental Therapeutics Oct. 1, 2014 American Society for Pharmacology and Experimental Therapy USA, vol. 351, No. Oct. 1, 2014, pp. 61-66.

Bailon, P. and Won, C. (2009). PEG-modified biopharmaceuticals. Expert Opin. Drug Deliv., 6(1).

Veronese, F. and Pasut, G. (2005). PEGylation, successful approach to drug delivery. Drug Discovery Today, 10(21).

Zhang, X., Wang, H., Ma, Z. and Wu, B. (2014). Effects of pharmaceutical PEGylation on drug metabolism and its clinical concerns. Expert Opinion on Drug Metabolism & Toxicology, 10(12), pp. 1691-1702.

Weinhart, M., Grunwald, I., Wyszogrodzka, M., Gaetjen, L., Hartwig, A. and Haag, R. (2010). Linear Poly(methylglycerol) and Linear Polyglycerol as Potent Protein and Cell Resistant Alternatives to Poly(ethylene glycol). Chemistry, 5, p. 1993.

Florin et al "Polyphosphate-mediated protection from cellular intoxication with Clostridium difficile toxin B" Biochim Biophys Acta. Oct. 12, 1984;805(2):131-6. doi: 10.1016/0167-4889(84)90159-9.

Guttenberg et al "Inositol hexakisphosphate-dependent processing of Clostridium sordellii lethal toxin and Clostridium novyi alpha-toxin" J Biol Chem Apr. 29, 2011;286(17):14779-86. doi: 10.1074/jbc.M110.200691. Epub Mar. 8, 2011.

Veronese et al. "The Impact of PEGylation on Biological Therapies" Biodrugs 22: 315-329 (2008).

Hamidi et al. "Pharmacokinetic Consequences of Pegylation" Drug Delivery 13: 399-409 (2006).

Greenwald et al. "Effective drug delivery by PEGylated drug conjugates" Adv Drug Deliv Rev 55: 217-250, 2003 (abstract).

*Primary Examiner* — Samantha L Shterengarts
(74) *Attorney, Agent, or Firm* — JMB Davis Ben-David

(57) ABSTRACT

The invention is related to an inositol polyphosphate oligo alkyl ether compound, or its pharmaceutically acceptable salt, for use in treatment or prevention of a disease associated with formation of calcium salt crystals.

12 Claims, 34 Drawing Sheets

Fig. 3, (A) (continued)
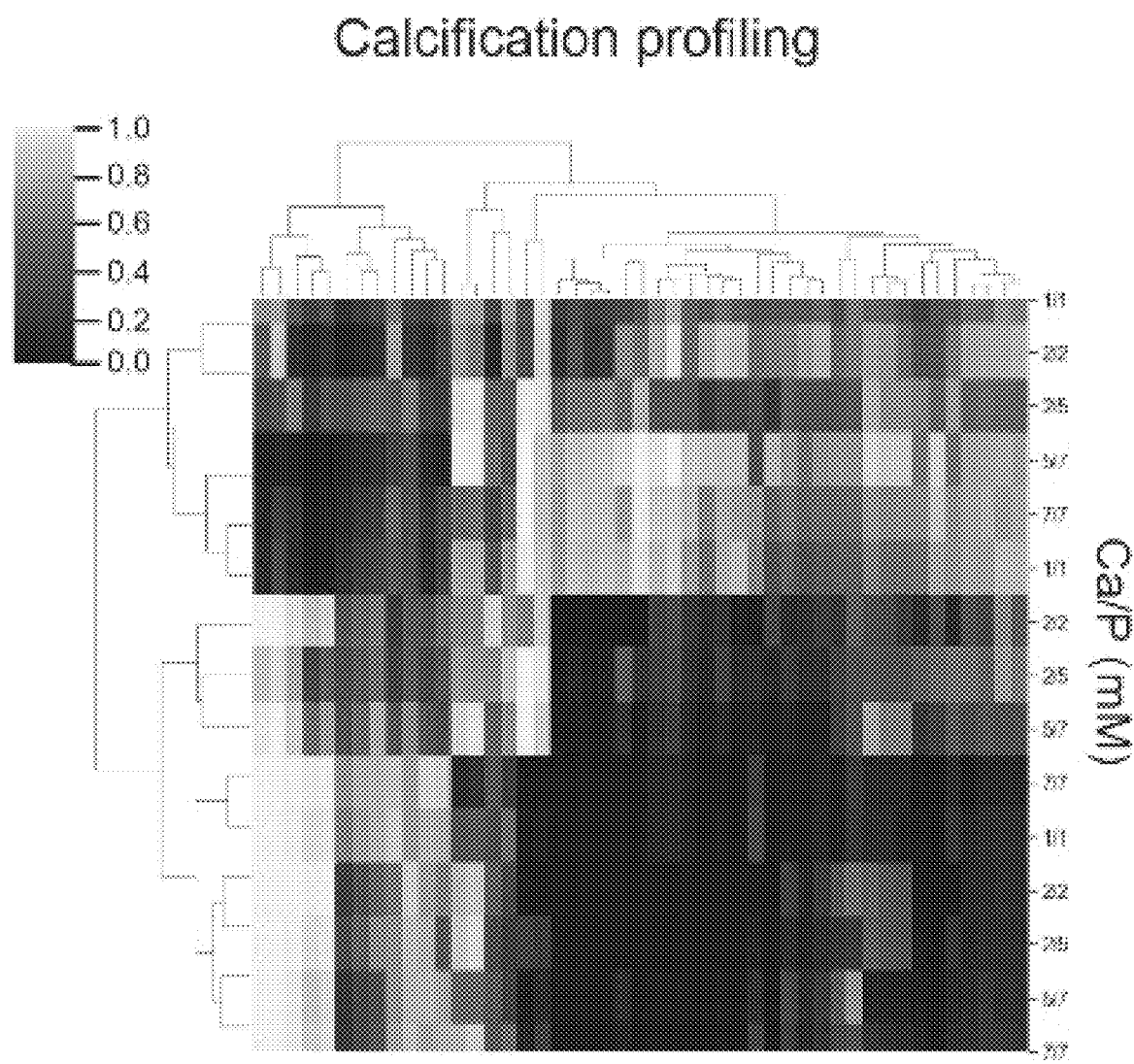

| Compound | Complete inhibition (μM)<br>Area covered with CaP < 10% of ctrl | Inhibition of CaP aggregation (μM)<br>Aggregate size < 50% of ctrl |
|---|---|---|
| IP6 | Promotion of CaP precipitation | - |
| IP5 | | - |
| OEG$_4$-(IP5)$_2$ | | - |
| IS6 | No inhibition | - |
| IC6 | Inhibition<br>> 100 | 100 |
| OEG$_2$-IP5 | 30 | 3 |
| OEG$_{11}$-IP5 | 10 | 0.3 |
| (OEG$_2$)$_2$-IP4 | 30 | 3 |
| (OEG$_{11}$)$_2$-IP4 | 10 | 1 |
| OEG$_8$-(IP5)$_2$ | 30 | 1 |

Fig. 14

| | Urine Phosphate (mg/day) | Serum Phosphate (mg/dL) | Urine Calcium (mg/day) | Serum Calcium (mg/dL) |
|---|---|---|---|---|
| NP + vehicle | 1.87 ± 0.40 | 6.92 ± 1.06 | 0.34 ± 0.27 | 8.6 ± 0.44 |
| NP + (OEG$_2$)$_2$-IP4 | 1.42 ± 0.27 | 8.68 ± 1.15 | 0.38 ± 0.19 | 8.95 ± 0.56 |
| HP + vehicle | 35.58 ± 3.79 | 8.55 ± 1.67 | 0.08 ± 0.01 | 8.08 ± 0.25 |
| HP + (OEG$_2$)$_2$-IP4 | 32.22 ± 6.59 | 9.07 ± 1.71 | 0.11 ± 0.02 | 8.77 ± 0.41 |

INOSITOL DERIVATIVES FOR USE IN PATHOLOGICAL CRYSTALLIZATION

CROSS-REFERENCE TO RELATED APPLICATIONS

This is a Continuation-in-Part of U.S. patent application Ser. No. 16/852,587, filed Apr. 20, 2020, which is a Continuation-in-Part of U.S. patent application Ser. No. 16/060,980, filed Jun. 11, 2018, now issued as U.S. Pat. No. 10,624,909, which is the US National Stage of International Patent Application No. PCT/EP2016/080657, filed Dec. 12, 2016, and which in turn claims priority to European Patent Application Nos. 16173422.3, filed Jun. 7, 2016, 16164299.6, filed Apr. 7, 2016, and 15199682.4, filed Dec. 11, 2015. This application also claims priority to European Patent Application No. 20209090.8, filed Nov. 20, 2020. The contents of the foregoing patent applications are incorporated by reference herein in their entirety.

FIELD

The invention is related to an inositol polyphosphate oligo alkyl ether compound, or its pharmaceutically acceptable salt, for use in treatment or prevention of a disease associated with formation of calcium salt crystals.

BACKGROUND

Patients with chronic kidney disease (CKD) suffer from accelerated mineral deposition in soft tissues, in particular in the vascular system, due to a loss in homeostasis of factors that regulate biomineralization processes in the body. Such deposits lead to stiffening of arterial walls, which ultimately leads to increased blood pressure, left ventricular hypertrophy, reduced coronary blood flow, compromised endothelial function and damage to the microcirculation in the kidneys and brain. As a result, all-cause mortality of CKD patients increases exponentially as renal function decreases.

Physiological calcium and phosphate concentrations in the blood are close to supersaturation. Blood components such as fetuin-A interact with calcium and phosphate to form soluble nanoparticles termed calciprotein particles (CPPs) that prevent precipitation and resultant calcification under normal conditions. So-called primary CPPs are amorphous and have a hydrodynamic radius of typically less than 100 nm and mature with time to reorganize into crystalline secondary CPPs that have a hydrodynamic radius of more than 100 nm. Secondary CPPs are subsequently thought to progress to calcification and to initiate pathological responses.

There is pertinent evidence that vascular calcification is associated with cardiovascular diseases. As shown in the following, there are also reasons to assume that vascular calcification is the primary cause for certain cardiovascular diseases and that treating vascular calcification in the early stages of the disease might lead to an improved condition of the cardiovascular system.

Cho et al. (J Hypertens. 2015 August; 33(8):1633-41.) studies aortic calcification in elderly men with hypertension. The aim of this study is to investigate the relationship between aortic calcification, arterial stiffening, left ventricular hypertrophy, and diastolic dysfunction. Noncontrast computed tomography (CT) is used for the generation of the aorta calcium score (ACS) and brachial-ankle pulse wave velocity (baPWV) is measured to determine systemic arterial stiffness. A clear association between heavy aortic calcification, resultant arterial stiffening and left ventricular hypertrophy or diastolic dysfunction is shown, even after adjusting for various clinical variables. Only the amount of the aortic calcium deposition reflected by the calcium scores showed a significant independent correlation with E' velocity, which is a marker of the function of the left ventricle of the heart. Aortic calcification is speculated to underlie left ventricular hypertrophy and diastolic dysfunction in these patients. Of note, the studied population had no serious chronic kidney disease.

Cheng et al. (Pulse (Basel). 2018 March; 5(1-4):144-153.) reviews the role of vascular calcification in heart failure and cognitive decline. One study (Henry et al. Kidney Int 2002; 62: 1402-1407.) shows that renal function is inversely associated with cardiovascular and all-cause mortality and vascular calcification is the major cause of cardiovascular disease in patients with chronic kidney disease (CKD). The authors state that vascular calcification may also enhance arterial stiffness and render arterial stiffness less reversible. The authors speculate that once arterial stiffness or vascular calcification has developed, it may be less likely to stop the ongoing pathophysiology of heart failure. To quantify the interplay between arteries and heart, an index of ventriculo-arterial coupling has been mathematically modelled. The utilization of this ventriculoarterial coupling index, Ea/Ees, could assist in understanding the impact of vascular calcification on cardiac performance. The authors conclude that earlier intervention targeting vascular calcification may benefit the patients with heart failure. Understanding the pathophysiology consequence of vascular calcification may help to improve the management of patients with atherosclerosis, accelerated arterial stiffness, hypertension, and heart failure with preserved ejection fraction.

Di Iorio et al. (Kidney Blood Press Res. 2011; 34(3):180-7.) conducted a study on coronary artery calcification progression in 132 middle-aged hemodialysis patients. Coronary artery calcification (CAC), 12-lead ECG and pulse wave velocity (PWV) were assessed at baseline and study completion and statistically evaluated. The authors find that vascular calcification is a marker of vasculopathy and appears to be associated with cardiac repolarization and arterial stiffness abnormalities in patients undergoing maintenance dialysis. A significant change in CAC burden was associated with changes in arterial stiffness and cardiac repolarization and CAC progression was associated with a significantly greater increase in PWV and cardiac repolarization at study completion. The authors conclude that CAC progression is associated with a progressive deterioration of parameters of arterial stiffness and cardiac repolarization. Patients experiencing CAC progression were at significantly greater risk of experiencing a simultaneous deterioration of markers of arterial compliance and cardiac repolarization. Taken together, these results suggest that coronary calcifications are associated with stiffness of large central arteries and cardiac repolarization defects.

Dweck et al. (J Am Coll Cardiol. 2012 Nov. 6; 60(19): 1854-63.) reviews the pathophysiology of aortic stenosis with respect to both the valve and the myocardium. In particular, the authors focus on the role of inflammation, fibrosis, and calcification in progressive valve narrowing and then examine the development of left ventricular hypertrophy, its subsequent decompensation, and the transition to heart failure. Aortic stenosis is characterized by progressive aortic valve narrowing and secondary left ventricular hypertrophy. Valve calcification plays a key role in the development of aortic stenosis and can be quantified using computed tomography. The degree of valvular calcification correlates with valve severity, disease progression, and the development of symptoms and adverse events. In one-sixth of patients with sclerosis, the calcification process accelerates, hemodynamic obstruction ensues, and the valve becomes stenotic. This progression is thought to be driven by the differentiation of myofibroblasts into osteoblasts. Calcification is composed of nodules containing hydroxyapatite deposited on a bonelike matrix of collagen, osteopontin, and other bone matrix proteins. Calcification is the critical process in determining the progression of aortic valve stenosis and is therefore likely to be a crucial treatment target. Calcification is believed to be the predominant mechanism by which progressive valve narrowing occurs.

Forsythe et al. (J Am Coll Cardiol. 2018 Feb. 6; 71(5): 513-523.) assessed whether 18F-NaF positron emission tomography (PET) and computed tomography (CT) predicts AAA growth and clinical outcomes in patients with abdominal aortic aneurysm (AAA). Fluorine-18-sodium fluoride (18F-NaF) uptake is a marker of active vascular calcification associated with high-risk atherosclerotic plaque. The positron-emitting radiotracer 18F-sodium fluoride (18F-NaF) can identify areas of early microcalcification. Fluorine-18-NaF uptake was increased in AAA compared with nonaneurysmal regions within the same aorta and aortas of control subjects. Histology and micro-PET-CT demonstrated that 18F-NaF uptake localized to areas of aneurysm disease and active calcification. Patients with aneurysms in the highest tertile of 18F-NaF uptake were more likely to experience AAA repair or rupture during follow-up. This PET-CT study of patients with asymptomatic AAA demonstrates that 18F-NaF uptake identifies advanced aneurysmal disease and is associated with aneurysm growth and clinical AAA events independent of established clinical risk factors.

Guo et al. (Hypertension. 2017 January; 69(1):102-108.) prospectively evaluate association of aortic calcification burden with progression of arterial stiffness in population-based samples of healthy middle-aged men. Aortic calcification was evaluated from level of aortic arch to iliac bifurcation. Arterial stiffness progression was measured as annual change in brachial-ankle pulse wave velocity. Aortic calcification had a positive and significant association with brachial-ankle pulse wave velocity after adjusting for age, race, mean arterial pressure, and heart rate. Annual change in aortic calcification was positively and significantly associated with arterial stiffness progression. In the subgroup of participants with prevalent aortic calcification at baseline, an increase in aortic calcification over the follow-up period was also significantly associated with greater arterial stiffness progression. The findings suggest that aortic calcification may be causally linked to arterial stiffness.

Marwick et al. (Kidney Int. 2019 October; 96(4):836-849.) reviews valvular heart disease in chronic kidney disease. Valvular heart disease (VHD) is highly prevalent in patients with chronic kidney disease (CKD) and end-stage kidney disease. The first detectable stage of VHD involvement in CKD is calcification. Calcification of the interstitial cells of the valve leaflets (and the annulus and subvalvular apparatus of the mitral valve) are the unifying pathophysiological features of valvular stenosis and/or insufficiency secondary to CKD and end-stage kidney disease (ESKD). Among patients undergoing long-term dialysis, the number of calcified valves is associated with all-cause mortality and cardiovascular death. Valvular calcification is an important contributor to VHD among patients with CKD and ESKD, particularly among patients with rapidly progressive aortic stenosis. Delaying the onset of valvular calcification may be a means of delaying the development or progression of VHD.

Mizobuchi et al. (J Am Soc Nephrol. 2009 July; 20(7): 1453-64.) reviews vascular calcification in chronic kidney disease. Cardiovascular complications are the leading cause of death in patients with chronic kidney disease (CKD). A study demonstrated that the extent and histoanatomic type of vascular calcification are predictors of subsequent vascular mortality. Studies in VSMCs showed (Giachelli et al. Circ Res 96: 717-722, 2005; Chen et al., Kidney Int 62: 1724-1731, 2002) that high extracellular phosphate levels induce VSMCs to transform into osteoblast-like cells, suggesting that the processes of vascular calcification are active. The hemodynamic consequences of vascular calcification are the loss of arterial elasticity, increase in pulse wave velocity, development of left ventricular hypertrophy, decrease in coronary artery perfusion, and myocardial ischemia and failure.

Pikilidou et al. (J Vasc Res. 2015; 52(1):32-40.) reviews the contribution of osteoprogenitor cells to arterial stiffness and hypertension. Evidence shows that vascular calcification, either medial or intimal, induces arterial stiffening further worsening hypertension parallel to substantially increasing cardiovascular risk. Osteoprogenitor cells can derive from different cell types such as monocytes, pericytes and vascular smooth muscle cells (VSMCs) outside the bone microenviroment. The ectopic arterial calcium deposition is discriminated into medial and intimal and is predictive of cardiovascular morbidity and mortality. Mounting evidence supports (Altunkan et al., Eur J Intern Med 2005; 16: 580-584.) that arterial calcification largely affects arterial stiffness, a well-known consequence of vascular aging and the most important contributor to the development of hypertension and its detrimental consequences, namely stroke and myocardial infarction. There is a significant reverse association between pulse wave velocity, a reliable surrogate marker of cardiovascular risk, and cross-sectional cortical bone area in women, but not in men, after adjusting for confounders. The authors state that it is known by now that VC is associated with hypertension and that the onset of arterial calcification occurs at an earlier stage in hypertensive subjects. Moreover, it has been demonstrated that coronary artery calcification is associated with an increased occurrence of ischemic stroke in hypertensives. The mechanism behind this observation is that arterial calcification causes a progressive reduction in vascular resilience and compliance with a parallel increase in arterial stiffness, which is a major determinant of the rise in systolic blood pressure, the fall in diastolic BP and the acceleration of pulse wave velocity.

A pharmaceutical agent capable of reducing the propensity for progression of primary CPPs to secondary CPPs, and hence ultimately capable of reducing pathological crystallization, would therefore be of significant therapeutic value. There is, to date, no approved or clinically validated therapy for the reduction or prevention of vascular calcifications.

Thus, the problem underlying the present invention is to provide an efficacious pharmacological intervention for reducing pathological crystallization. This problem is solved by the subject matter of the independent claims.

SUMMARY

The present invention relates to the use of inositol phosphates, sulfates, and/or thiophosphates with or without covalent addition of poly(ethylene glycol) (PEG) or polyglycerol, in preventing or reducing pathological crystallization in soft tissues.

A first aspect of the invention relates to method for treatment of a condition associated with formation of, and/or tissue exposure to, calcium salt crystals, the method comprising administering to a subject in need thereof an inositol polyphosphate oligo alkyl ether compound. In the broadest sense, the condition is chronic kidney disease associated with calcium salt precipitation, particularly with the formation of precipitates comprised of calcium phosphate and/or oxalate.

Without wanting to be limited by theory, the inventors draw the conclusion from these results provided herein, that pathophysiologic mechanisms of the diseases mentioned here involve, as a first step, precipitation of calcium phosphate matter, which subsequently grows, adheres to cells (and perhaps grows further once adhered to cells). The interaction of the calcium phosphate precipitates with renal tubular cells, whether the precipitates are large or small, causes damage to the cells.

The compounds and compositions provided herein apparently stop new precipitates from forming/growing but it also stop existing precipitates from adhering to the cells, both of which confer a protective effect. There is therefore a dual mode of action.

BRIEF DESCRIPTION OF THE FIGURES

FIG. 13 shows an overview of the efficacy of screened compounds to inhibit CaP precipitation in RTF. Overview table showing the minimal concentration of compound (FIG. 3 for the chemical structures) required to achieve complete inhibition of CaP precipitation (total area covered with crystals <10% of total area control); and minimal concentration required to prevent CaP crystal aggregation in the CaP screening assay (CaP aggregate size <50% of aggregate size control) (N=3).

FIG. 14 shows serum and urinary phosphate and calcium levels measured in the different treatment groups of mice (mean±SD).

DETAILED DESCRIPTION

Terms and Definitions

Figure 1:
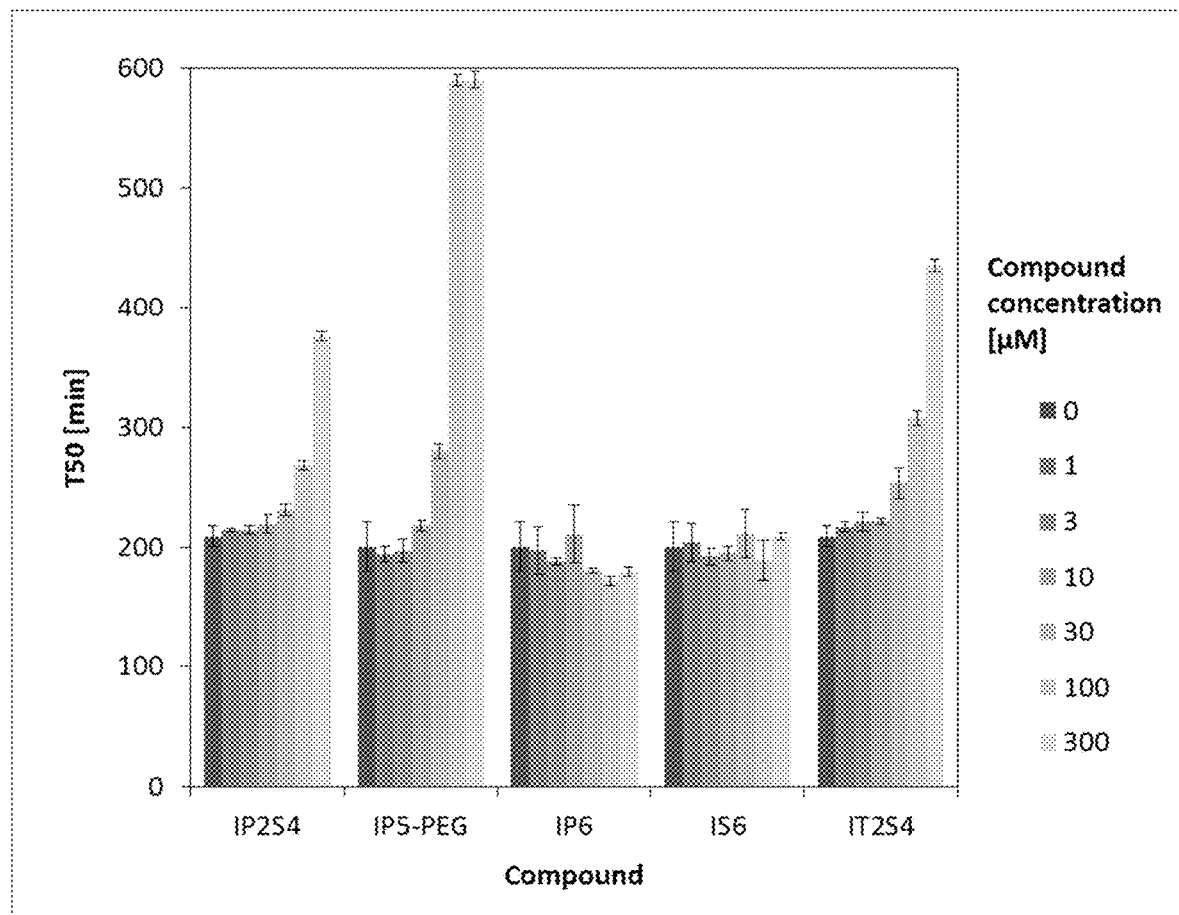
FIG. 1 shows calciprotein particle (CPP) maturation time in human serum according to the test described in Pasch et al. JASN 2012. The y-axis indicates the half-maximal transition time ($T_{50}$) in minutes of primary CPPs to secondary CPPs. IP6: myo-inositol hexakisphosphate (Biosynth); IS6: myo-inositol hexakissulfate (Sigma); IP2S4: 4,6-di-(O-phosphate)-myo-inositol 1,2,3,5-tetra-O-sulfate; IT2S4: 4,6-di-(O-thiophosphate)-myo-inositol 1,2,3,5-tetra-O-sulfate; IP5-PEG: 2-PEG(2000)-myo-inositol pentakisphosphate.

For purposes of interpreting this specification, the following definitions will apply and whenever appropriate, terms used in the singular will also include the plural and vice versa. In the event that any definition set forth below conflicts with any document incorporated herein by reference, the definition set forth shall control.

The terms "comprising," "having," "containing," and "including," and other similar forms, and grammatical equivalents thereof, as used herein, are intended to be equivalent in meaning and to be open ended in that an item or items following any one of these words is not meant to be an exhaustive listing of such item or items, or meant to be limited to only the listed item or items. For example, an article "comprising" components A, B, and C can consist of (i.e., contain only) components A, B, and C, or can contain not only components A, B, and C but also one or more other components. As such, it is intended and understood that "comprises" and similar forms thereof, and grammatical equivalents thereof, include disclosure of embodiments of "consisting essentially of" or "consisting of."

Where a range of values is provided, it is understood that each intervening value, to the tenth of the unit of the lower limit, unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

Reference to "about" a value or parameter herein includes (and describes) variations that are directed to that value or parameter per se. For example, description referring to "about X" includes description of "X."

As used herein, including in the appended claims, the singular forms "a," "or," and "the" include plural referents unless the context clearly dictates otherwise.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 4th ed. (2012) Cold Spring Harbor Laboratory Press, Cold Spring Harbor, N.Y. and Ausubel et al., Short Protocols in Molecular Biology (2002) 5th Ed, John Wiley & Sons, Inc.) and chemical methods.

In the context of the present specification, the term oligo-alkylether relates to oligo-ethylene glycol and close chemical relatives such as oligo-propylene glycol and oligo-glycerol. The term "oligo" signifies that more than one, particularly from 2 to 20, more particularly from 2 to 12 monomers (—$CH_2$—$CH_2$—O—) in the case of oligo-ethylene glycol, (—$CH(CH_3)$—$CH_2$—O—) in the case of oligo-propylene glycol) are present.

In the context of the present specification, the term inositolpolyphosphate relates to cyclohexane-hexol (inositol, cyclohexane-1,2,3,4,5,6-hexol) wherein each OH is substituted by a phosphate ester moiety unless the OH is substituted by an oligo-alkylether moiety according to the preceding definition. In particular embodiments, the inositol scaffold is myo-inositol ((1R,2S,3R,4R,5S,6S)-cyclohexane-1,2,3,4,5,6-hexol).

The term inositol polyphosphate oligo-alkylether compound in the context of the present specification relates to a compound comprising one or several inositol polyphosphate moieties as defined above, and at least one oligoalkylether.

The term calcification in the context of the present specification relates to the formation of calcium precipitates in the affected tissue, particularly renal tissue.

Calcium Precipitates

The chemical composition of calcium crystalline precipitates associated with renal and cardiovascular disease is well studied (see Elliot, J Urology 100 (1968), 687-693; Xie et al., Cryst Growth Des. 2015 Jan. 7; 15(1): 204-211). In principle, the treatment according to the invention is capable of preventing or ameliorating any condition in which deposition of calcium phosphate, oxalate and mixed calcium phosphate-oxalate crystals play a role.

Calcium phosphate is found in different crystal forms in pathologic deposits in the human body; these include hydroxyapatite (hydroxylapatite, HA, $Ca_{10}(PO_4)_6(OH)_2$), brushite ($CaHPO_4*2\ H_2O$), monetite, and various amorphous calcium phosphate salts.

Calcium oxalate in pure form is found as a mono- (whewellite), di- (weddellite) and tri-hydrate, and often associated with other deposits, mainly phosphate salts.

The results presented in the examples show that any of the cellular sequelae of calcium salt crystal formation, even when associated with deposits preceding the stage of macroscopically detectable calcification, can be prevented by treatment according to the invention as described in the present specification.

Diseases Associated to Calcium Precipitation that Benefit from Treatment According to the Invention "Renal fibrosis" or "tubulointerstitial fibrosis" associated with formation of, and/or tissue exposure to, calcium salt crystals, refers to a thickening and scarring of kidney tissue, due to unsuccessful wound-healing after chronic injury due to exposure to calcium phosphate, calcium oxalate or mixed CaP/CaOx precipitates. During this process fibrotic matrix deposition continues unchecked leading to glomerulosclerosis, tubular atrophy and interstitial fibrosis. Patients suffering from said disease can experience intense abdominal pain (with bleeding or haemorrhaging), swelling and discoloration in one or both legs, and ultimately progress to chronic kidney disease.

"Renal inflammation" or "nephritis" is defined as a complex network of interactions between renal parenchymal cells and resident immune cells, such as macrophages and dendritic cells, coupled with recruitment of circulating monocytes, lymphocytes, and neutrophils. Once stimulated, these cells activate specialized structures such as Toll-like receptor and Nod-like receptor (NLR). By detecting danger-associated molecules, these receptors can set in motion major innate immunity pathways such as nuclear factor κB (NF-κB) and NLRP3 inflammasome, causing metabolic reprogramming and phenotype changes of immune and parenchymal cells and triggering the secretion of a number of inflammatory mediators that can cause irreversible tissue damage and functional loss. In CKD, a chronic inflammation leads to a progressively decreasing glomerular filtration rate (GFR) that can ultimately result in kidney failure (end stage renal disease, ESRD).

To the extent that renal inflammation/nephritis is associated or caused by interaction of renal tissue with calcium deposits, the treatment according to the invention is expected to ameliorate or prevent the condition. The examples shown herein demonstrate that calcium phosphate deposition/exposure leads to upregulation of inflammation and fibrosis markers in the kidneys, therefore any disease that consists of inflammation and fibrosis of the kidneys should benefit from treatment that inhibits the formation of deposits. For each of these inflammatory conditions, there may also be other, even concurrent causes for the inflammation and fibrosis, as both of these are often multifactorial processes. Abrogation of one contributing factor, however, is expected to improve the overall clinical picture.

"Glomerulonephritis" refers to a group of diseases that are characterized by inflammatory changes in glomerular capillaries. Patients suffering from said group of diseases can experience proteinuria, impaired renal function in some cases paired with fluid retention, hypertension and oedema. Glomerulonephritis can occur as a primarily renal disease as well as indicate a systematic disease process. When associated with formation of, and/or tissue exposure to, calcium salt crystals, glomerulonephritis is expected to benefit from treatment with the compounds described herein.

"Interstitial nephritis" refers to inflammation of the renal interstitium which can be caused by unbalanced levels of calcium. Symptoms include increased urine output, hematuria, changes in mental status, swelling. This condition, if associated with formation of, and/or tissue exposure to, calcium salt crystals, is expected to benefit from treatment with the compounds described herein.

Figure 2:
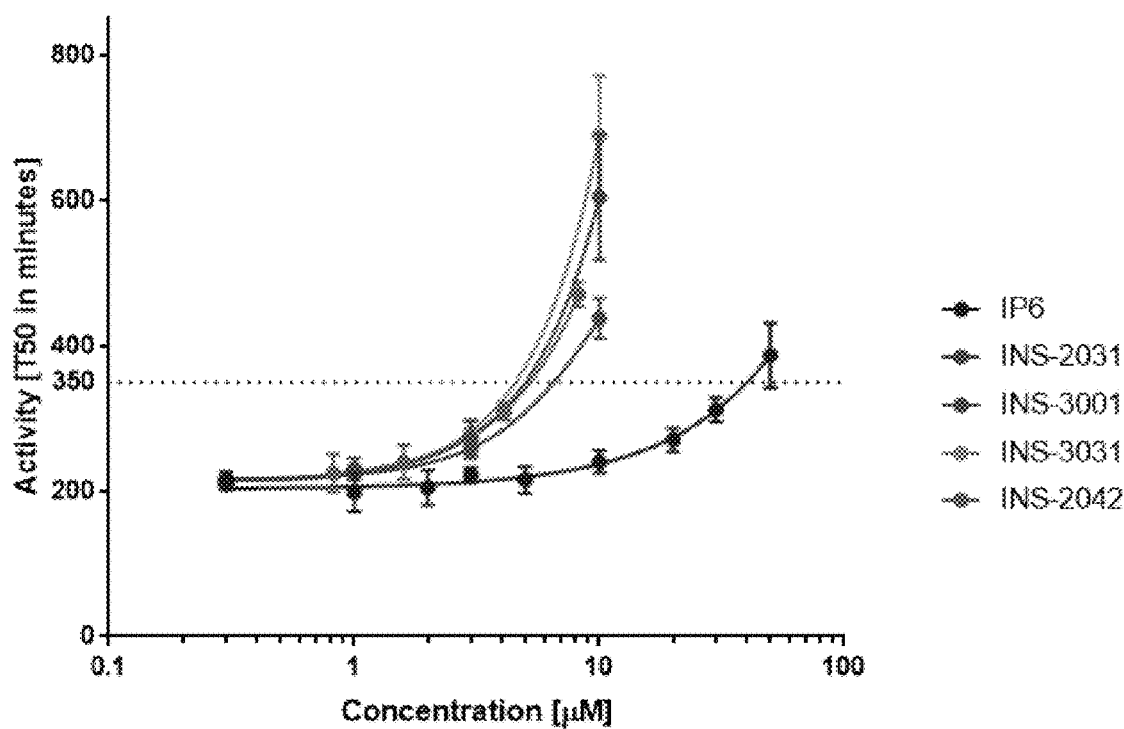
FIG. 2 shows the result of a determination of calciprotein particle (CPP) maturation time in human serum according to a similar test as in FIG. 1 (with the test compounds added to the reaction mixture last).

"Phosphate-induced renal fibrosis" may be associated with a range of calcium and phosphate concentrations that lead to precipitation in the renal tubules, see the data presented in FIG. 2: i.e. calcium >2 or 5 mmol/L and phosphate >5 or 7 mmol/L. Of note, there can be elevated phosphate in renal tubular fluid (leading to its precipitation with calcium) even when detectable plasma phosphate levels are normal (i.e. in the absence of hyperphosphatemia). Elevated plasma phosphate is a terminal consequence of end-stage renal disease that occurs when kidney function is below a 20% threshold.

"Phosphate-induced chronic kidney disease" Phosphate-induced CKD can occur even if plasma phosphate levels are normal (i.e. in earlier stage CKD patients). Reference values can be calcium >2 or 5 mmol/L and phosphate >5 or 7 mmol/L in the renal tubules.

"Chronic kidney disease associated with hyperphosphatemia" refers to hyperphosphatemia occurring in progressive CKD, due to the increasing loss of GFR. This leads to the blocking of tubular phosphate reabsorption and therefore increased phosphate retention, in other words, less phosphate clearance, impairing phosphate homeostasis (Sharon M. Moe, Prim Care. 2008 June; 35(2): 215-vi.). A useful reference value to characterize patients who are expected to benefit from the treatment according to the invention can be a plasma phosphate level of >1.46 mmol/Ls.

"Progression of chronic kidney disease" refers to five stages, ranging from the first stage (mild damage, eGFR 90 or greater) to the fifth (complete kidney failure, eGFR less than 15). Current guidelines determine the critical GFR for CKD to be less than 60 mL/min per 1.73 m² over a period of 3 months.

"Phosphate toxicity" refers to a dysregulated renal phosphate excretion and reabsorption, impairing phosphate homeostasis, which can cause severe damage of kidney tissue. (Razzaque, Clin Sci (Lond). 2011 February; 120(3): 91-97). To the extent that this condition causes tissue damage associated with formation of, and/or tissue exposure to and/or deposition of crystals which can avoided by the treatment according to the invention, the treatment is indicated for patient suffering from the condition.

"Hyperphosphaturia" or "phosphaturia" refers to a high level of phosphate in urine. To the extent that this condition causes tissue damage associated with formation of, and/or tissue exposure to and/or deposition of crystals which can avoided by the treatment according to the invention, the treatment is indicated for patient suffering from the condition.

"Hyperphosphatemia" refers to an elevated (>4.5 mg/dL; >1.46 mmol/L) phosphate level in blood. To the extent that this condition causes tissue damage associated with formation of, and/or tissue exposure to and deposition of crystals which can avoided by the treatment according to the invention, the treatment is indicated for patient suffering from the condition.

"Hyper-FGF23-emia" refers to an increased fractional phosphate excretion, paired with a decrease of serum phosphate levels, due to elevated fibroblast growth factor (FGF)-23 levels.

"Vascular calcification" refers to the pathological deposition of minerals in the vascular system often observed in patients suffering from CDK or diabetes. The elevated calcium and/or phosphate levels can be the result of metabolic dysregulation caused by diabetes, dyslipidemia, oxidative stress, uremia, and hyperphosphatemia, which lead to osteoblast-like cell formation, appearance of calcified deposits and stiffening in the vessel wall.

"Coronary artery disease" or "artheroslerotic heart disease" refers to an accumulation of plaque in damaged inner layers of the coronary artery. Factors such as inflammatory cells, lipoproteins and calcium attach to the plaque leading to further stenosis. Progression of this disease can ultimately lead to myocardial infarction or stroke.

"Vascular stiffening" refers to stiffening of the arterial wall due to calcification. Vascular stiffening consists of lower elasticity of the vasculature leading to an increased pulse wave pressure.

"Valve calcification", particularly aortic valve calcification, refers to an active dysregulation of normal homeostatic processes and hemodynamic changes, such as ECM degradation, fibrosis, lipid accumulation, and neo-angiogenesis of the valve tissue, concurrent with calcification of the valve, in particular the aortic and mitral valves.

"Nephrocalcinosis" refers to the deposition of calcium salts in the renal parenchyma, particularly in the medulla (medullary nephrocalcinosis) or cortex (cortical nephrocalcinosis) of the kidney.

"Calcinosis cutis" refers to the deposition of calcium phosphate precipitates within the skin, particularly within the extremities. If the solubility point of calcium and phosphate are exceeded, precipitation of calcium salts and deposition as amorphous hydroxyapatite occur.

"Kidney stones", "renal calculi", "nephrolithiasis", and "urolithiasis" refer to a mineral deposit in renal tissue, which is due to the accumulation and therefore supersaturation of urine (hypercalcuria).

"Chondrocalcinosis" refers to the accumulation of calcium phosphate in joints.

Particular conditions the treatment of which is expected to benefit, based on the examples described in here, from administration of the compounds described in here further include aortic valve stenosis, peripheral artery disease and brain calcification.

The data shown in example 1 confirm the utility of the compounds disclosed herein as effective in reducing or inhibiting calcium phosphate crystal formation, in the prevention and treatment of idiopathic calcium nephrolithiasis/idiopathic calcium kidney stones, particularly those mainly consisting of calcium phosphate, calcium oxalate, or mixtures thereof.

Compounds Having One Inositol Scaffold

In certain embodiments, the inositol polyphosphate oligo alkyl ether compound, or its pharmaceutically acceptable salt, in the method laid out above, is described by a general formula I, wherein one or two or three X are oligo-ethylene glycol and the remaining X are $OPO_3^{2-}$.

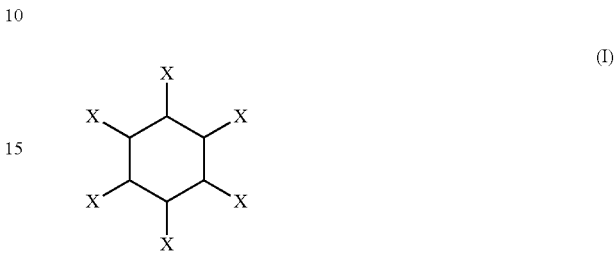

(I)

As shown in the examples provided herein, both mono- and bis-oligo-ethylene glycol derivatives of varying chain length confer inhibition of calcium precipitate formation in a cellular assay. The inositol scaffold can have any stereochemistry. The inventors worked preferably with myo-inositol.

When dissolved in aqueous medium at physiological pH, it is apparent to the skilled artisan that the compounds mentioned herein are anionic and will be accompanied by cations. The buffers used in the screens comprise mainly sodium (408 mmol/L), and traces of potassium (0.26 mmol/L) and magnesium (4 mmol/L).

In certain particular embodiments, two of the inositol substituents X shown in the above formula I are oligo-ethylene glycol and the remaining four X are $OPO_3^{2-}$.

Examples for compounds that can be advantageously used in treatment according to the invention include general formulas I-1, I-2, I-3 and I-4, wherein in each case, X is phosphate and $R^1$ is an oligo-ethylene glycol as set forth herein:

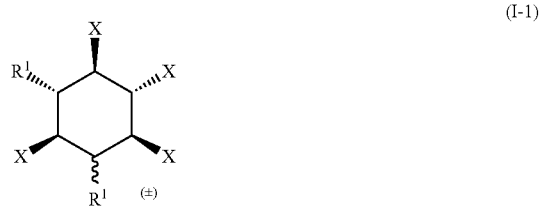

(I-1)

(I-2)

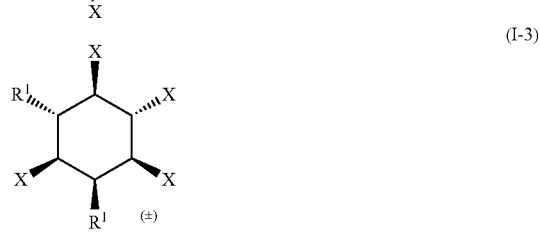

(I-3)

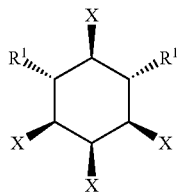

(I-4)

In one more particular embodiment thereto, the scaffold is myo-inositol and the oligo-ethylene glycol substituents are on position 4 and 6, with the rest of the substituents being phosphate. In an even more particular embodiment, the oligo-ethylene glycol substituents are O—(CH$_2$—CH$_2$O)$_2$—CH$_3$.

In other particular embodiments, one of the inositol substituents X shown in the above formula I is oligo-ethylene glycol and the remaining five X are OPO$_3{}^{2-}$. In one more particular embodiment thereof, the scaffold is myo-inositol and the oligo-ethylene glycol substituent is on position 4 or 6, particularly on 6, with the rest of the substituents being phosphate. In an even more particular embodiment, the oligo-ethylene glycol substituent is O—(CH$_2$—CH$_2$O)$_2$—CH$_3$.

In yet other particular embodiments, three of the inositol substituents X shown in the above formula I are oligo-ethylene glycol and the remaining three X are OPO$_3{}^{2-}$. Examples thereof include general formulas I-5 and I-6, wherein in each case, X is phosphate and R$^1$ is an oligo-ethylene glycol as set forth herein:

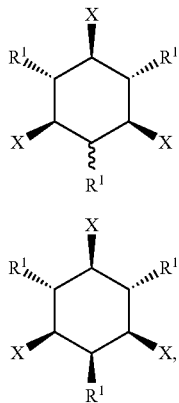

(I-5)

(I-6)

In certain embodiments, the oligo-ethylene glycol substituent (or substituents) of the inositol polyphosphate oligo alkyl ether compound, or its pharmaceutically acceptable salt, provided in the method according to the invention herein, is described by a formula O—(CH$_2$—CH$_2$—O)$_n$CH$_3$, with n being selected from an integer between 2 and 20, particularly n being 2 to 12. Different parameters of the compounds' physiological activity, pharmacological parameters and aspects of manufacture will influence which value of n is optimal.

In certain particular embodiments, the oligo-ethylene glycol substituent (or substituents) of the inositol polyphosphate oligo alkyl ether compound, or its pharmaceutically acceptable salt, provided in the method according to the invention herein, is described by a formula 0-(CH$_2$—CH$_2$—O)$_n$CH$_3$, wherein n is 2. Table 1 of the examples shows the particular advantage of OEG$_2$-IP5 and (OEG$_2$)$_2$-IP4, both of which are characterized by n being 2.

Certain particular embodiments of the compound of the method as specified herein are described by any one of the formulas:

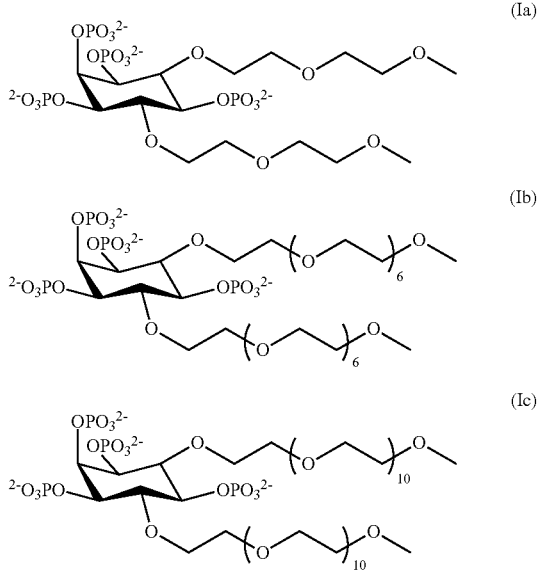

Certain particular embodiments of the compound of the method as specified herein are described by any one of the formulas:

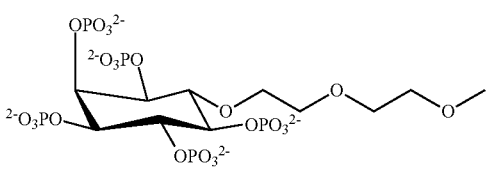

(Id)

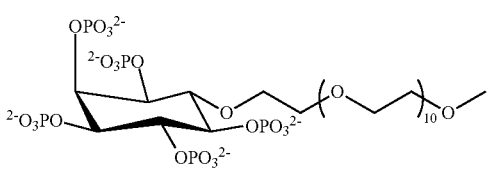

(Ie)

Other embodiments of compounds of the method according to aspect of the invention include:

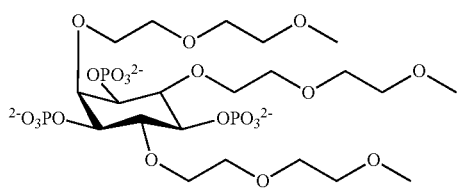

(If)

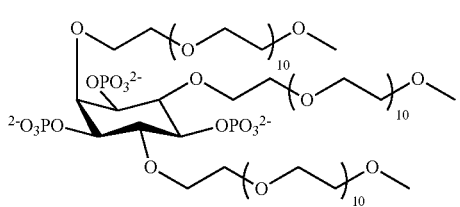

(Ig)

The skilled person is aware that any specifically mentioned drug compound mentioned herein may be present as a pharmaceutically acceptable salt of said drug. Pharmaceutically acceptable salts comprise the ionized drug and an oppositely charged counterion. Non-limiting examples of pharmaceutically acceptable cationic salt forms include aluminium, benzathine, calcium, ethylene diamine, lysine, magnesium, meglumine, potassium, procaine, sodium, tromethamine and zinc.

Method of Manufacture and Method of Treatment According to the Invention

The invention further encompasses, as an additional aspect, the use of an inositol polyphosphate oligo alkyl ether compound, or its pharmaceutically acceptable salt, as specified in detail above, for use in a method of manufacture of a medicament for the treatment or prevention of a disease associated with formation of calcium salt precipitate or calcium salt crystals, specifically in a disease selected from renal fibrosis, particularly when associated with calcification of renal tissue, renal inflammation, particularly when associated with calcification of renal tissue, nephritis, particularly interstitial nephritis, glomerulonephritis, phosphate-induced renal fibrosis, phosphate-induced chronic kidney disease, chronic kidney disease associated with hyperphosphatemia, progression of chronic kidney disease, phosphate toxicity, hyperphosphaturia, hyperphosphatemia, and/or hyper-FGF23-emia.

The compounds of the invention are similarly provided for use in a method of manufacture of a medicament for the treatment or prevention of a disease associated with formation of calcium salt precipitate or calcium salt crystals, the disease being selected from vascular calcification, coronary artery disease, vascular stiffening, valvular calcification, nephrocalcinosis, calcinosis cutis, kidney stones, and chondrocalcinosis.

Similarly, the invention encompasses methods of treatment of a patient having been diagnosed with a disease associated with formation of calcium salt precipitate or calcium salt crystals, specifically in a disease selected from renal fibrosis, particularly when associated with calcification of renal tissue, renal inflammation, particularly when associated with calcification of renal tissue, nephritis, particularly interstitial nephritis, glomerulonephritis, phosphate-induced renal fibrosis, phosphate-induced chronic kidney disease, chronic kidney disease associated with hyperphosphatemia, progression of chronic kidney disease, phosphate toxicity, hyperphosphaturia, hyperphosphatemia, and/or hyper-FGF23-emia. This method entails administering to the patient an effective amount of an inositol polyphosphate oligo alkyl ether compound, or its pharmaceutically acceptable salt, as specified in detail herein.

Pharmaceutical Compositions and Administration

Another aspect of the invention relates to a pharmaceutical composition comprising a compound of the present invention, or a pharmaceutically acceptable salt thereof, and a pharmaceutically acceptable carrier. In further embodiments, the composition comprises at least two pharmaceutically acceptable carriers, such as those described herein.

In certain embodiments of the invention, the compound of the present invention is typically formulated into pharmaceutical dosage forms to provide an easily controllable dosage of the drug and to give the patient an elegant and easily handleable product.

In certain embodiments, the pharmaceutical composition for use according to the invention is formulated for administration by intradermal or subcutaneous injection.

The dosage regimen for the compounds of the present invention will vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. In certain embodiments, the compounds of the invention may be administered in a single daily dose, or the total daily dosage may be administered in divided doses of two, three, or four times daily.

The pharmaceutical composition for use according to the present invention can be subjected to conventional pharmaceutical operations such as sterilization and/or can contain conventional inert diluents or buffering agents, as well as adjuvants, such as preservatives, stabilizers, surfactants and buffers, etc. They may be produced by standard processes, for instance by conventional mixing, dissolving or lyophilizing processes. Many such procedures and methods for preparing pharmaceutical compositions are known in the art, see for example L. Lachman et al. The Theory and Practice of Industrial Pharmacy, 4th Ed, 2013 (ISBN 8123922892).

Wherever alternatives for single separable features are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

EXAMPLES

TABLE 1

Compounds

| Compound | Formula | No. of PEG tails | $M_w$ of PEG (monodisperse) | $M_w$ of compound | Substituents other than PEG |
|---|---|---|---|---|---|
| INS-2001 | III o | 1 | 100 | 672.11 | 5 × $OPO_3^{2-}$ |
| INS-2031 | III p | 1 | 320 | 892.37 | 5 × $OPO_3^{2-}$ |
| INS-2041 | III q | 1 | 500 | 1068.59 | 5 × $OPO_3^{2-}$ |
| INS-2042 | | 1 | 550 (polydisp.) | 1112.64 | 5 × $OPO_3^{2-}$ |
| INS-2101 | III r | 1 | 100 | 752.41 | 5 × $OPSO_2^{2-}$ |
| INS-2131 | III s | 1 | 320 | 972.68 | 5 × $OPSO_2^{2-}$ |
| INS-2141 | III t | 1 | 500 | 1148.89 | 5 × $OPSO_2^{2-}$ |
| INS-4001 | III u | 1 | 100 | 675.37 | 2 × $OPO_3^{2-}$, 3 × $OSO^{3-}$ |
| INS-4031 | III v | 1 | 320 | 895.63 | 2 × $OPO_3^{2-}$, 3 × $OSO^{3-}$ |
| INS-4041 | III w | 1 | 500 | 1071.84 | 2 × $OPO_3^{2-}$, 3 × $OSO^{3-}$ |
| INS-4101 | III x | 1 | 100 | 707.49 | 2 × $OPSO_2^{2-}$, 3 × $OSO^3$ |

TABLE 1-continued

Compounds

| Compound | Formula | No. of PEG tails | $M_w$ of PEG (monodisperse) | $M_w$ of compound | Substituents other than PEG |
|---|---|---|---|---|---|
| INS-4131 | III y | 1 | 320 | 927.75 | $2 \times OPSO_2^{2-}$, $3 \times OSO^3$ |
| INS-4141 | III z | 1 | 500 | 1103.96 | $2 \times OPSO_2^{2-}$, $3 \times OSO^3$ |
| INS-3001 | IV f | 2 | 100 | 696.28 | $4 \times OPO_3^{2-}$ |
| INS-3031 | IV g | 2 | 320 | 1136.81 | $4 \times OPO_3^{2-}$ |
| INS-3041 | IV h | 2 | 500 | 1489.23 | $4 \times OPO_3^{2-}$ |
| INS-3101 | IV i | 2 | 100 | 760.52 | $4 \times OPSO_2^{2-}$ |
| INS-3131 | IV j | 2 | 320 | 1201.05 | $4 \times OPSO_2^{2-}$ |
| INS-3141 | IV k | 2 | 500 | 1553.48 | $4 \times OPSO_2^{2-}$ |
| INS-5001 | V d | 3 | 100 | 720.45 | $3 \times OPO_3^{2-}$ |
| INS-5031 | V e | 3 | 320 | 1381.24 | $3 \times OPO_3^{2-}$ |
| INS-5041 | V f | 3 | 500 | 1909.88 | $3 \times OPO_3^{2-}$ |
| INS-5101 | V g | 3 | 100 | 768.63 | $3 \times OPSO_2^{2-}$ |
| INS-5131 | V h | 3 | 320 | 1429.42 | $3 \times OPSO_2^{2-}$ |
| INS-5141 | V i | 3 | 500 | 1958.06 | $3 \times OPSO_2^{2-}$ |

Synthesis of IT2S4 (VI a)

The synthesis followed the sequence depicted in the scheme below:

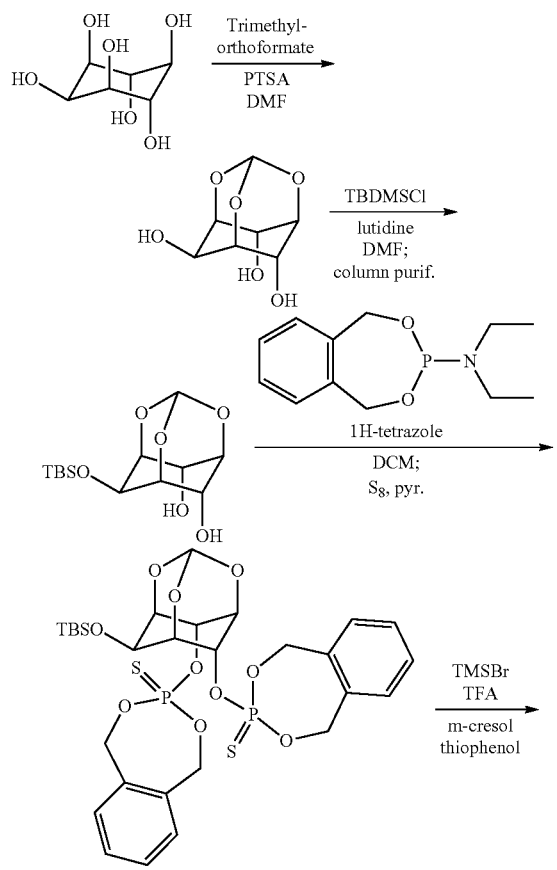

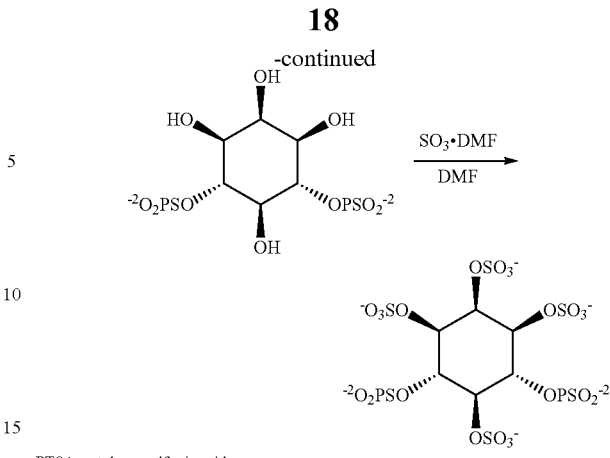

PTSA: p-toluenesulfonic acid;
DMF: dimethylformamide;
TBDMSCl: tert-butyldimethylsilyl chloride;
TBSO: tert-butyldimethylsilyl ether protection group;
DCM: dichloromethane;
S8: elemental sulphur;
pyr.: pyridine;
TMSBr: trimethylsilyl bromide;
TFA: trifluoroacetic acid Phosphorylation The known 2-tertbutyldimethylsilyl inositol orthoformate was co-evaporated 3× with toluene and dissolved in dichloromethane (DCM). 1H-tetrazole (4 eq.) followed by phosphoramidite (8 eq.) were added to the reaction and stirred overnight. Pyridine, followed by crushed sulphur flakes (20 eq.) were added to the reaction and stirred overnight. The resulting crude mixture was diluted with DCM and washed with saturated $NaHCO_3$, dried with $Na_2SO_4$, filtered and concentrated. The product was purified by flash chromatography with DCM in toluene.

$^1$H-NMR (400 MHz; CDCl3): δ 7.35-7.29 (m, 4H), 7.15 (dd, J=6.6, 2.1 Hz, 2H), 7.07-7.04 (m, 2H), 5.54 (d, J=1.1 Hz, 1H), 5.45-5.41 (m, 2H), 5.30-4.97 (m, 8H), 4.51-4.49 (m, 1H), 4.33-4.32 (m, 2H), 4.27 (d, J=1.3 Hz, 1H), 0.93 (s, 9H), 0.13 (s, 6H); $^{31}$P-NMR (162 MHz; CDCl3): δ 70.1;

Deprotection

The following deprotection conditions are in analogy to the synthesis published in the Journal of the American Chemical Society (JACS 2005, 127, 5288).

Starting material (50 mg) was treated with thiophenol (300 μl), m-cresol (300 μl), trifluoroacetic acid (1.8 ml). Trimethylsilyl bromide (TMSBr) was then added slowly (360 μl). The mixture was stirred 2 h at room temperature. And then evaporated twice from toluene. The crude residue was diluted with DCM, and ca. 5 ml water and neutralized with 1N NaOH. The aqueous layer (slightly cloudy) was poured directly on SolEx C18 cartridge (Thermofisher, 1 g, 6 ml) and eluted with water. In some cases some aromatic impurities were found in the final product but would precipitate over time in water and could be filtered-off.

$^1$H-NMR (500 MHz; D$_2$O): δ 4.36 (q, J=9.6 Hz, 2H), 4.02 (t, J=2.7 Hz, 1H), 3.64 (dd, J=9.7, 2.8 Hz, 2H), 3.50 (t, J=9.3 Hz, 1H). $^{31}$P-NMR (203 MHz; D$_2$O): δ 45.7

Sulfation

The sulfation reaction of the thiophosphate has to be performed carefully because the thiophosphate is eventually converted to the phosphate under the reaction conditions. We thus monitored the sulfation carefully and saw that the reaction was complete after ca. 30 min. and that no decomposition could be observed in this time. Thus, sulphurtrioxide dimethylformamide (SO$_3$-DMF) complex (12 eq.) was added to a suspension of inositol phosphate in DMF and the reaction was stirred 35 min. The reaction was quenched by adding 1N NaOH, until ca. pH 8 followed by ca. 3 ml methanol (MeOH) to precipitate salts. The solid was purified by Sephadex LH-20 column, eluting with water.

$^1$H-NMR (500 MHz; D$_2$O): δ 5.06 (s, 1H), 5.04-4.98 (m, 4H), 4.79-4.76 (m, 1H).

$^{31}$P-NMR (203 MHz; D$_2$O): δ 44.5.

Synthesis of IP2S4 (VI c)

The synthesis followed the sequence depicted in the scheme below:

Hz, 1H, H—C2), 3.63 (dd, J=9.68, 2.76 Hz, 2H, H—C1/3), 3.61 (t, J=9.27 Hz, 1H, H—C5);

$^{31}$P-NMR (160 MHz, 1H-decoupled, MeOD): δ (ppm) =1.15 (P—C4/6); 13CNMR (150 MHz, MeOD): δ (ppm) =81.28 (d, 2JCP=6.1 Hz, 2C, C4/6), 74.12 (t, 3JCP=3.8 Hz, 1C, C5), 73.75 (s, 1C, C2), 72.13 (d, 3JCP=3.2 Hz, 2C, C1/3); [m/z (ESI) (M+H)+C6H15O12P2 required 341.0033, found 341.0037].

Sulfation

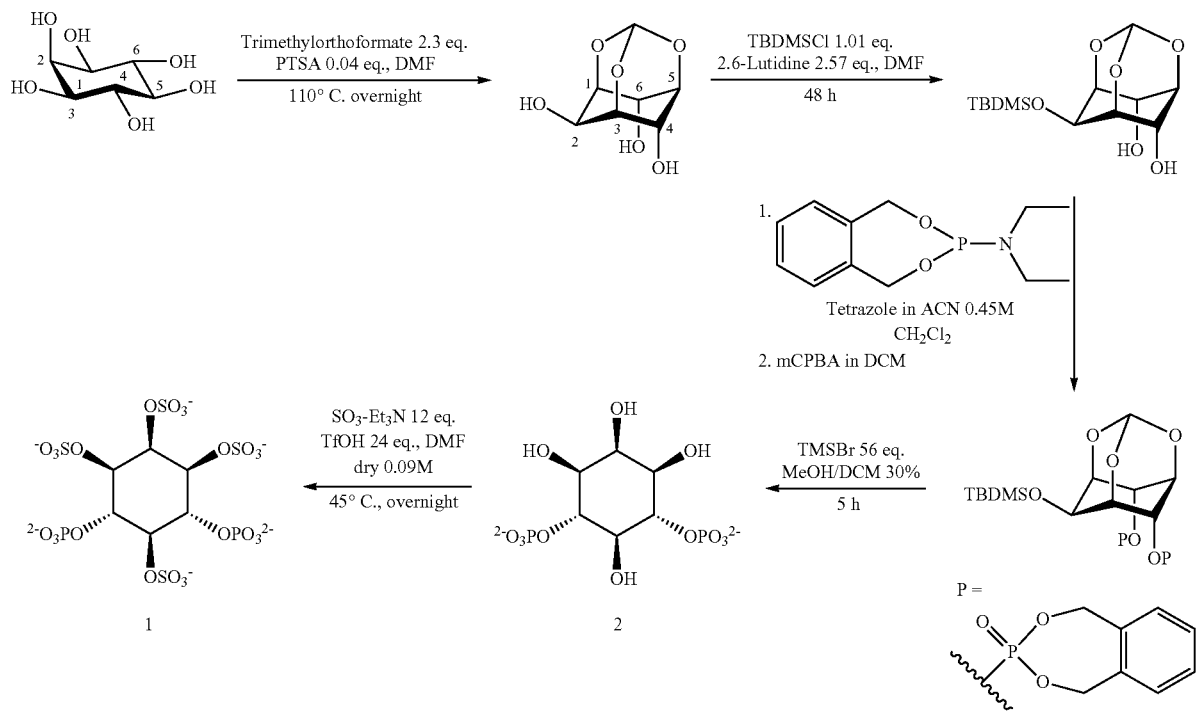

PTSA: p-toluenesulfonic acid; DMF: dimethylformamide;
TBDMSCl: tert-butyldimethylsilyl chloride;
TBDMSO: tert-butyldimethylsilyl ether protection group;
DCM: dichloromethane;
ACN: acetonitrile;
mCPBA: meta-chloroperoxybenzoic acid;
TMSBr: trimethylsilyl bromide;
SO$_3$-Et$_3$N: sulfur trioxide triethylamine;
TfOH: trifluoromethanesulfonic acid Hydrolysis 4,6-Di-O-phosphate-myo-inositol (2)

2-O-Tert-butyldimethylsilyl-1,3,5-orthoformate-4,6-(O-dixylylenephospho)-myo-inositol (1.00 g, 1.5 mmol, 1 eq.) in methanol/dichloromethane (MeOH/DCM) 30% (30 ml, 0.05 M) was treated with trimethylsilyl bromide (TMSBr) (11 ml, 83.8 mmol, 56 eq.) and stirred for 5 h. The reaction mixture was degassed with N$_2$ and the HBr was neutralized with 1 M NaOH solution. After 1-2 h it was concentrated to dryness. The crude was washed twice with acetone and twice with acetonitrile (ACN) to give 2 as a white solid (539 mg, quantitative yield).

$^1$H-NMR (400 MHz, MeOD): δ (ppm)=4.40 (q, 3JHH=9.1 Hz, 2JHP=9.1 Hz, 2H, H—C4/6), 4.01 (t, J=2.6

1,2,3,5-Tetra-O-sulfonyl-4,6-(di-O-phosphate)-myo-inositol (1)

4,6-di-O-phosphate-myo-inositol (30 mg, 90 μmol, 1 eq.) was co-evaporated with toluene (3×) and dried under high vacuum for 1 h. Dry dimethylformamide (DMF) (1 ml, 0.09 M) was added and the reaction mixture was treated with SO$_3$-Et$_3$N (197 mg, 109 μmol, 12 eq.) and TfOH (190 μl, 215 μmol, 24 eq.). It was heated at 45° C. and stirred overnight. The reaction mixture was neutralized by addition of Et$_3$N (0.15 ml, 12 eq.). Immediately after the neutralization the mixture was diluted in nanopure water (2 ml) and loaded on a sephadex G10 column. 14 fractions of 3-4 ml were collected and put into the freeze-dryer overnight. Fractions 3-7 were combined to give 1 as a white solid (46.31 μmol, 51%).

$^1$H-NMR (400 MHz, D$_2$O): δ (ppm)=5.40 (br, 1H, H—C2), 4.64-4.44 (m, 5H, H—C1/3, H—C5, H—C4/6), 3.70 (s, 8H, internal standard dioxane), 3.15 (q, J=7.3 Hz, 6H, CH2-Et₃N), 1.23 (t, J=7.3 Hz, 9H, CH3-Et₃N).

Synthesis of PEG-IP5 (III o, III p, III a)

The synthesis followed the sequence depicted in the scheme below:

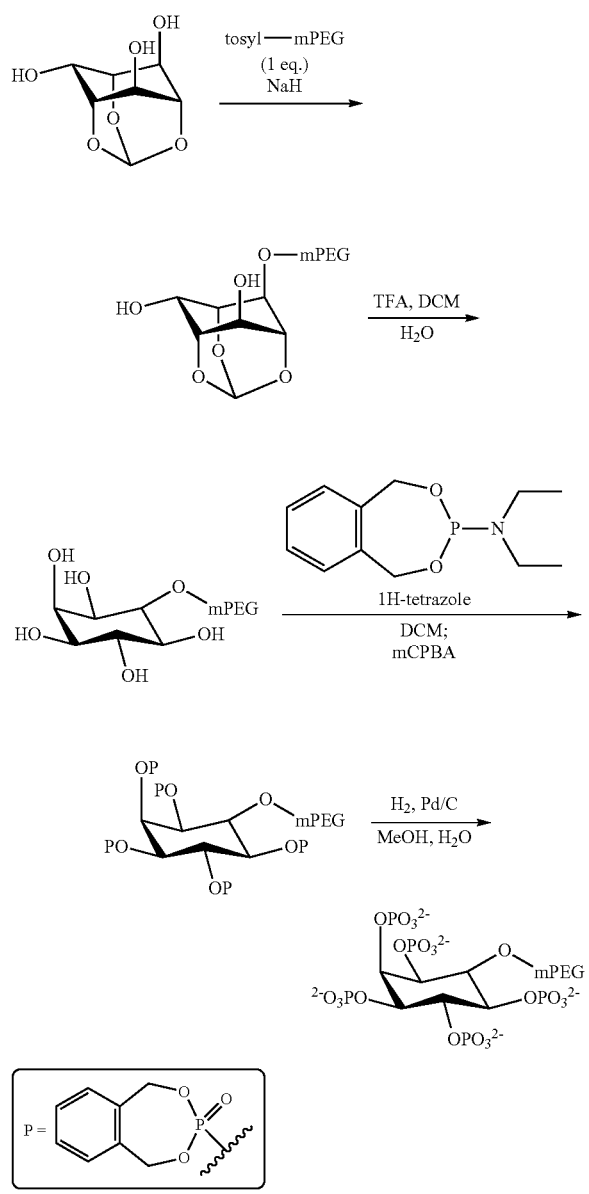

DCM: dichloromethane;
DMF: dimethylformamide;
SBTO: tert-butyldimethylsilyl etherprotection group;
TFA: trifluoroacetic acid;
mCPBA: meta-chloroperoxybenzoic acid Inositol orthoformate was reacted with 1 eq. of PEG tosylate to the singly PEG-ylated 4- or 6-PEG inositol orthoformate. The orthoformate protection group was removed using trifluoroacetic acid and dichloromethane. The compound was reacted with phosphoramidite, 1H-tetrazole, dichloromethane and meta-chloroperoxybenzoic acid. The resulting compound was reacted with H₂, MeOH and PdO to 4-PEG-IP5 or 6-PEG-IP5, respectively.

Synthesis of 4,6-PEG-IP4 (IV f, IV q, IV h)

The synthesis followed the sequence depicted in the scheme below:

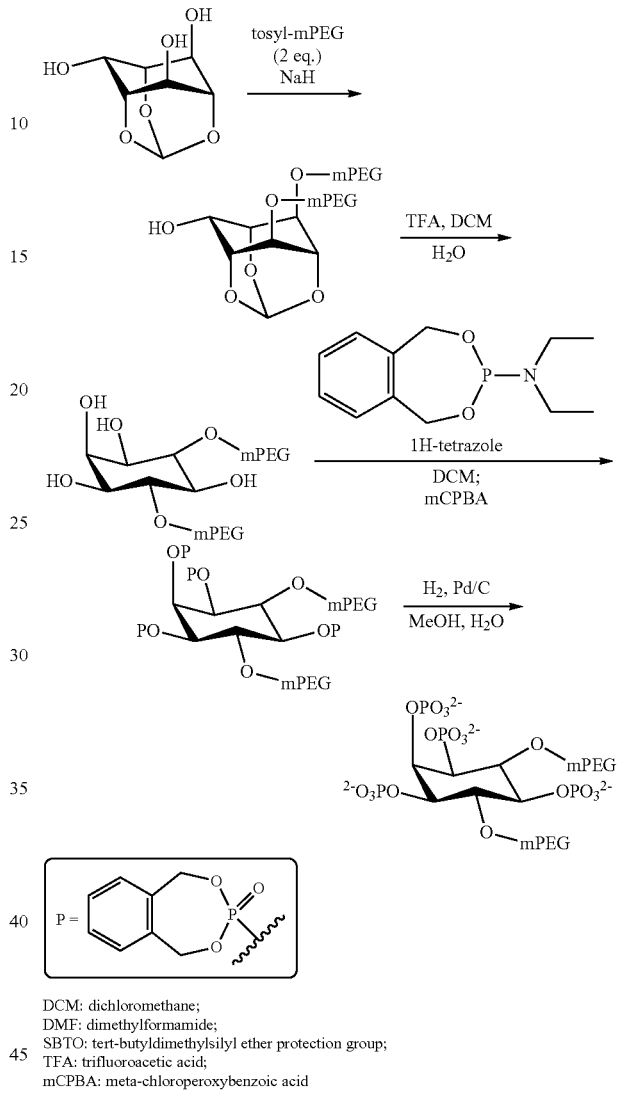

DCM: dichloromethane;
DMF: dimethylformamide;
SBTO: tert-butyldimethylsilyl ether protection group;
TFA: trifluoroacetic acid;
mCPBA: meta-chloroperoxybenzoic acid Inositol orthoformate was reacted with PEG tosylate to the doubly PEG-ylated 4,6-PEG inositol orthoformate. The orthoformate protection group was removed using trifluoroacetic acid and dichloromethane. The compound was reacted with phosphoramidite, 1H-tetrazole, dichloromethane and meta-chloroperoxybenzoic acid. The resulting compound was reacted with H₂, MeOH and PdO to 4,6-PEG-IP4

Synthesis of 4-PEG-IP2S3 (III u, III v, III w)

The synthesis followed the sequence depicted in the scheme below:

The known myo-inositol orthoformate can be mono alkylated with a commercial PEG tosylate in the presence of a strong based such as sodium hydride in DMF. The reaction mixture is then quenched with water and extracted with dichloromethane. The organic layer is dried and concentrated under reduced pressure. The product can be purified by silica gel chromatography. Phosphorylation of the free hydroxyl groups is done under standard conditions using a phosphoramidite reagent followed by oxidation with metachloroperbenzioc acid. The product can be purified by normal or reverse phase chromatography. The orthoester and phosphate groups are then deprotected concomitantly using excess bromotrimethylsilane in a mixture of methanol and dichloromethane. The product can be purified by precipitation or reverse phase chromatography. Sulfation of the free hydroxyl group is performed by suspending the product in dry DMF and reacting with excess sulfur trioxide-DMF complex. The reaction is then quenched with water and neutralized. The final product can be precipitated out of the reaction mixture by adding methanol and purified by size-exclusion chromatography or reverse phase chromatography.

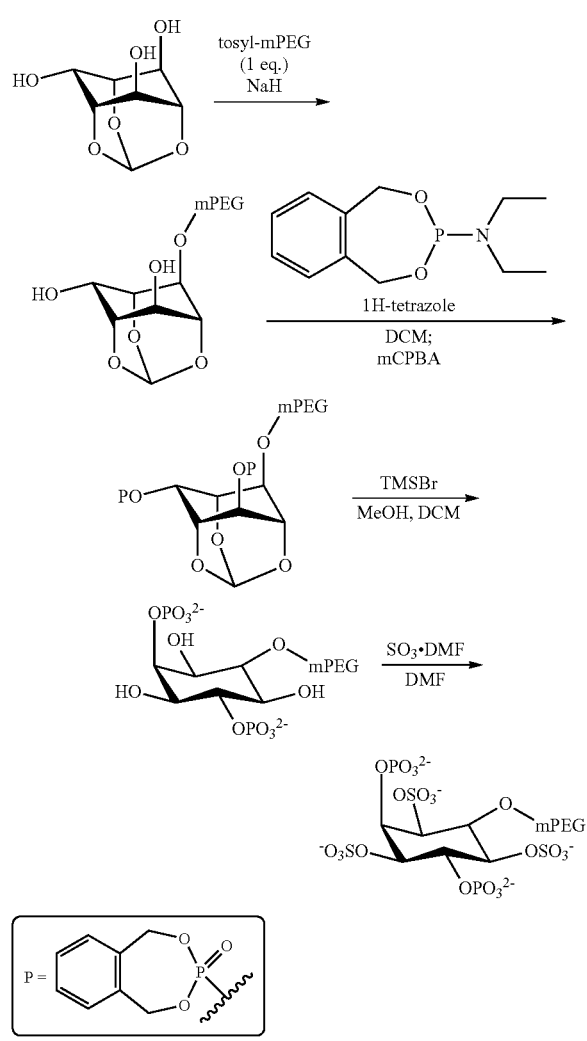

Synthesis of PEG-IT5, 4,6-PEG-IT4 and PEG-IT2S3

The synthesis of PEG-IT5 (III r, III s, III t), 4,6-PEG-IT4 (IV i, IV j, IV k) and PEG-IT2S3 (III x, III y, III z) followed the sequences specified for PEGIP5, 4,6-PEG-IP4 and PEG-IP2S3, except that the phosphorylation was performed by addition of 1H tetrazole (4 eq.) followed by phosphoramidite (8 eq.) to the reaction and stirred overnight. Afterwards, pyridine, followed by crushed sulphur flakes (20 eq.) were added to the reaction and stirred overnight to complete the thiophosphorylation.

Synthesis of 2,4,6-PEG-IP3 (V d, V e, V f)

The synthesis followed the sequence depicted in the scheme below:

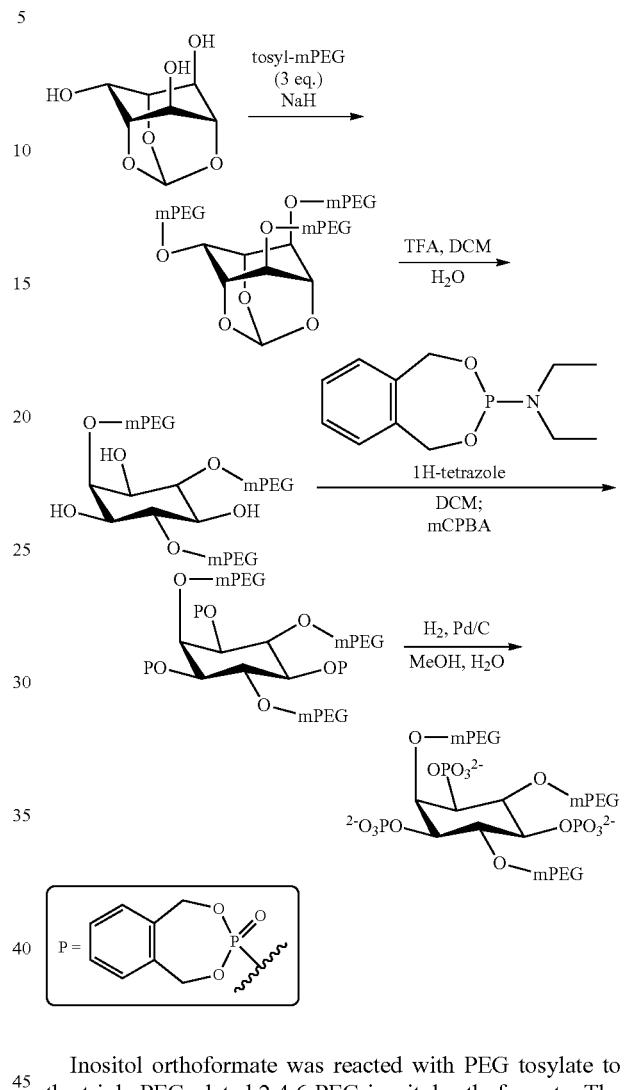

Inositol orthoformate was reacted with PEG tosylate to the triple PEG-ylated 2,4,6-PEG inositol orthoformate. The orthoformate protection group was removed using trifluoroacetic acid and dichloromethane. The compound was reacted with phosphoramidite, 1H-tetrazole, dichloromethane and meta-chloroperoxybenzoic acid. The resulting compound was reacted with $H_2$, MeOH and PdO to 2,4,6-PEG-IP4.

Synthesis of 2,4,6-PEG-IT3 (V Q, V h, V i)

The synthesis of 2,4,6-PEG-IT3 followed that described for 2,4,6-PEG-IP3 except that the phosphorylation was performed by addition of 1H tetrazole (4 eq.) followed by phosphoramidite (8 eq.) to the reaction and stirred overnight. Afterwards, pyridine, followed by crushed sulphur flakes (20 eq.) were added to the reaction and stirred overnight to complete the thiophosphorylation.

Materials

IP6 analogues were custom synthesized by Chimete Srl (Tortona, Italy). Mass and $^1$H-NMR spectra were taken by the provider to confirm the structure and the compounds were used as provided. Phytic acid dodecasodium salt was purchased from Biosynth AG (Thal, Switzerland). IP5 and IS6 hexapotassium salt were purchased from Santa Cruz Biotechnology (Dallas, Tex., United States). IC6 was purchased from Fluorochem (Hadfield, United Kingdom). Calcium Colorimetric Assay kit (MAK022), Bis-Tris, sodium oxalate (NaOx), EthD, Hoechst 33342, magnesium chloride hexahydrate, sodium phosphate dibasic, and calcein were purchased from Sigma-Aldrich (St. Louis, Mo., USA). Sodium chloride, sodium sulphate anhydrous and calcium chloride ($CaCl_2$) dihydrate were obtained from Merck (Kenilworth, N.J., USA). Calcium oxalate (CaOx) monohydrate was purchased from abcr (Karlsruhe, Germany). 8-well glass bottom slides (80 827) were purchased from ibidi (Martinsried, Germany). CellMask Deep Red Plasma Membrane Stain, standard cell culture plates and reagents were purchased from Thermo Fisher Scientific (Rochester, N.Y., USA) and TPP (Trasadingen, Switzerland). RPTEC/TERT1 cells, ProxUp basal medium, and supplements were obtained from Evercyte (Vienna, Austria). RNeasy kit was purchased from Quiagen (Hilden, Germany) and TrueSeq RNA kit from Illumina (San Diego, Calif., USA). RNAiso Plus was obtained from TaKaRa (Kusatsu, Japan). ReverTra Ace qPCR RT Master Mix with gDNA Remover and SYBR Green PCR Master mix were purchased from Toyobo (Osaka, Japan).

In-Solution Screening

An artificial renal tubular fluid (RTF) with a final composition of 0.05 mM oxalate, 0.005 mM sulphate, 408 mM sodium, 424 mM chloride, 0.26 mM potassium, 4 mM magnesium and 0.2 mM citrate in double distilled water was prepared according to a literature report (Fasano, J. M. et al., Kidney Int. 59, 169-178. DOI: 10.1046/j.1523-1755.2001.00477.x, 2001). The solution was filtered with a 0.45-μm syringe filter. Twenty mM Bis-Tris buffer was added to the reported protocol to ensure pH stability throughout experiments and pH was set to 7.2. The artificial RTF was stored at room temperature for up to four months. Stock solutions of 0.25 M phosphate and 1 M calcium were prepared in double distilled water and were stored separately at −20° C.

Twenty-x final concentration phosphate, 20× final concentration calcium and 10× final concentration compound dilutions were prepared in RTF. Assay mixture consisting of 80% RTF, 10% compound dilution, 5% phosphate dilution and 5% calcium dilution was prepared in Eppendorf tubes as follows. RTF (320 μL) was mixed with 20 μL phosphate dilution (final concentration of 9 mM), 40 μL compound dilution and 20 μL calcium dilution (final concentration of 8 mM). The assay mixture was vortexed after adding each component and 380 μL of the mixture were immediately added to 8-well glass bottom slides and incubated for 4 h at RT. CaP precipitation was assessed using a Leica DM 6000B microscope (Leica Microsystems, Wetzlar, Germany) in brightfield mode. For quantification 3 wells/condition with 3-4 images/well were imaged with a 40× objective. The total area covered with CaP deposits in percentage of the field of view and the mean size of CaP aggregates were determined.

Cell Culture

RPTEC/TERT 1 human proximal tubule cells (RPTEC) were cultured in T75 tissue culture flasks using ProxUp basal medium mixed with ProxUp supplements at 37° C. and 5% $CO_2$ according to manufacturer's recommendations. Cells were used up to passage 30 and regularly tested for *Mycoplasma* infections. For experiments, RPTEC were cultured in 24-well plates at a seeding density of 150'000 cells/$cm^2$. Cell viability assessment and cell counting before seeding was performed using an automated cell counter (BioRad TC 20, Hercules, Calif., USA).

Imaging Assay

At t=48 h after seeding, RPTEC were treated with ProxUp basal medium spiked with first, various concentrations of phosphate (final concentration between 1 and 7 mM) and second, calcium (final concentration between 1 and 7 mM), which was directly added to each well.

For the comparison of selected IP6 analogues, ProxUp basal medium was prepared with the selected inhibitor and added to each well. Then, CaP precipitation was induced by direct addition of first, phosphate and second, calcium. Final concentrations of 7 mM phosphate and 5 mM calcium were used. Cells were incubated for 24 h at 37° C. and 5% $CO_2$. Spiked medium was removed, and cells were washed twice with PBS before staining.

For the assessment of CaP-induced CaOx crystallization, after 24 h of incubation, Ca/P spiked medium was removed, and cells were washed twice with PBS. Subsequently, medium containing 1.2 mM oxalate and compound was added to each well. After 4 h of incubation at 37° C. and 5% $CO_2$ treatment was removed, and cells washed once with PBS before staining.

For staining, ProxUp basal medium was mixed with calcein (500 nM final concentration), EthD (6 μM final concentration), CellMask stain (5 μg/μL) and Hoechst 33342. Staining mixture was added to RPTEC and cells were incubated for 30 min in the dark at 37° C. and 5% $CO_2$. Staining solution was removed, cells were washed with PBS once and ProxUp basal medium was added. Cells were immediately imaged after staining. Images were obtained by epifluorescence microscopy at 37° C., using a Leica CTR6000 microscope. For quantification 3 wells/condition were prepared and 3 images/well were taken. For preliminary adhesion experiments images were taken with a 10× objective, for the imaging assay 20× objective images were taken.

Calcium Colorimetric Quantification

For colorimetric quantification of the calcium content of cell monolayers after Ca/P treatment a previously reported protocol was used. In brief, after 24 h of Ca/P incubation cell monolayers were stained and imaged as described above. Then, cells were washed 1× with PBS before overnight incubation with 250 μL of 0.1 M HCl at 4° C. to decalcify cell monolayers. HCl solution was collected, centrifuged at 10,000×g, 4° C. for 4 min and calcium content determined using the Calcium Colorimetric Assay kit (MAK022).

Cell Image Analysis

Multichannel images were saved as individual channel images in 8-bit tiff format. For analysis Hoechst channel images were thresholded using the triangle threshold. Touching nuclei of the binary image were further segmented using the watershed algorithm with the distance transform of the binary image as input and local maxima thereof as seeds.

For EthD channel images, high level of background noise was observed, potentially as a result of fluorescence of the CellMask stain bleeding through. Thus, it was found that using the 99 percentile of all intensity values per image as a threshold resulted in a good detection of foreground pixels. A fixed minimum threshold was set at 60. Watershed segmentation similar to the Hoechst channel was performed to segment touching objects. For the calcein channel images adaptive thresholding by triangle thresholding achieved good detection of CaP deposits, which was validated by visual comparison to brightfield channel images. For compound experiments, an additional upper threshold was set to the minimum threshold of the pos.ctrl images for the respective experiment. Thereby an overly insensitive threshold in images with a high amount of CaP deposition was circumvented. The sum of foreground pixels of the binary image was used to calculate the total area of CaP deposits. The skimage label algorithm was used to label touching foreground regions.

To segment images to single cells the CellMask channel image was first binarized by adaptive thresholding, using a blocksize of 35, followed by median filtering. Binary erosion was performed to shrink the outlines. A version of watershed algorithm was used to segment the whole image into single cells. To this end, the distance transform of the binary erosion image was used as input image and seeds were set to the local maxima of the Hoechst channel image. While this protocol allowed for an approximation of single cell morphology, further improvements of both analytical and experimental staining procedure would be necessary to achieve more accurate results.

Additionally, texture features of calcein and CellMask channel images were extracted. Grey level co-occurrence matrices were calculated using one set offset of 5 pixel and an angle of 90°. Here, the use of larger offsets could improve the detection of changes in large-scale features, e.g. CaP clustering sites. Texture properties of the matrices extracted were contrast, dissimilarity, energy, ASM, homogeneity and correlation. Overlap between calcein and CellMask channel images was measured by computing the structural similarity index matrix (SSIM).

Features extracted included both single cell or single calcein patch features, as well as whole image features. Whole image features included a total cell count based on the Hoechst image, a total dead cell count based on the ethd channel image, SSIM, texture features of both calcein and CellMask channel images and maximum, minimum, mean and standard deviation, total area and cluster count of calcein intensities. Single cell, single nuclei and single calcein patch features included shape and, only for calcein and cell, intensity properties and were summarized to median values per image. Properties included median area, extent, eccentricity, perimeter, solidity, major and minor axis length, as well as maximum, minimum and mean intensity per cell or CaP patch. Features were scaled ranging from 0 to 1 using the MinMaxScaler from the sklearn preprocessing package. The mean value of each image feature over 9 images (3 wells*3 images/well for each condition) per condition was calculated for each experiment and three independent experiments were used for the final analysis. Analysis was performed in Python 3 using the numpy, pandas, skimage, sklearn and seaborn packages.

RNA Sequencing

Cells were cultured as described in the imaging assay and treated with a medium control (ProxUp basal medium containing 1/1 mM Ca/P), 5/7 mM Ca/P, 5/7 mM Ca/P in medium containing 50 μM $(OEG_2)_2$-IP4 or 50 μM $(OEG_2)_2$-IP4 in medium for 24 h. Total RNA was extracted using the RNeasy kit (Quiagen) according to the manufacturer's instructions. Three wells per sample group were prepared and total RNA extracted of those 3 wells pooled. mRNA was purified and RNAseq library was prepared using the TrueSeq RNA kit (Illumina). Sequencing was performed on a Novaseq 6000 (Illumina). Reads were aligned to the human reference genome GRCh38.p10 using the STAR tool (https://github.com/alexdobin/STAR) and transcripts quantified using the Kallisto program (42). Ensembl release 91 was used for the gene model definitions. For the heatmap and hierarchial clustering of significantly different genes ($p \leq 0.01$, log 2fold change $\geq 0.5$) the $\log_2$-fold changes in comparison to the mean of all samples was calculated and log 2fold changes >4 were set to 4. The heatmap was plotted using R software. Overrepresentation analysis was performed on Webgestalt.org (v2019) (43), using differentially expressed genes with $p \leq 0.01$, log 2fold change $\geq 0.5$. Differential expressed genes were compared to the gene ontology-biological process functional database and as a reference set the human genome-protein coding was used. The weighted set cover of the top 30 enriched categories was plotted. For comparison of expression levels of the selected genes, the fragments per kilobase of exon model per million reads mapped (FPKM) were used. Three independent experiments were performed. RNA sequencing raw data is available on the EMBL Nucleotide Sequence Database (ENA) under the accession number PRJEB38397.

Animal Studies

C57BL/6 male mice (12 weeks of age) were placed on either regular diet containing 0.35% inorganic phosphate or high phosphate diet containing 2.0% inorganic phosphate. These mice were subcutaneously injected with either $(OEG_2)_2$-IP4 (100 mg/kg) or vehicle (distilled water) three times a week and then sacrificed at 20 weeks of age to harvest their blood and kidneys. Some mice were transferred individually to metabolic cages to collect urine for 3 days before sacrifice. Serum FGF23 levels were measured using intact FGF23 ELISA (Kinos) according to the manufacturers' protocols. Serum and urine levels of phosphate were measured using Fuji Dri-Chem slides and the analyzer (Dri-Chem NX500V, Fuji, Tokyo, Japan). Frozen mouse kidneys were homogenized with RNAiso Plus (Takara, Osaka, Japan). The lysates were extracted with chloroform. RNA in the aqueous phase was precipitated with isopropanol, washed with 75% ethanol, and dissolved in RNase-free water. Reverse transcription of RNA (0.4 μg) was carried out using ReverTra Ace qPCR RT Master Mix with gDNA Remover (Toyoba, FSQ-301, Osaka, Japan) according to the manufacturer's protocol. Quantitative RT-PCR reactions were performed using 20 ng of cDNA incubated with 410 nM of each primer and 6 μL of SYBR Green PCR Master mix (Toyoba, Osaka, Japan THUNDERBIRD SYBR qPCR Mix QPS-201) in a total volume of 12 μl. The PCR reaction (95° C. for 1 minute followed by 45 cycles of 95° C. for 10 s, 60° C. for 40 s) was carried out on a Roche LC480 system (Basel, Switzerland). Relative mRNA levels were calculated by the comparative threshold cycle method using cyclophilin as an internal control. Primer sequences can be found in STable 6. The kidneys not used for RNA extraction were fixed in 10% formalin, processed to make standard paraffin sections, and stained with Picro-Sirius Red to detect collagen as red fibers. The collagen volume fraction (the ratio of the Sirius Red-positive area to the total area) was quantified using an image analysis software (IMAGE PRO 9.32, Medica Cybernetics, Rockville, Md., USA) as previously described (Hirano, Y. Kurosu et al., *FEBS Open Bio.* 10, 894-903. DOI:10.1002/2211-5463.1284, 2020). The cortex and the cortico-medullary junction were evaluated separately. All animal experiments were approved by the institutional animal care and use committee from Jichi Medical University.

Data Analysis

All images were analysed and graphs prepared using Python 3, except pre-screening in solution experiments and preliminary cell adhesion data were analysed using Matlab and plotted using GraphPad Prism (GraphPad, La Jolla, Calif., USA). RNA sequencing data was analysed as described in the above section and graphs prepared using R software and GraphPad Prism. Animal data were analysed in GraphPad Prism.

Results

Calcification Assay

The inventors performed an in vitro assay that measures the propensity for calcification of human serum and has been clinically validated as a predictor of all-cause mortality in CKD patients and renal transplant recipients (as described in Pasch, Journal of the American Society of Nephrology 23, 1744-1752, 2012). The experiment was carried out by mixing a calcium solution, human pooled serum, the test compound at the final concentration indicated and a phosphate solution, and the transition time of primary to secondary CPPs was measured at 37° C. using a nephelometer for up to 600 minutes.

The data of FIG. 1 show that the compounds IP2S4 and IT2S4 are more active than IP6. Furthermore, compound 2-PEG-IP5 is far more active than any other compound in this assay. This result suggests a key role of the polymer moiety in preventing the transition of primary to secondary CPPs and in reducing the propensity for calcification of human serum.

The data of FIG. 2 show that the compounds INS-2031 (III p), INS-3001 (IV f) and INS-3031 (IV g) are more active than IP6. The compounds having two PEG moieties (INS-3001, INS-3031) are more active than the compounds having one PEG moiety (INS-2031). This result suggests a key role of the polymer moiety in preventing the transition of primary to secondary CPPs and in reducing the propensity for calcification of human serum.

Example 1: Image-Based Profiling of Calcification Processes

Figure 3:
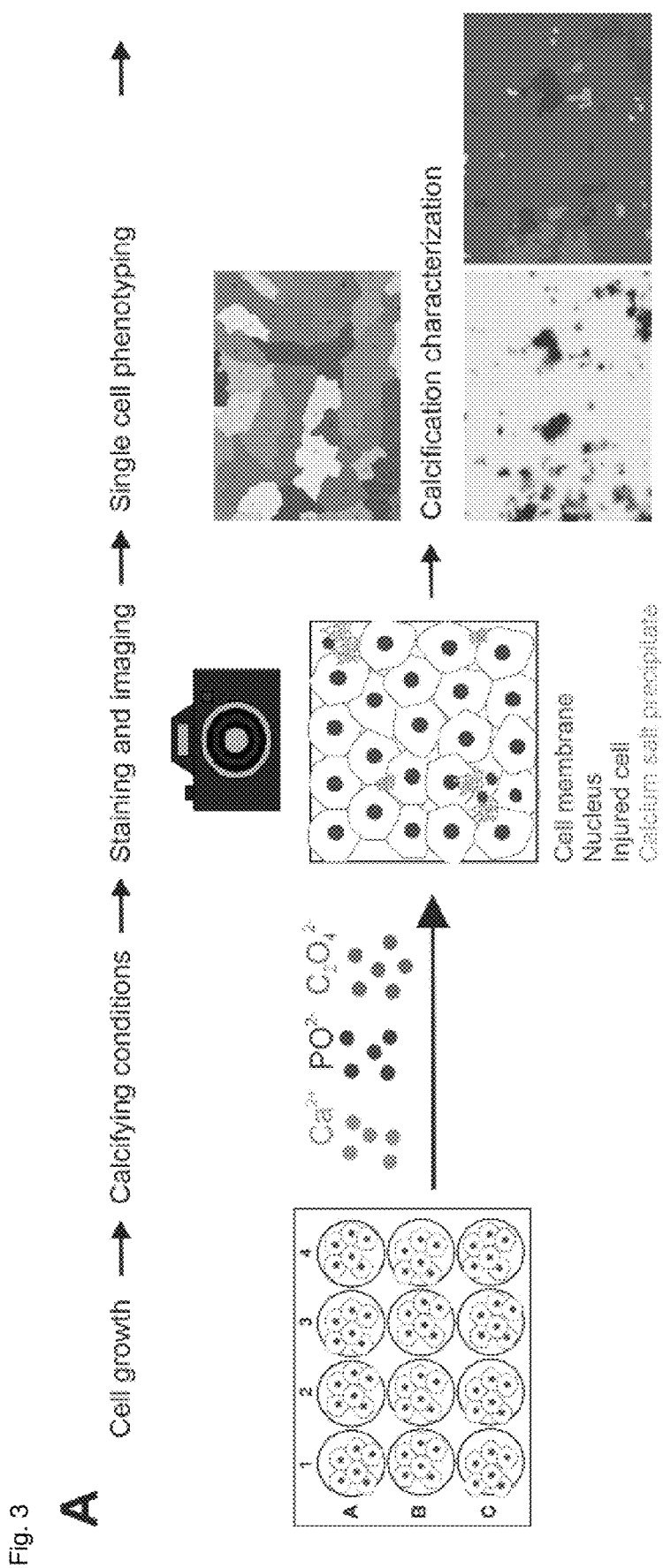
FIG. 3 shows an overview of the developed calcification profiling platform. (A) Outline of the workflow. (B) Overview of the output of the analytical pipeline. Example images of brightfield (column 1), CellMask (column 2), Hoechst (column 4) and calcein (column 6) stainings and two zoomed-in regions of interests (ROI) of RPTEC cells treated with 5/7 mM Ca/P are shown. CellMask and Hoechst channel images were used for single cell segmentation. Hoechst local maxima (indicated in dark blue, column 4) and the CellMask binary image served as seeds and input image, respectively, for the watershed algorithm. Comparison of the final cell segmentation in blue overlayed with the CellMask binary image in red is shown in column 3. The final segmentation and the Hoechst seeds are shown in column 5. Binary images of the calcein channel were generated by adaptive thresholding. Individual labelled CaP regions are shown in column 7.
Figure 3:
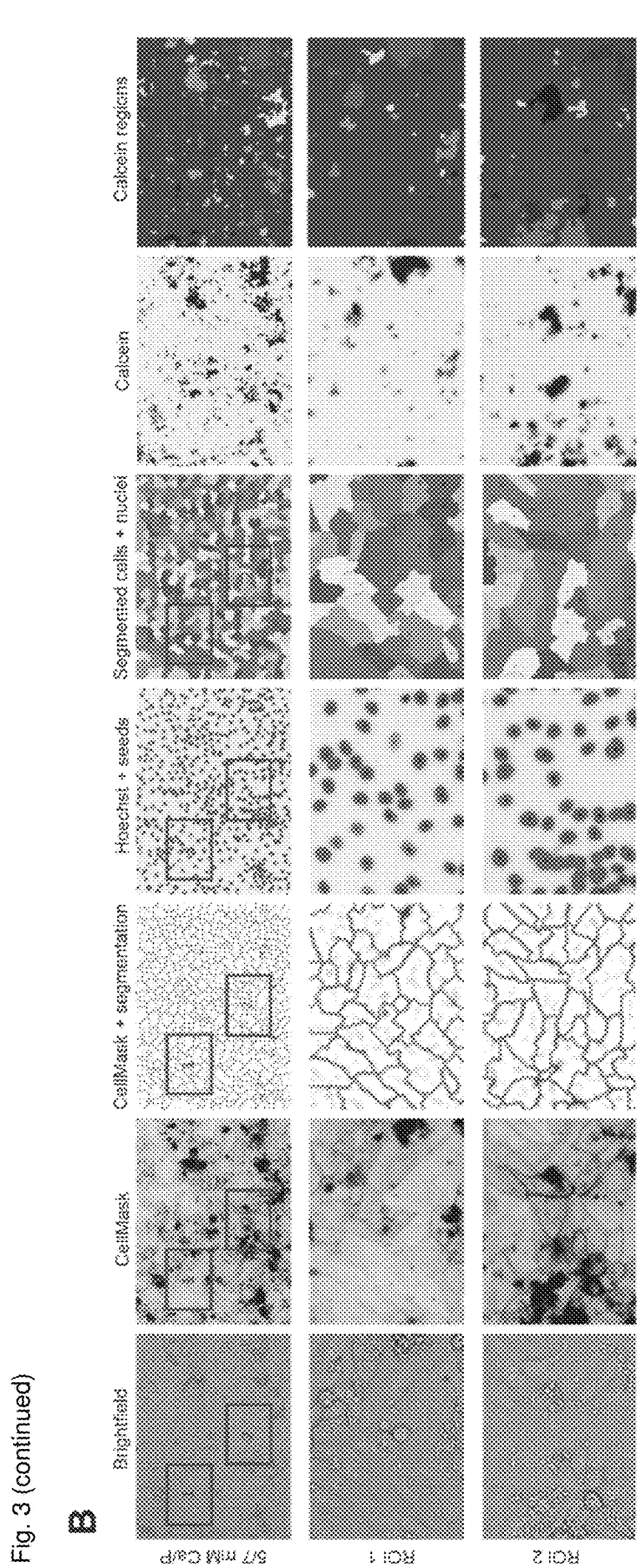

To allow rapid profiling of molecules for their effects on diverse kidney calcification processes, the inventors developed a cell-based assay that allowed the monitoring of CaP deposition, as well as cellular changes associated with it. Therefore, the inventors utilized monolayers of renal proximal tubular cells (RPTEC) stained with various dyes to quantify calcification and cell morphology changes (FIG. 3). Cells grown in monolayer were exposed to varying ionic conditions found within the renal tubules, e.g. increased calcium and/or phosphate, to trigger the crystallization of CaP and cellular attachment (FIG. 3A). CaP deposits were detected via calcein staining (FIG. 3B). Calcein has been previously suggested as a calcium staining technique of fixed or unfixed cell samples. The fluorescent dye binds to calcium and is imaged using fluorescent microscopy. Further, the inventors tested the induction of CaP-induced CaOx crystallization, which is characteristic for idiopathic kidney stone formation. It was observed that by first inducing CaP deposition, followed by addition of high oxalate, CaOx crystallization can be found on CaP deposits. CaOx crystals displayed a strong contrast and a typical twinned structure.

Cellular changes were visualized by staining for the membrane with a CellMask dye. Hoechst was used as a nuclear dye, to aid in single cell segmentation, and ethidium-homodimer 1 (EthD) facilitated the staining of cells with a damaged plasma membrane (FIG. 3B). Further, texture features of both the CellMask and calcein channel were extracted, which were indicative of CaP deposition patterns (i.e., large and high intensity CaP clusters vs. more diffuse and equally spread CaP across the cell monolayer) (FIG. 3B).

Example 2: CaP-Induced Changes on Renal Epithelial Cells

Figure 4:
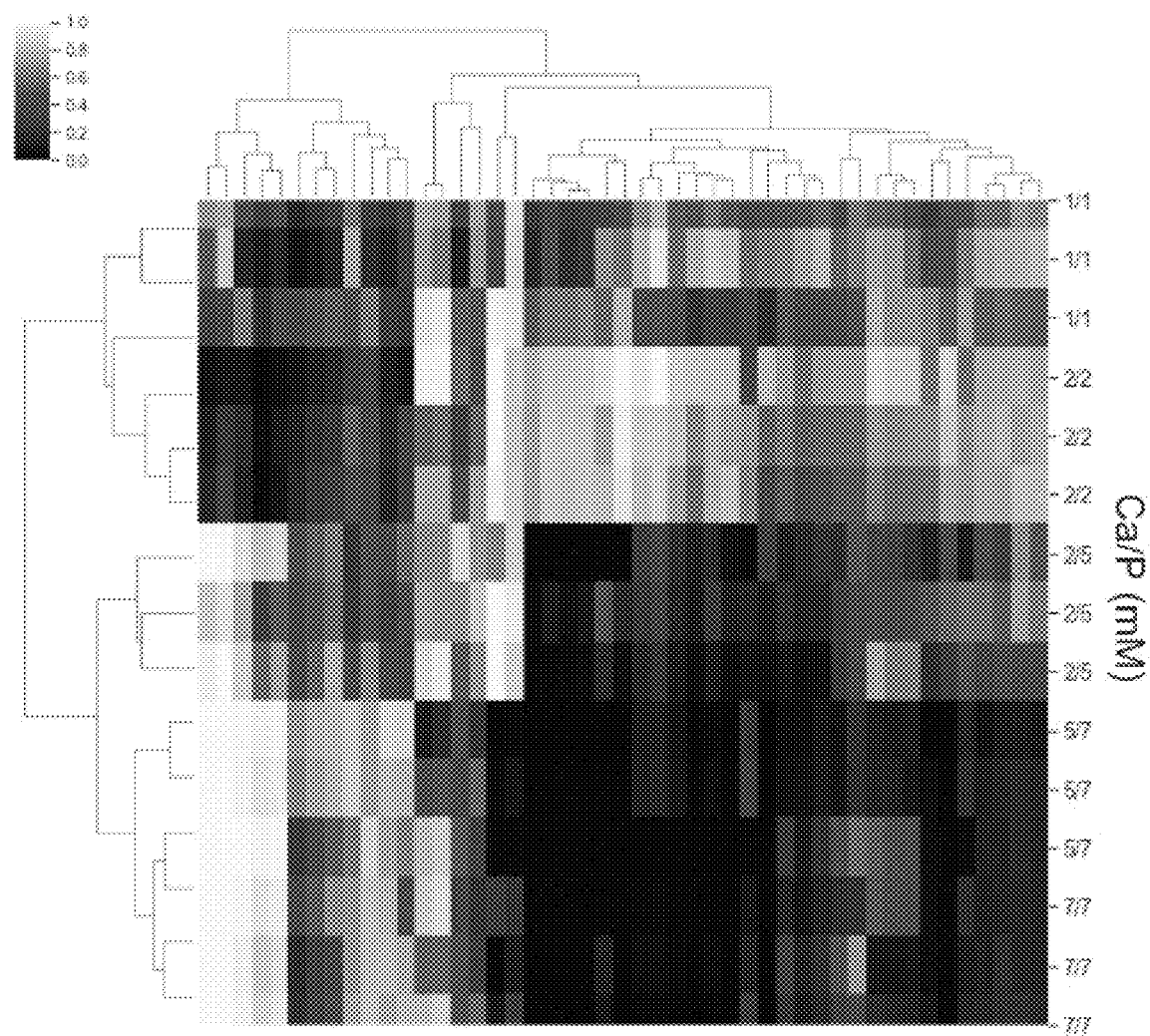
FIG. 4 shows effects of increasing concentrations of Ca/P on RPTEC in vitro. (A) Heatmap and hierarchial clustering of the Ca/P treatment conditions and extracted image features. (B) Selected single features describing cellular changes upon increasing Ca/P concentrations are depicted. Total cell count, dead cell count, single cell area and single cell solidity, a measure of cell compactness, are shown. (C) Selected single features describing changes in the CaP deposition and membrane pattern upon increasing Ca/P concentrations are depicted. The total area of the binary calcein staining, colorimetric quantification of calcium content extracted from the monolayer, the maximum intensity of the calcein fluorescence, structural similarity index metric (SSIM) and the correlation of the CellMask channel image are shown. (D) Example brightfield, calcein, CellMask and EthD channel images and two zoomed-in regions of interests (ROI) of RPTEC treated with 2/5 mM Ca/P are represented. Mean scaled values per individual experiment are plotted in colored circles, except for total calcium quantification absolute values per individual experiment were used (N=3). Mean of three individual experiments and SD is plotted as grey horizontal and vertical line respectively, one-way ANOVA with Dunnet's multiple comparison between each concentration to 1/1 mM Ca/P was performed (*$p<0.01$).
Figure 4:
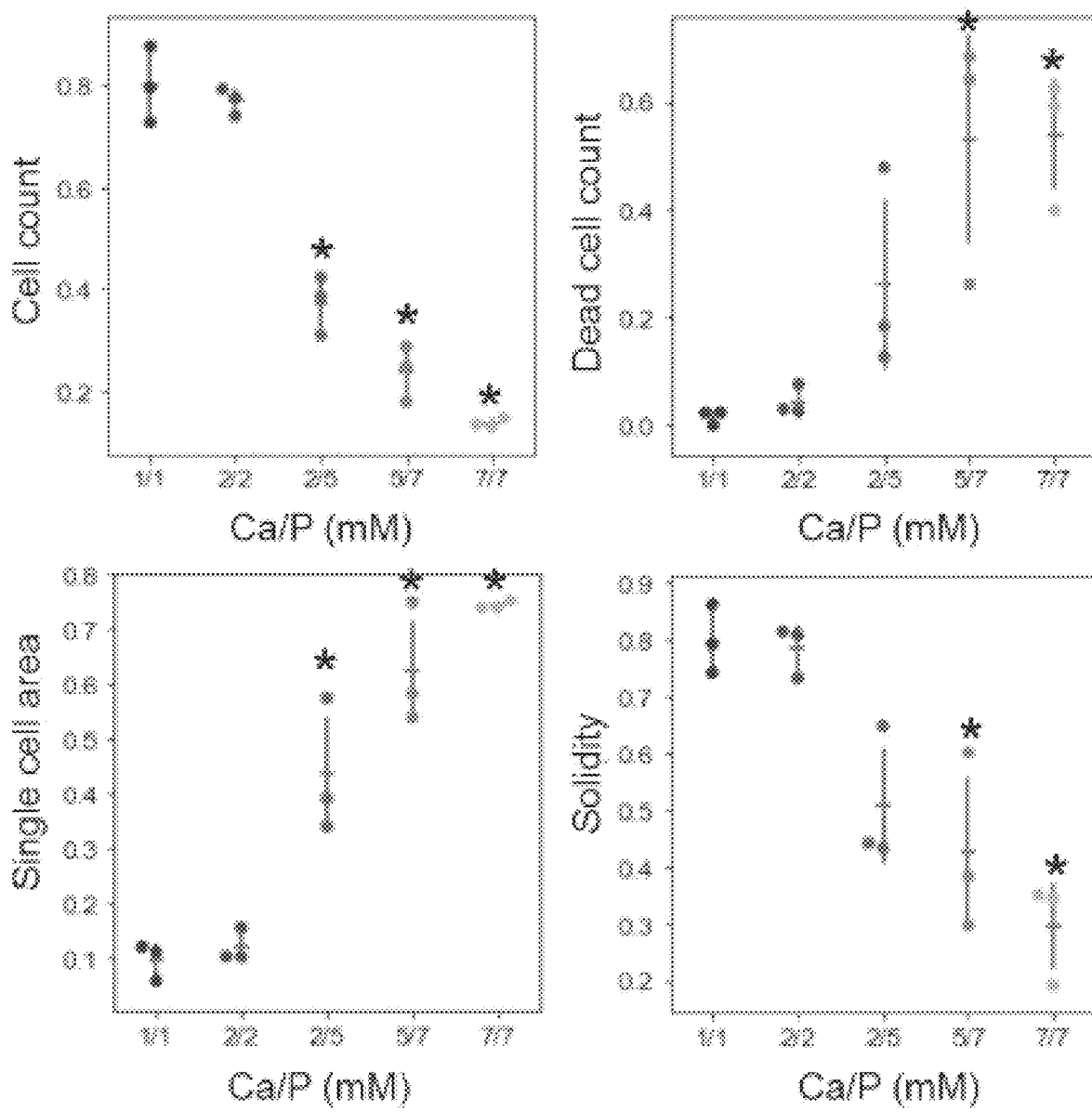
Figure 4:
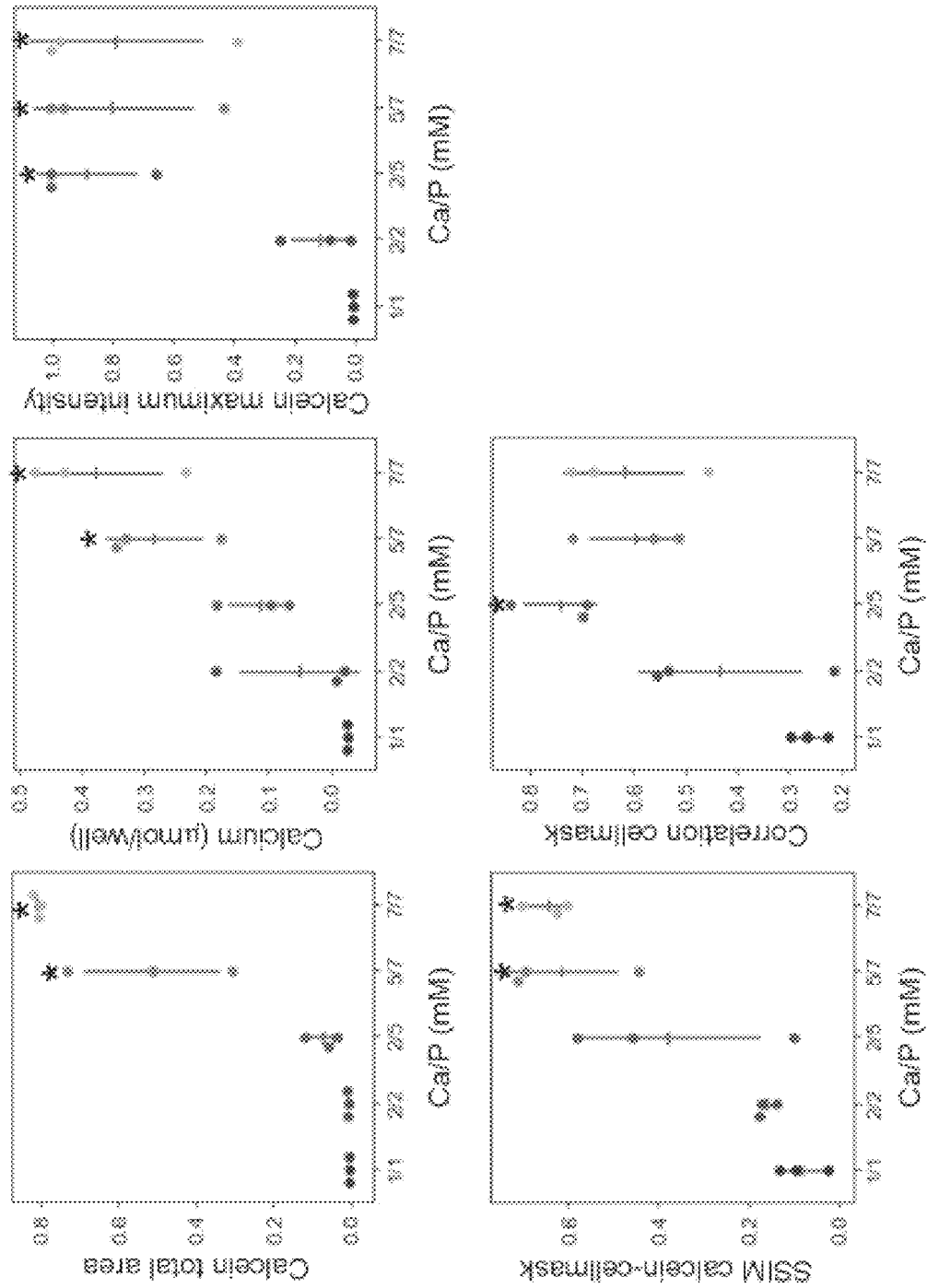
Figure 4:
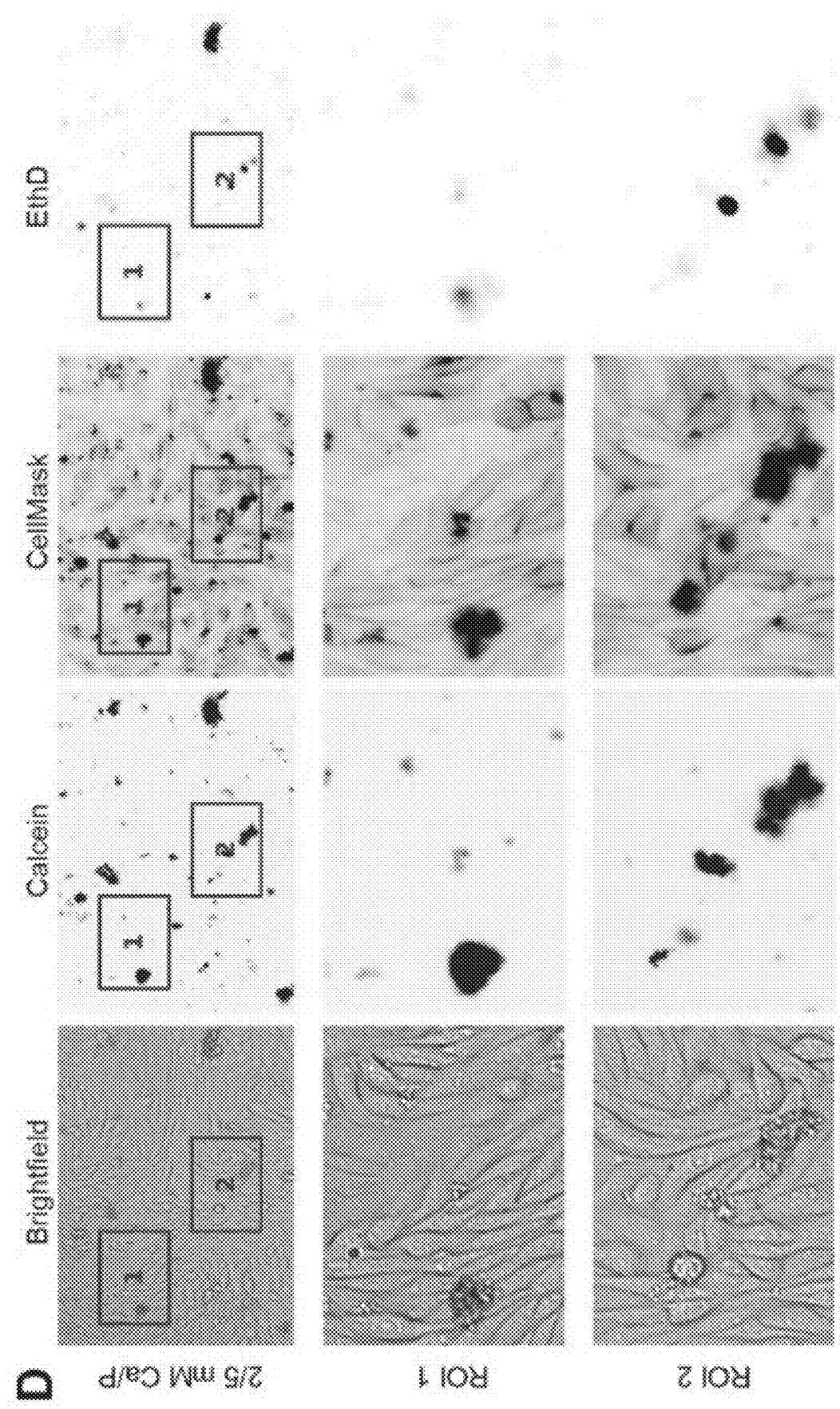

The inventors first investigated the effects of increasing calcium and phosphate concentrations on cellular CaP deposition and the ensuing cellular changes. Features extracted included single cell shape and fluorescence intensity parameters, texture features of both the CellMask and calcein images, and CaP deposit shape and intensity features. Hierarchical clustering of experimental conditions and features showed a clear dose-dependent trend (FIG. 4A). Low concentrations of calcium and phosphate, such as those of non-spiked cell media (1/1 mM Ca/P) and low spiked one (2/2 mM Ca/P) did not induce cellular changes, while higher levels resulted in intermittent (2/5 mM) and drastic changes (5/7 and 7/7 mM) (FIG. 4B). Cellular changes associated with Ca/P levels became more evident when looking at single parameters. Increasing Ca/P led to loss of tight packing of cells, characteristic for the renal epithelium, which is associated with an increase in single cell area and a decrease in single cell solidity, a measure for compactness. Hence, these data indicated the loss of the typical round shape of the epithelial cells towards a more irregular shape (FIG. 4B). These effects were accompanied by a decrease in the total number of cells/field of view. Additionally, an increase in cells with a damaged plasma membrane was detected with increasing Ca/P levels (FIG. 4B). These results are in agreement with literature reports, which suggest a loss of epithelial phenotype and cell injury upon stimulation with CaP or CaOx.

Levels of CaP deposition were measured first by, adaptive thresholding of the calcein image, and second, quantification of the total area covered per field of view. Using this approach, the inventors found an increased coverage of the cell monolayer with CaP upon higher Ca/P concentrations (FIG. 4C). These results were qualitatively validated by comparison with brightfield images, where CaP is visible as a feature with a granular texture, or, in the case of large deposits, as dark spots (FIG. 4D). Calcein quantification of CaP deposition was confirmed by employing a colorimetric quantification of calcium, which was extracted from the cell monolayer by acid treatment (FIG. 4C) (Schantl, A. E. et al., Nat. Commun. 11, 721. DOI: 10.1038/s41467-019-14091-4, 2020). Interestingly, while treatment with 2/5 mM Ca/P did not lead to a great enhancement of area of CaP depositions, the deposits were of high calcein intensity (FIG. 4C, D). Thus, the inventors hypothesized that rather than equally distributing across the monolayer, at lower concentrations, CaP tends to accumulate at sites of enhanced CaP affinity, such as dedifferentiating or injured cells with increased surface expression of glycoproteins with calcium binding properties. These findings were supported by a high structural similarity index metric (SSIM) of the calcein and CellMask channel image, indicating the overlap of areas of CaP deposition with membrane staining, upon intermediate and high Ca/P stimulation (FIG. 4C). The overlapping areas showed a high intensity of membrane staining, which could indicate clumps of cell debris of injured and detaching cells. Additionally, the correlation texture feature of the CellMask channel image, reflecting consistency of an image, showed an increase between 1/1 to 2/5 mM Ca/P spiking, before a drop occurred again at ≥5/7 mM Ca/P (FIG. 4C). The highest value observed for the intermediate Ca/P concentration might be due to the loss of cell outlines when Ca/P is present but no large CaP cluster sites were formed. At high concentrations, CaP sites again caused a decrease in the correlation feature due to CaP-membrane clusters giving high staining intensities. For the further testing of inhibitors, concentrations of 5/7 mM Ca/P were used, which are within the physiological range in the loop of Henle, the suggested main site of CaP crystallization.

Figure 5:
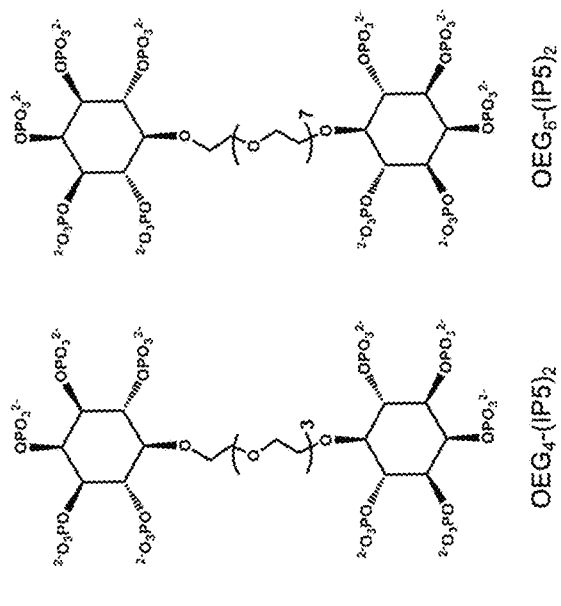
FIG. 5 shows an overview of IP6 analogues tested in solution.
Figure 5:
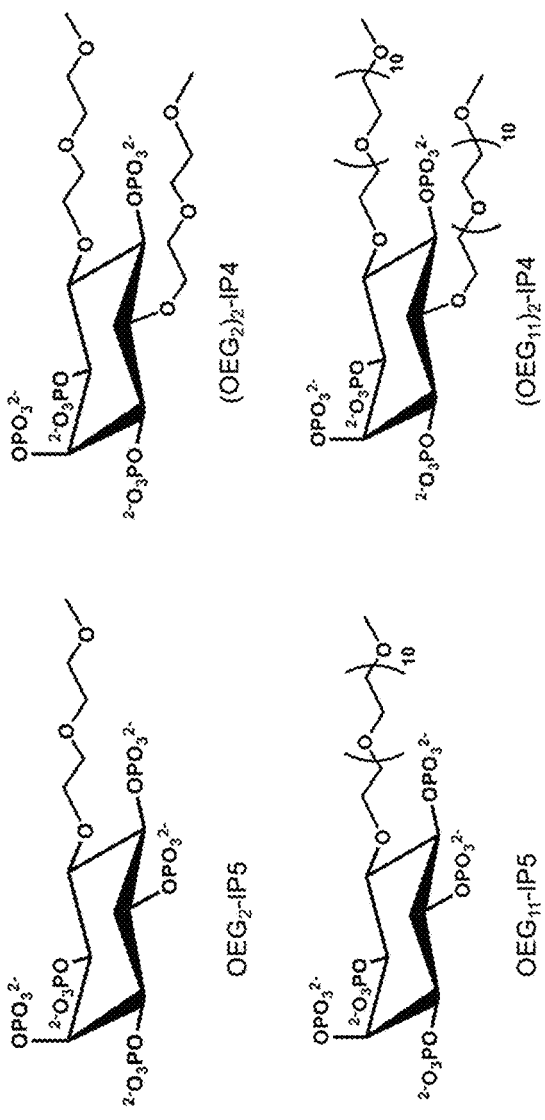
Figure 5:
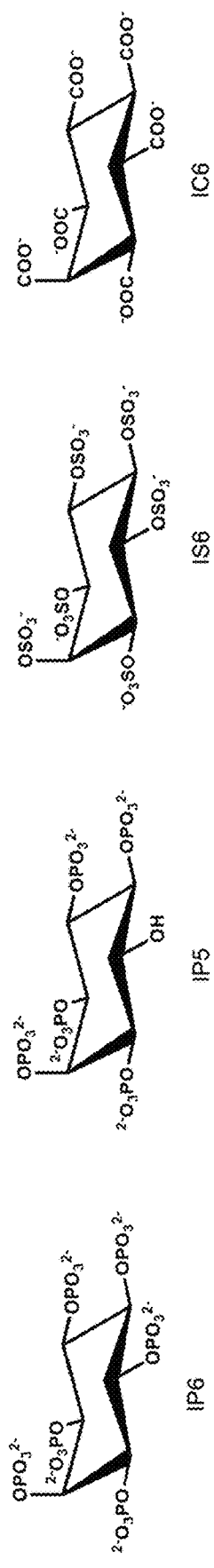

Example 3: Pre-Screening of IP6 Analogues as Renal CaP Inhibitors in Solution In a first step, the influence of selected IP6 analogues (FIG. 5) on CaP precipitation and growth was assessed in vitro using artificial renal tubular fluid (RTF) (Table 1). In a previous study, the inventors investigated CaP protein particle formation in serum. However, an important difference to cardiovascular calcification lies in the extremely low protein content of the renal tubular fluid vs. the high abundance of proteins in blood, which can stabilize amorphous particles. Two cut-offs were chosen for assessing efficacy. First, complete inhibition was defined as a >90% reduction of detected CaP precipitates compared to the control sample without compound. Second, inhibition of CaP aggregation was defined as a >50% reduction of the mean size of aggregates when compared to the control.

Figure 10:
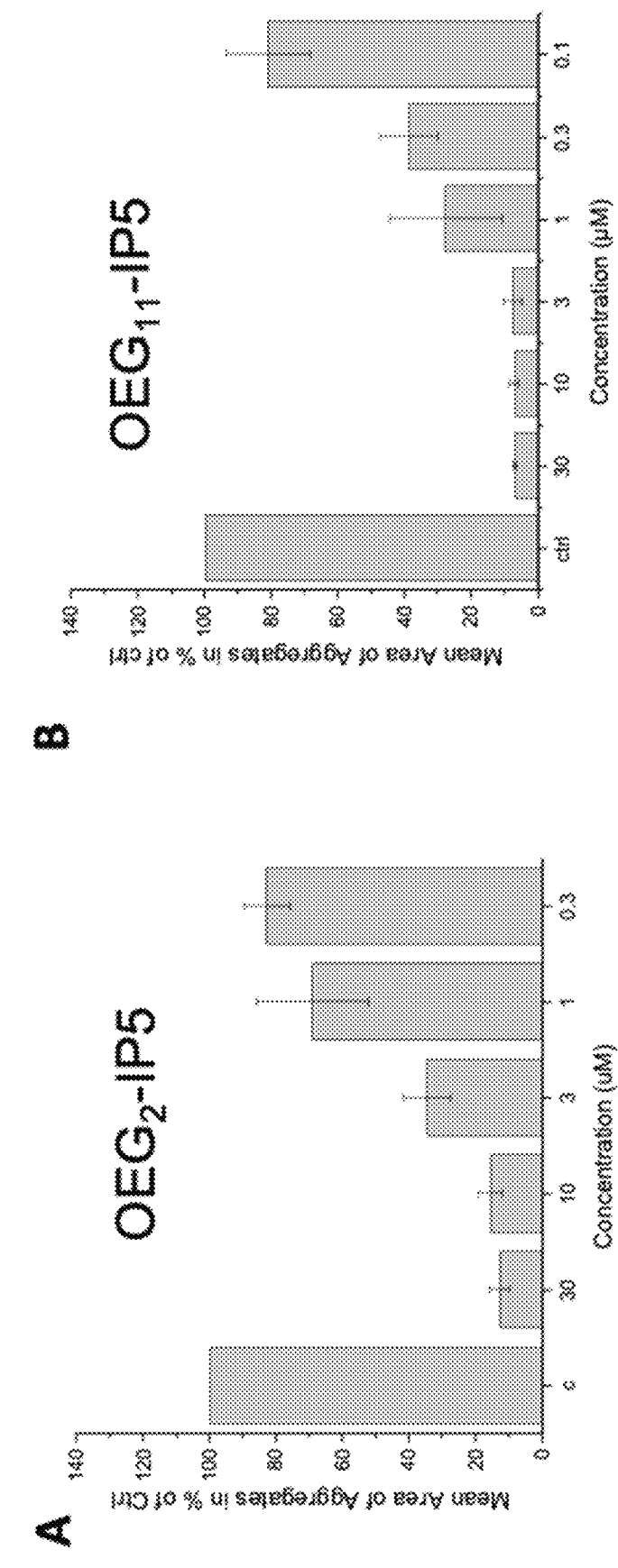
FIG. 10 shows inhibition of CaP aggregation with $OEG_2$-IP5, $OEG_{11}$-IP5, $(OEG_2)_2$-IP4, $(OEG_{11})_2$-IP4 and $OEG_8$-$(IP5)_2$. Effects of (A) $OEG_2$-IP5, (B) $OEG_{11}$-IP5, (C) $(OEG_2)_2$-IP4, (D) $(OEG_{11})_2$-IP4 and (E) $OEG_8$-$(IP5)_2$. on CaP precipitation in RTF spiked with 9 mM disodium phosphate and 8 mM calcium chloride were assessed by light microscopy followed by automated image analysis at t=4 h. Quantification of the mean size of aggregates/field of view normalized to the ctrl (N=3, mean+SD, normalized to the control).
Figure 10:
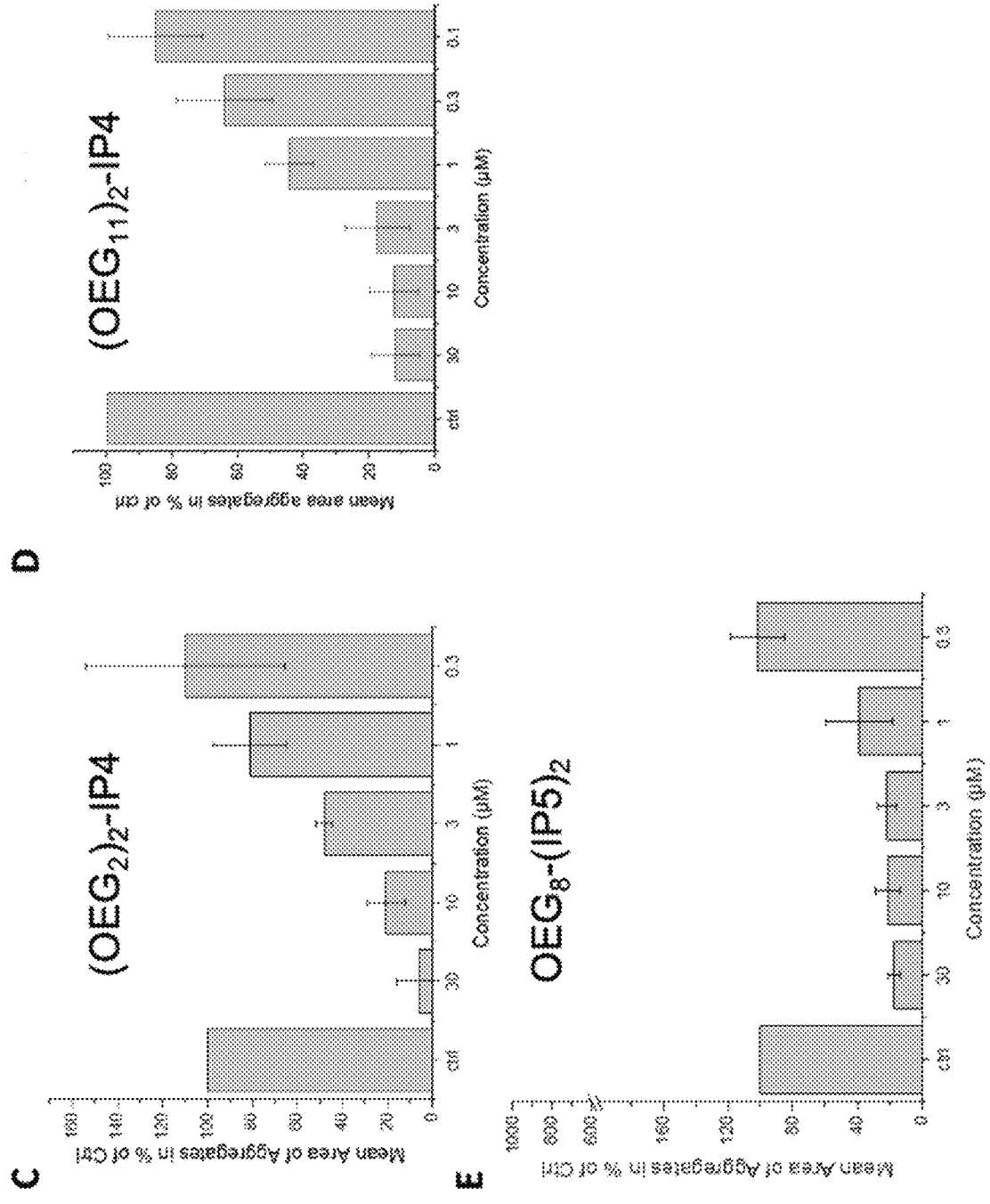

Interestingly, IP6, and to a lesser extent myo-inositol pentakisphosphate (IP5), promoted CaP precipitation at 10 and 30 µM, respectively. CaP precipitation was likely accelerated by IP6-calcium aggregates forming, as the inventors confirmed in media without phosphate. Replacing phosphate groups with oligoethylene glycol (OEG) chains, as in the case of $OEG_2$-IP5, led to inhibition of CaP precipitation and aggregation at 30 and 1 µM, respectively (Table 1, FIGS. 10A and 11A). Comparing $OEG_2$-IP5 and $OEG_{11}$-IP5 revealed that increasing the length of the OEG chain from 2 to 11 repeating units improved the molecule's inhibitory properties, reducing its aggregation inhibitory concentration from 1 µM to 300 nM (Table 1, FIGS. 10B and 11B). However, further phosphate substitution with OEG (($OEG_2)_2$-IP4 vs. $OEG_2$-IP5) did not further increase the inhibitory activity (Table 1, FIGS. 10C and 11C). The substitution of phosphate groups with less charged sulphate and carboxyl groups, e.g myo-inositol hexasulfate (IS6) and cyclohexane hexacarboxylic acid (IC6), led to a loss of the promoting effect. These compounds only exhibited weak inhibitory properties on CaP crystallization (Table 1).

Divalent IP5 molecules, which in a previous study have been identified as potent inhibitors of renal CaOx crystallization, revealed another interesting trend. The effect on crystallization depended on the length of the linker between the IP5 moieties. $OEG_4$-$(IP5)_2$, with 4 EG units in the linker, promoted CaP precipitation, while $OEG_8$-$(IP5)_2$ having 8 EG repeating units, had an inhibitory effect. Complete inhibition was observed at 30 µM and 50% aggregation inhibition obtained at 1 µM (Table 1, FIG. 10E, 11E). Together, these findings suggest that CaP inhibition by IP6 analogues in a medium completely devoid of protein is highly dependent on the molecules' charge and stabilizing properties.

Figure 11:
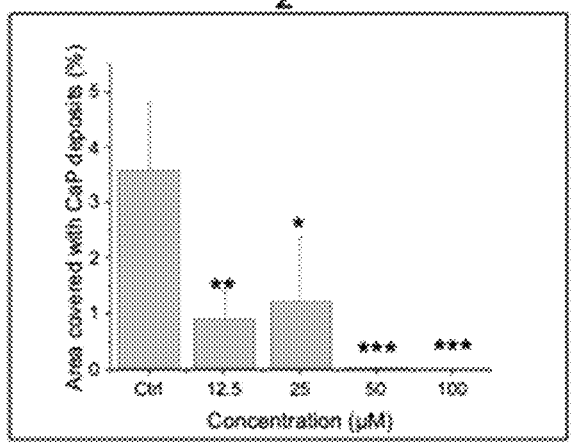
FIG. 11 shows in vitro reduction of CaP adhesion and prevention of cell injury by IP6 analogues. RPTEC/TERT 1 monolayers at confluence were treated with medium spiked with 7 mM disodium phosphate, 5 mM calcium chloride and compound and were incubated for 24 h. The amount of CaP deposits and the extent of cell injury were detected by calcein and EthD staining, respectively. Fluorescence images were quantified using Matlab. Quantification of the area covered with CaP deposition on RPTEC monolayers with (A) $OEG_2$-IP5, (B) $OEG_{11}$-IP5, (C) $(OEG_2)_2$-IP4, and (D) $OEG_8$-$(IP5)_2$ treatment. (N=3, mean+SD, one-way ANOVA with Dunnett's multiple comparison, *p<0.05, p<0.01, *p<0.001).
Figure 11:
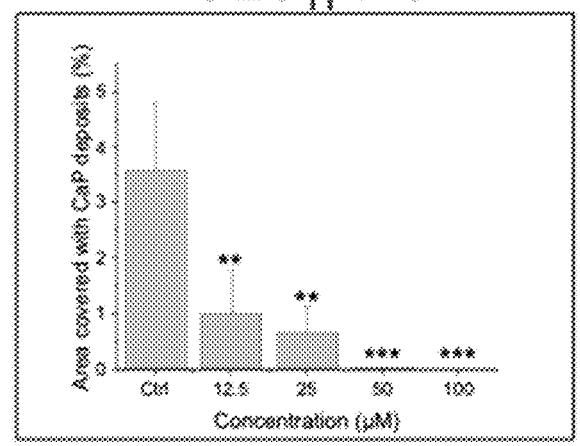
Figure 11:
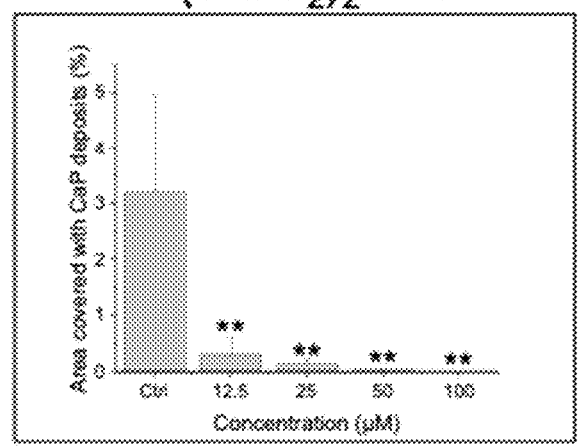
Figure 11:
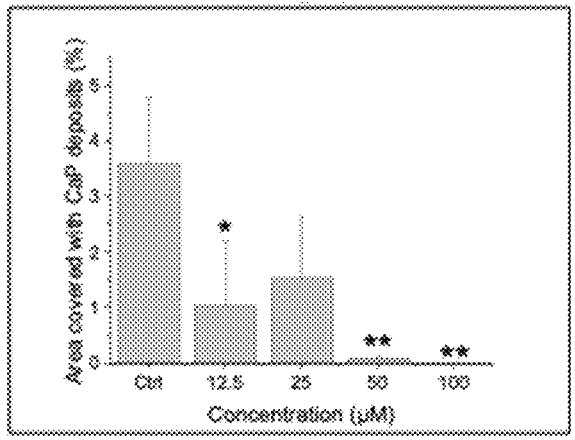

Example 4: $(OEG2)_2$-IP4 Prevents CaP Deposition and Cellular Changes In Vitro In the next step, the inventors compared $OEG_2$-IP5, $OEG_{11}$-IP5, $(OEG_2)_2$-IP4 and $OEG_8$-$(IP5)_2$ on their efficacy to prevent CaP adhesion (FIG. 11). Cell medium was spiked with compound before the addition of phosphate and calcium. Herein, efficacy was in a similar range for all compounds, achieving complete inhibition of CaP adhesion at 50 µM. Interestingly, $(OEG_2)_2$-IP4 performed best, drastically reducing CaP adhesion down to 12.5 µM, which together with its reported favorable pharmacokinetic profile (Schantl, A. E. et al., *Nat. Commun.* 11, 721. DOI: 10.1038/s41467-019-14091-4, 2020), led the inventors to further characterize this compound.

Figure 6:
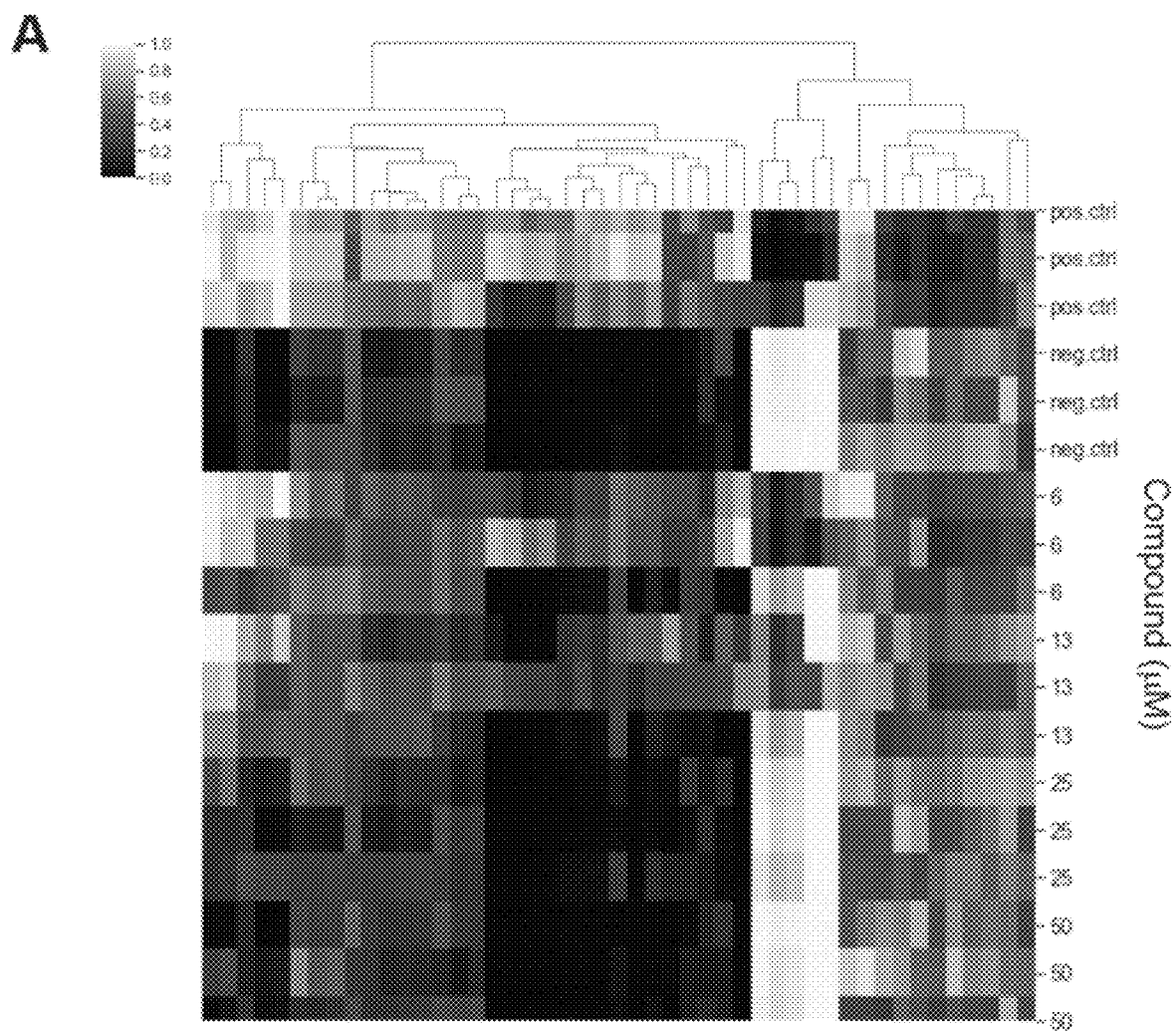
FIG. 6 shows inhibitory properties of $(OEG_2)_2$-IP4 on Ca/P induced changes of RPTEC in vitro. (A) Heatmap and hierarchical clustering of extracted image features. (B) Selected single features describing cellular changes upon increasing $(OEG_2)_2$-IP4 concentrations are depicted. Total cell count, dead cell count, single cell area and single cell solidity, a measure of cell compactness, are shown. (C) Selected single features describing changes in the CaP deposition and membrane pattern upon increasing $(OEG_2)_2$-IP4 concentrations are depicted. The total area of the binary calcein staining, colorimetric quantification of calcium content extracted from the monolayer, the maximum intensity of the calcein fluorescence, structural similarity index metric (SSIM) and the correlation of the CellMask channel image are shown. (D) Example brightfield, calcein, CellMask and EthD channel images and two zoomed-in regions of interests (ROI) of RPTEC treated with 13 µM $(OEG_2)_2$-IP4 are shown. Mean scaled values per individual experiment are plotted (N=3). Pos.ctrl presents treatment with 5/7 mM Ca/P, neg.ctrl presents medium without Ca/P spiking (=1/1 mM Ca/P present in normal cell medium). Mean of three individual experiments and SD is plotted as grey horizontal and vertical line respectively, one-way ANOVA with Dunnet's multiple comparison between each concentration to pos. ctrl was performed (*$p<0.01$).
Figure 6:
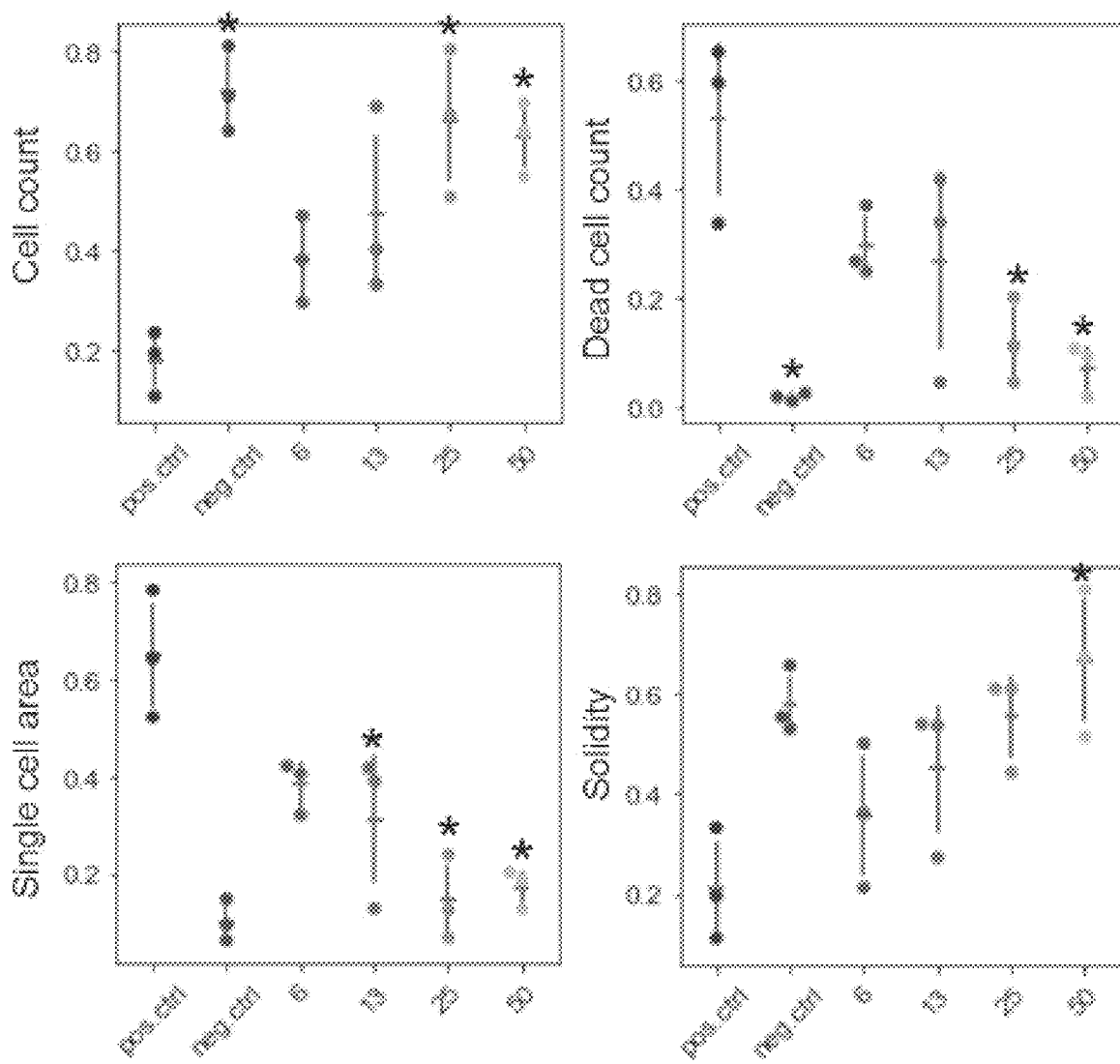
Figure 6:
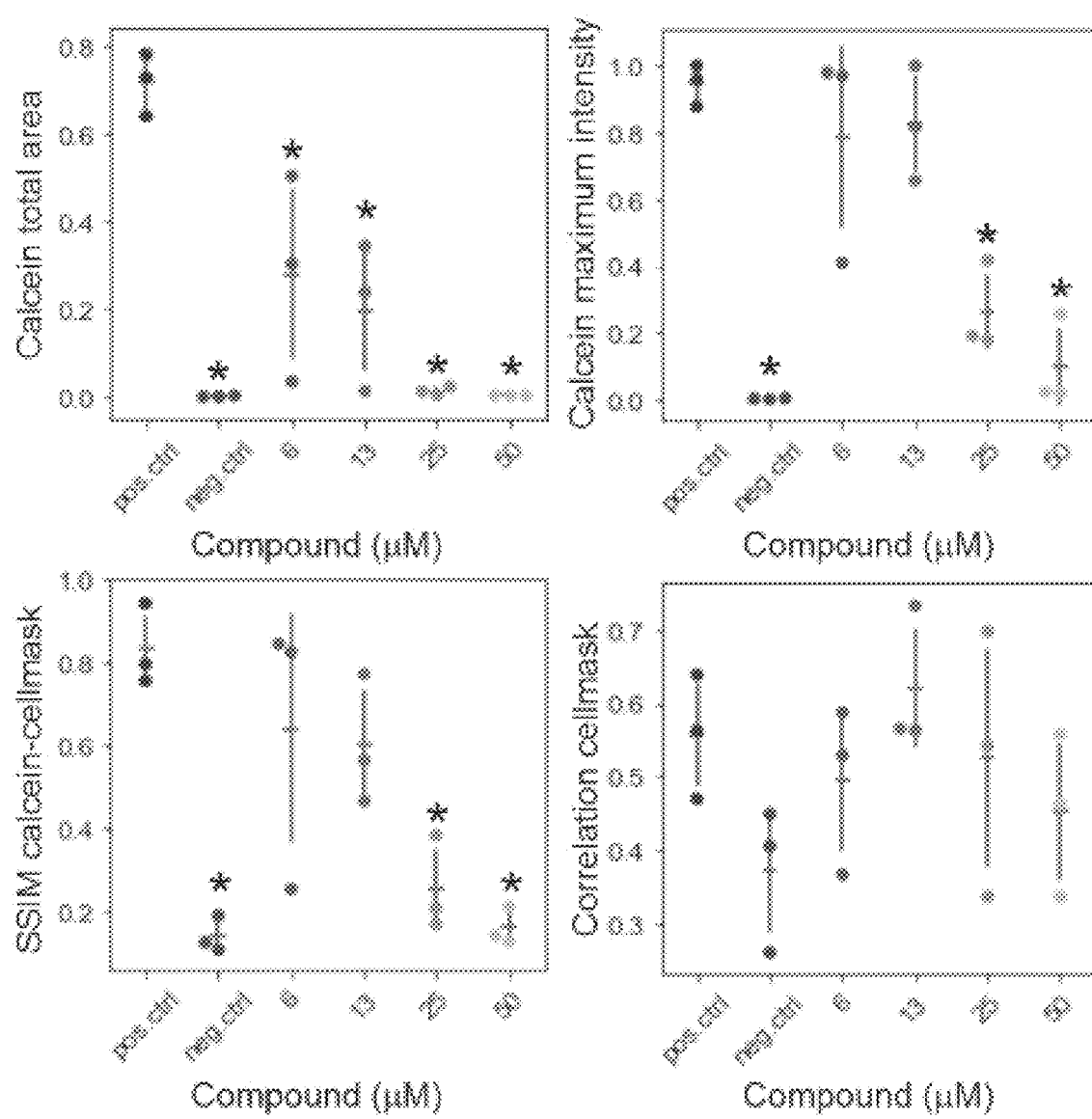
Figure 6:
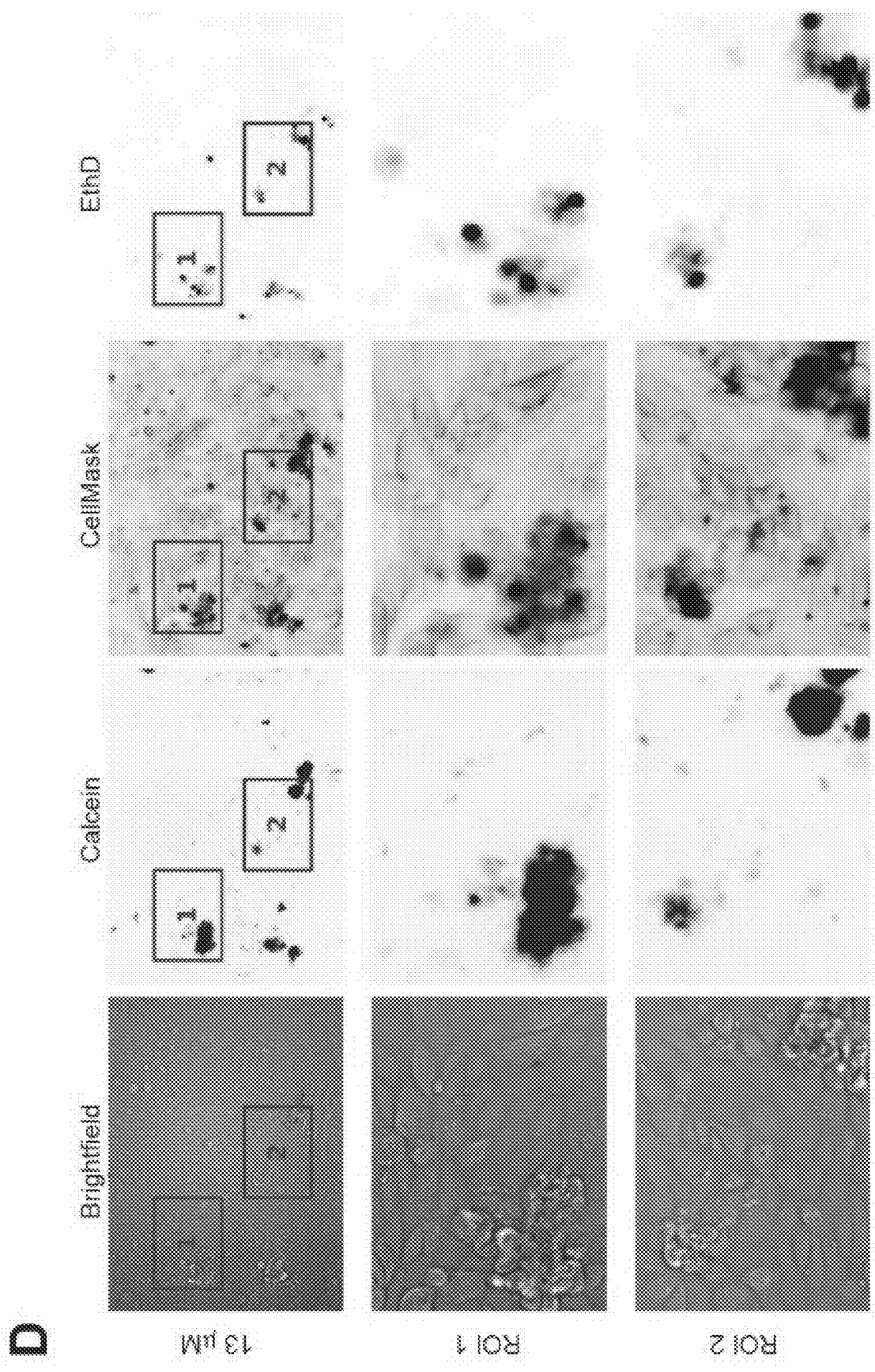

Treatment of cells with 6-50 µM of $(OEG_2)_2$-IP4 resulted in a dose-dependent reversal of the image feature profile from the positive control (ctrl) (+5/7 mM Ca/P) towards the negative ctrl (+1/1 mM Ca/P) (FIG. 6A). $(OEG_2)_2$-IP4 dose-dependently reduced the number of dead cells and single cell area compared to the positive ctrl, and increased single cell solidity and total cell count/field of view (FIG. 6B). Hence, these data suggest a reversal towards the negative ctrl phenotype with $(OEG_2)_2$-IP4.

Figure 12:
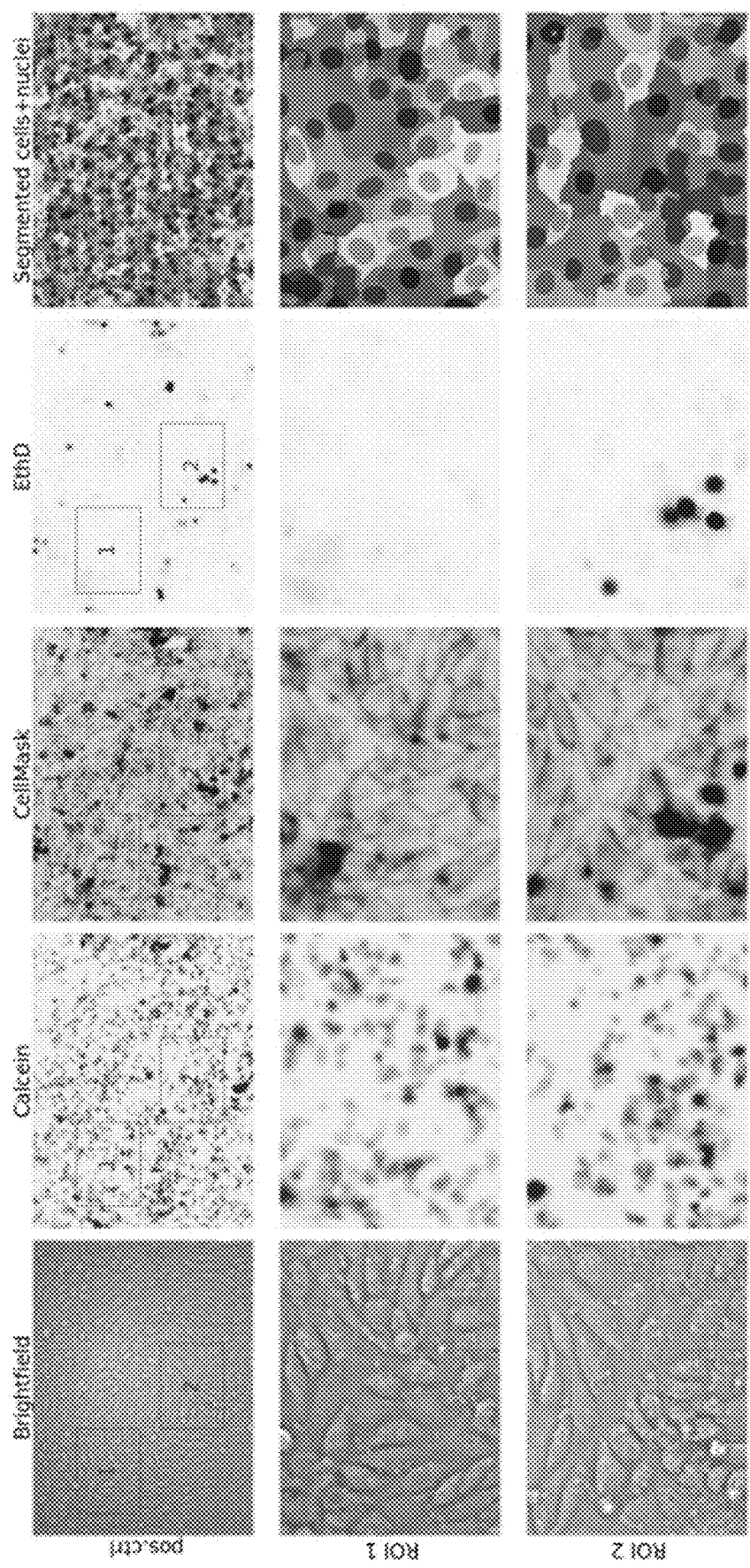
FIG. 12 shows example images of RPTEC treated with 5/7 mM Ca/P and increasing concentrations of $(OEG_2)_2$-IP4. Brightfield, calcein, CellMask™ and EthD channel images and two zoomed-in regions of interests (ROI) are shown (column 1-4). Cell segmentation is shown overlayed with the Hoechst channel image (blue) (column 4). Pos.ctrl presents treatment with 5/7 mM Ca/P, neg.ctrl presents medium without Ca/P spiking (=1/1 mM Ca/P present in normal cell medium).
Figure 12:
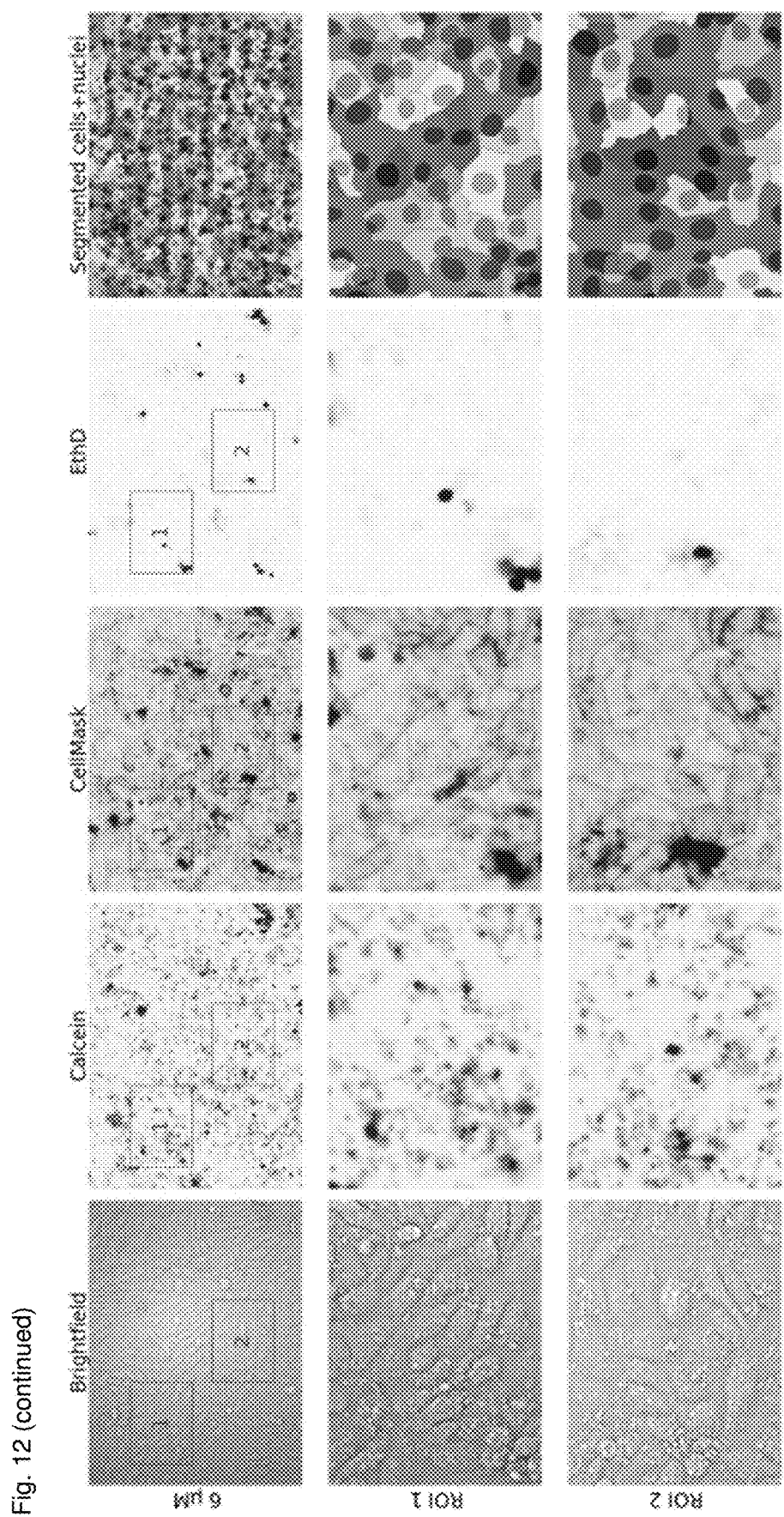
Figure 12:
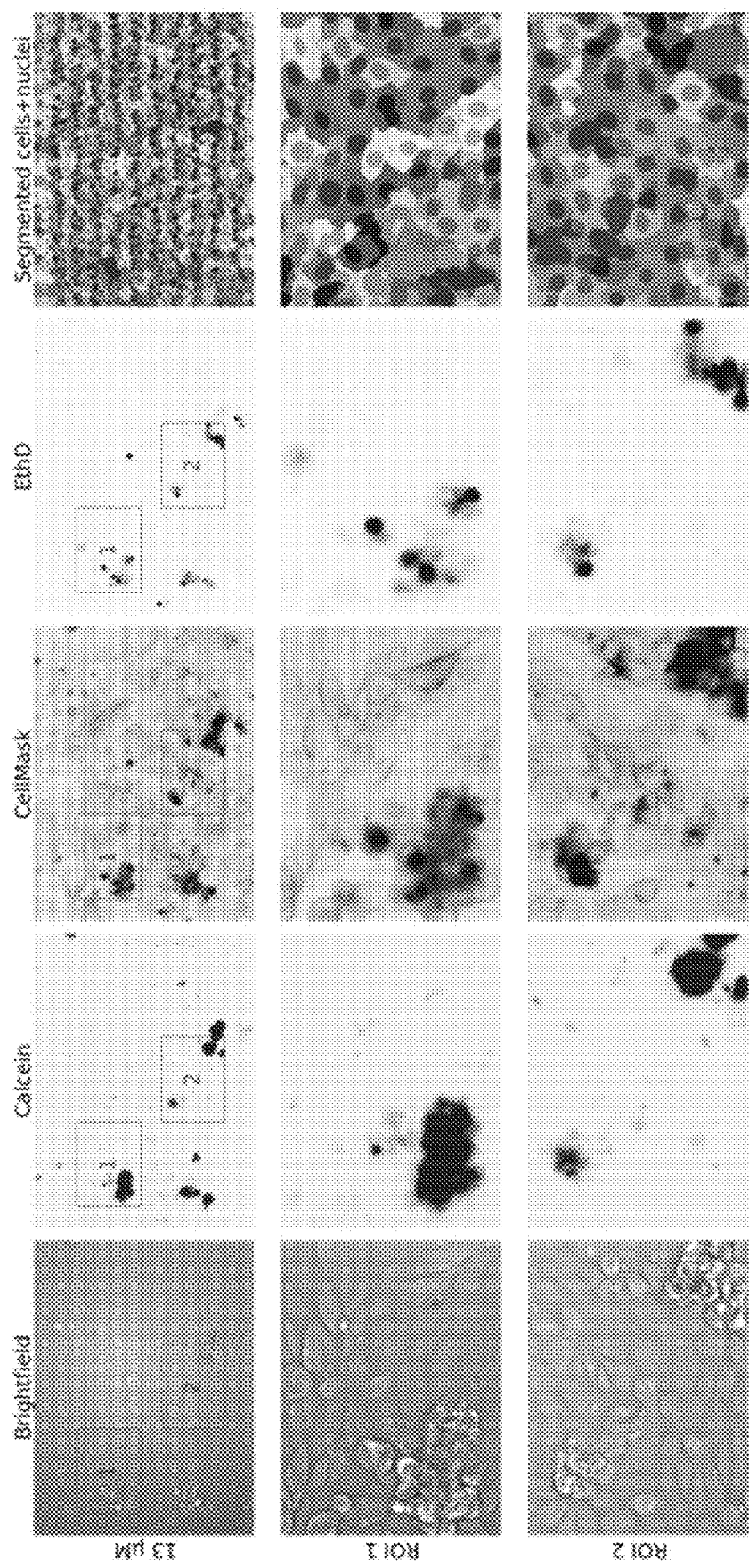
Figure 12:
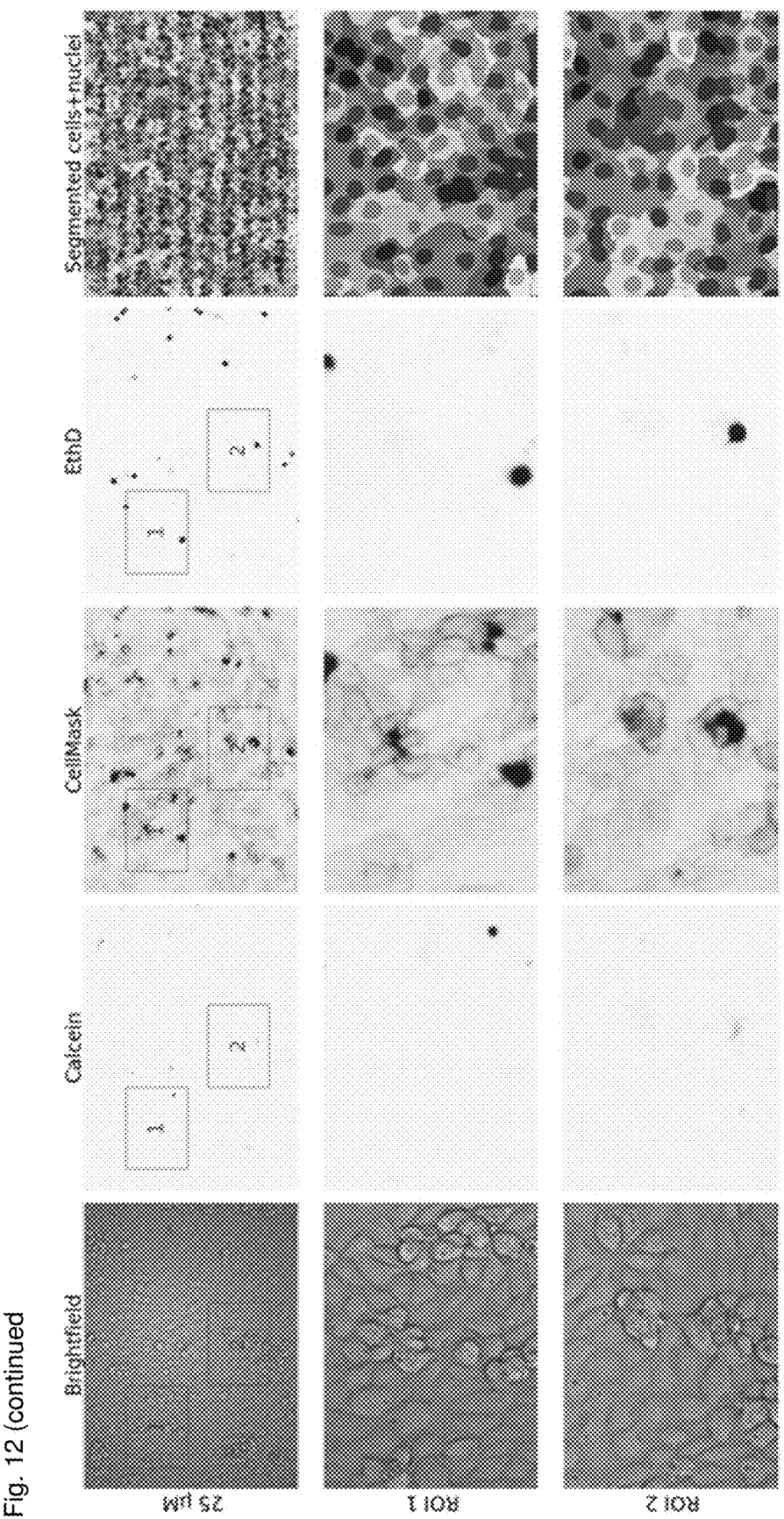
Figure 12:
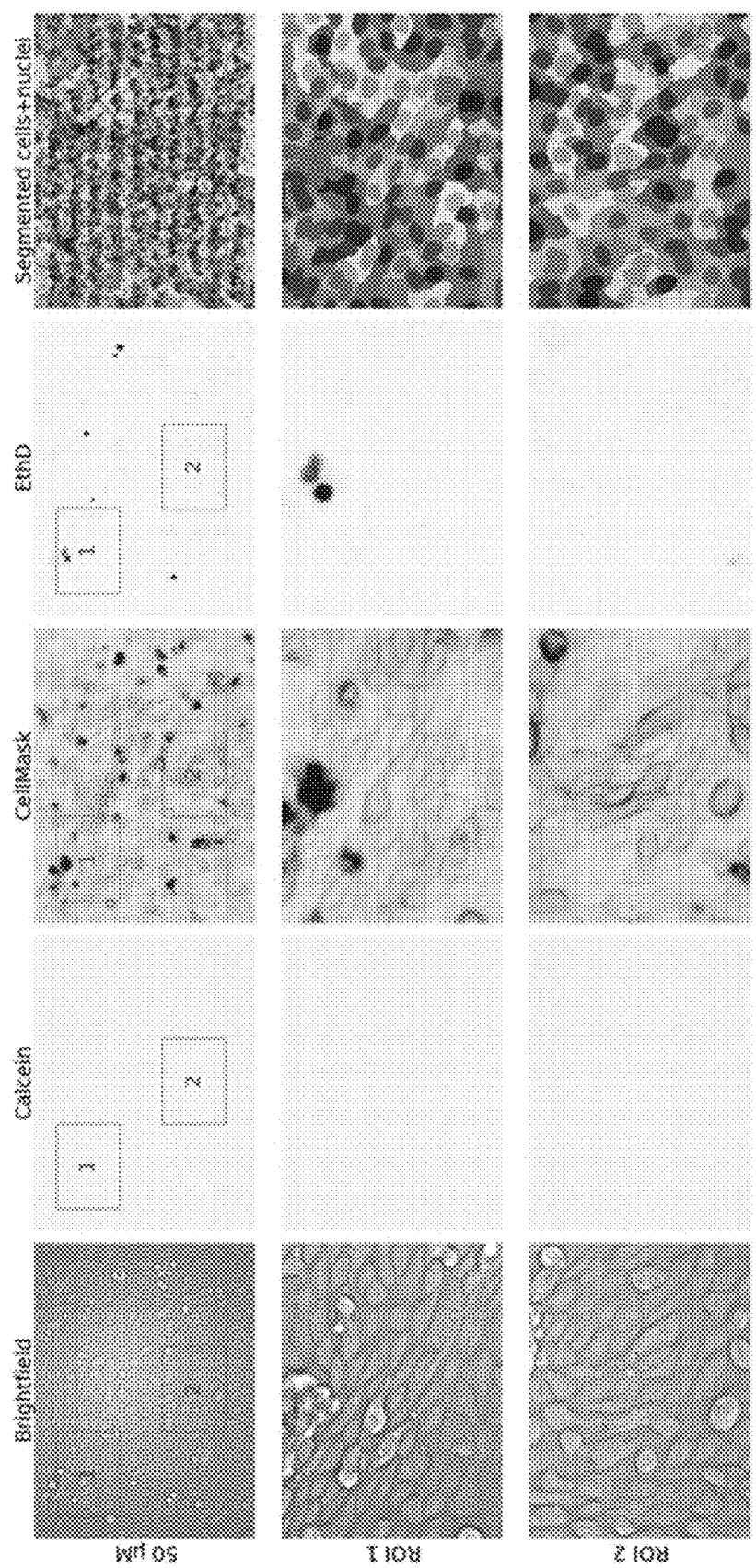
Figure 12:
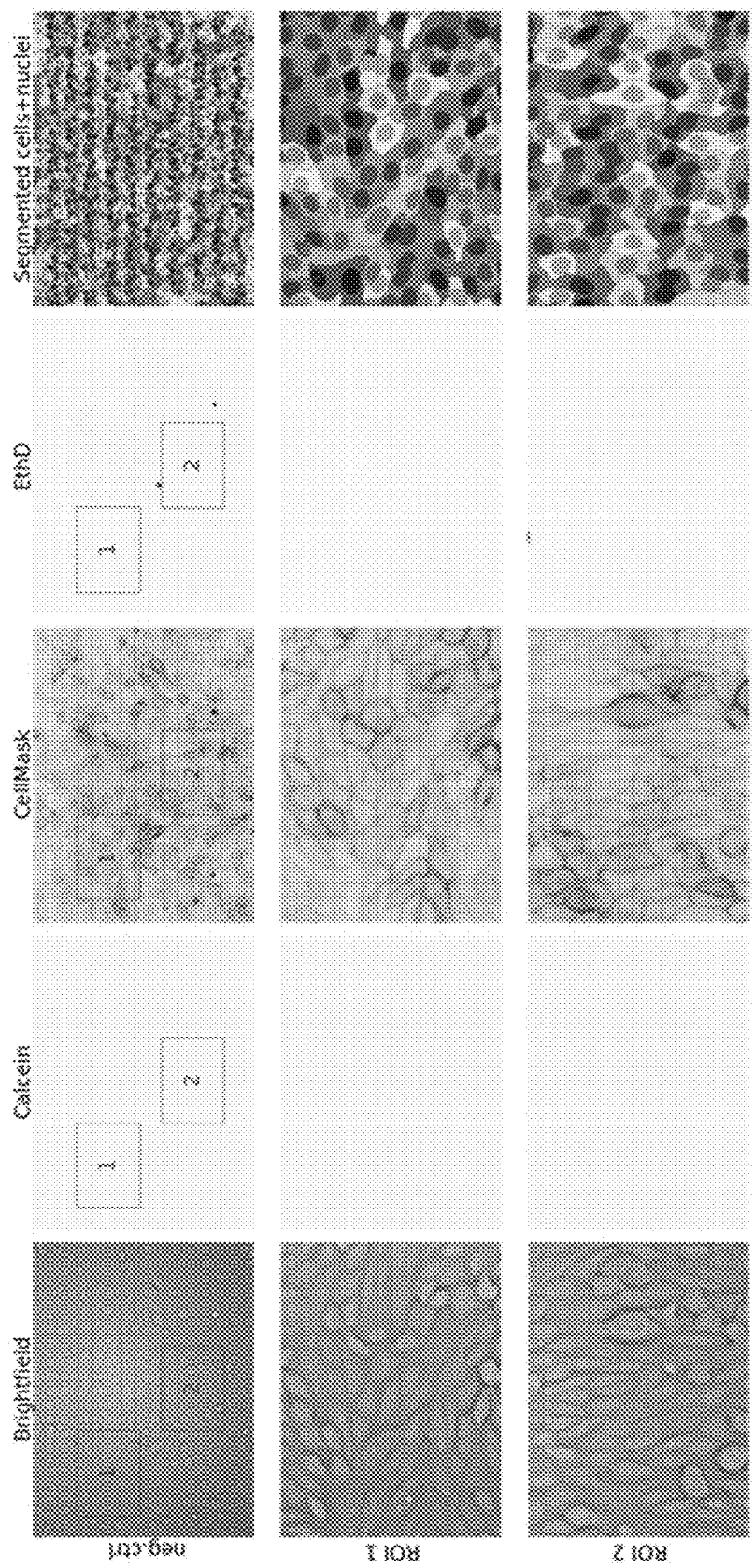

Cell medium spiked with 6 and 13 µM $(OEG_2)_2$-IP4 led to a reduction in total CaP area compared to the positive ctrl. It, however, still showed a high calcein staining intensity (FIG. 6C). Those results indicate that, in the positive ctrl, CaP is equally spread out across the monolayer, while with partial CaP inhibition large, localized cluster of high calcium content are formed (FIG. 6C, D, FIG. 12). The inventors assume that, as with intermediate Ca/P concentrations in the concentration range experiment, this reflects the general inhibition of CaP adhesion, except at areas of high cellular affinity for CaP. At those areas, a high accumulation of CaP is observed. As in the Ca/P concentration escalation experiments, these effects can be further supported by the SSIM of calcein and CellMask channel images. A high SSIM suggested areas of high intensity membrane stainings overlapping with high calcium regions (FIG. 6C). Additionally, the inventors observed an overlap of such areas with injured cells, as indicated by the EthD staining (FIG. 6B). Hence, such sites could present localized areas of cellular damage, and a regenerating/proliferating epithelium with surface expression of crystal binding proteins, which causes the high CaP accumulation. Increasing concentrations of $(OEG_2)_2$-IP4 from 6 to 13 µM first increased the correlation metric of the CellMask staining to levels above the positive ctrl, which can potentially be ascribed to a loss of cell outlines with no or limited presence of CaP-membrane clusters, before a reduction towards negative ctrl levels, wherein cells show round cellular outlines.

The inventors then tested the effects of the compound on CaP-induced CaOx crystallization. While the compound showed limited efficacy on CaOx crystallization in solution in a previous study (Kletzmayr, A. et al., *Adv. Sci.* 7, 1903337. DOI: 10.1002/advs.201903337, 2020), in the CaP-induced model, the inventors observed a dose-dependent change. Namely, $(OEG_2)_2$-IP4 could first, revert CaOx crystallization from calcium oxalate monohydrate (COM), the predominant most stable form, to calcium oxalate dihydrate (COD), in line with the inventors' former report of stepwise CaOx inhibition (Kletzmayr, A. et al., *Adv. Sci.* 7, 1903337. DOI: 10.1002/advs.201903337, 2020). Second, by further increasing concentrations to 100 µM COD was almost entirely abolished. Hence, $(OEG_2)_2$-IP4 reduced CaP-induced CaOx crystallization, which might be caused by coating and shielding of CaP deposits with compound.

Taken together, $(OEG_2)_2$-IP4 could prevent both CaP adhesion to the cellular monolayer and -associated cellular changes. The compound first confines CaP adhesion and cell injury to localized sites of adhesion, where CaP-membrane clusters are forming, before it completely prevents CaP deposition and cell injury at higher concentrations.

Example 5: Ca/P Induced Transcriptomic Changes Reflect Vascular Calcification Processes in Vitro and were Prevented by $(OEG2)_2$-IP4

Figure 7:
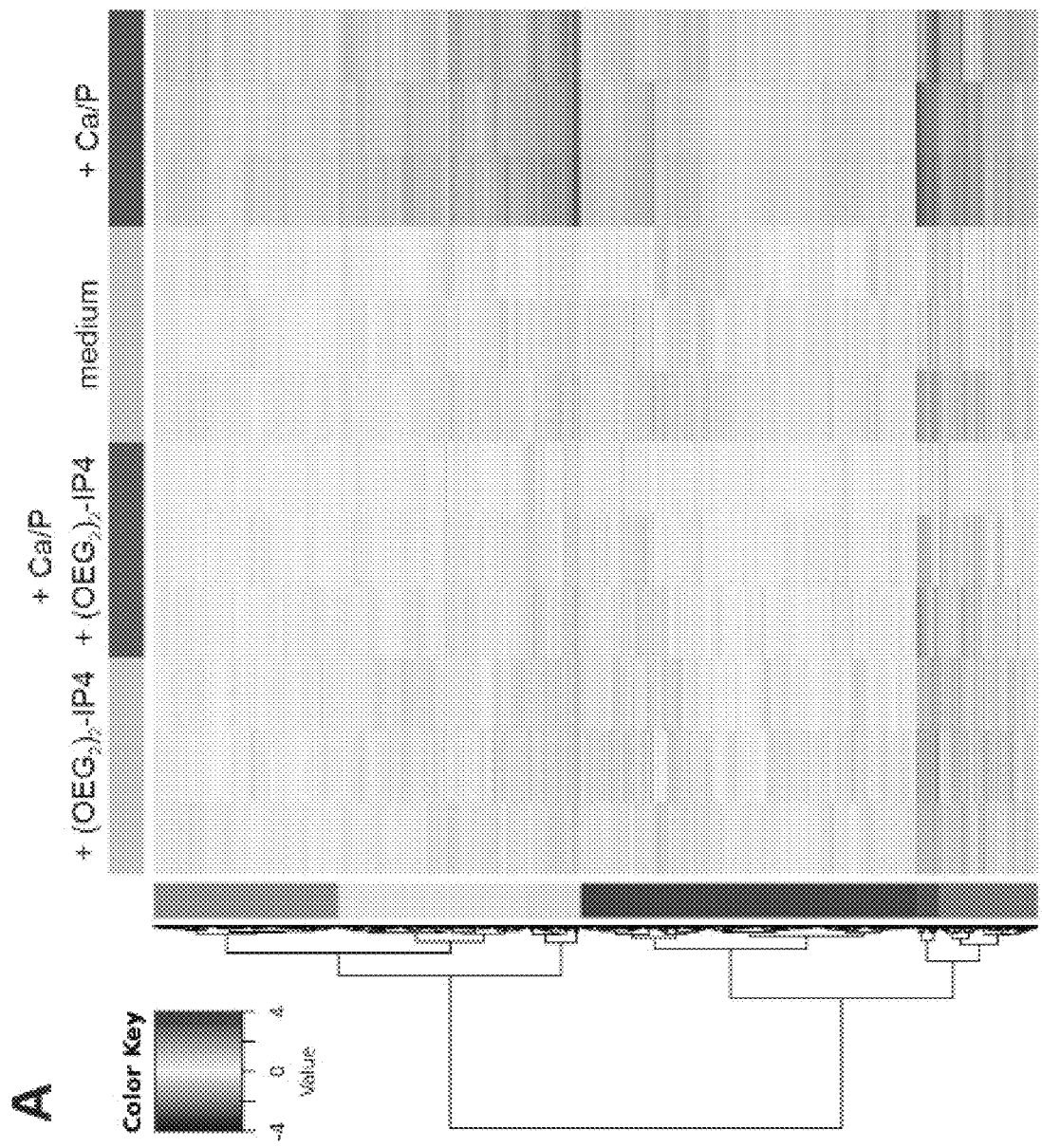
FIG. 7 shows Ca/P-induced transcriptomic changes of renal epithelial cells include inflammatory pathways, ECM proteins, cell proliferation and tissue homeostasis processes and are prevented by $(OEG_2)_2$-IP4 in vitro. A) Heatmap and hierarchical clustering of relative gene expression levels determined by RNA sequencing. Top 2000 differentially expressed genes between Ca/P vs. medium control with $p \le 0.01$ and log 2fold change 0.5, and respective expression levels in the other treatment groups are plotted (red-relatively upregulated, blue-relatively downregulated). B) Overrepresentation analysis of upregulated gene transcripts in the Ca/P vs. medium group. C) Overrepresentation analysis of downregulated gene transcripts in the Ca/P vs. medium group. Weighted set coverage of gene ontology terms and their respective enrichment score for differentially expressed genes in the Ca/P vs. medium control group is plotted (all FDR$\le 0.05$). D) Normalized count of gene transcripts (FPKM—fragments per kilobase of exon model per million reads mapped) involved in inflammatory responses, ECM composition, cell proliferation and tissue homeostasis of the different treatment groups is plotted (mean+SD, N=3).
Figure 7:
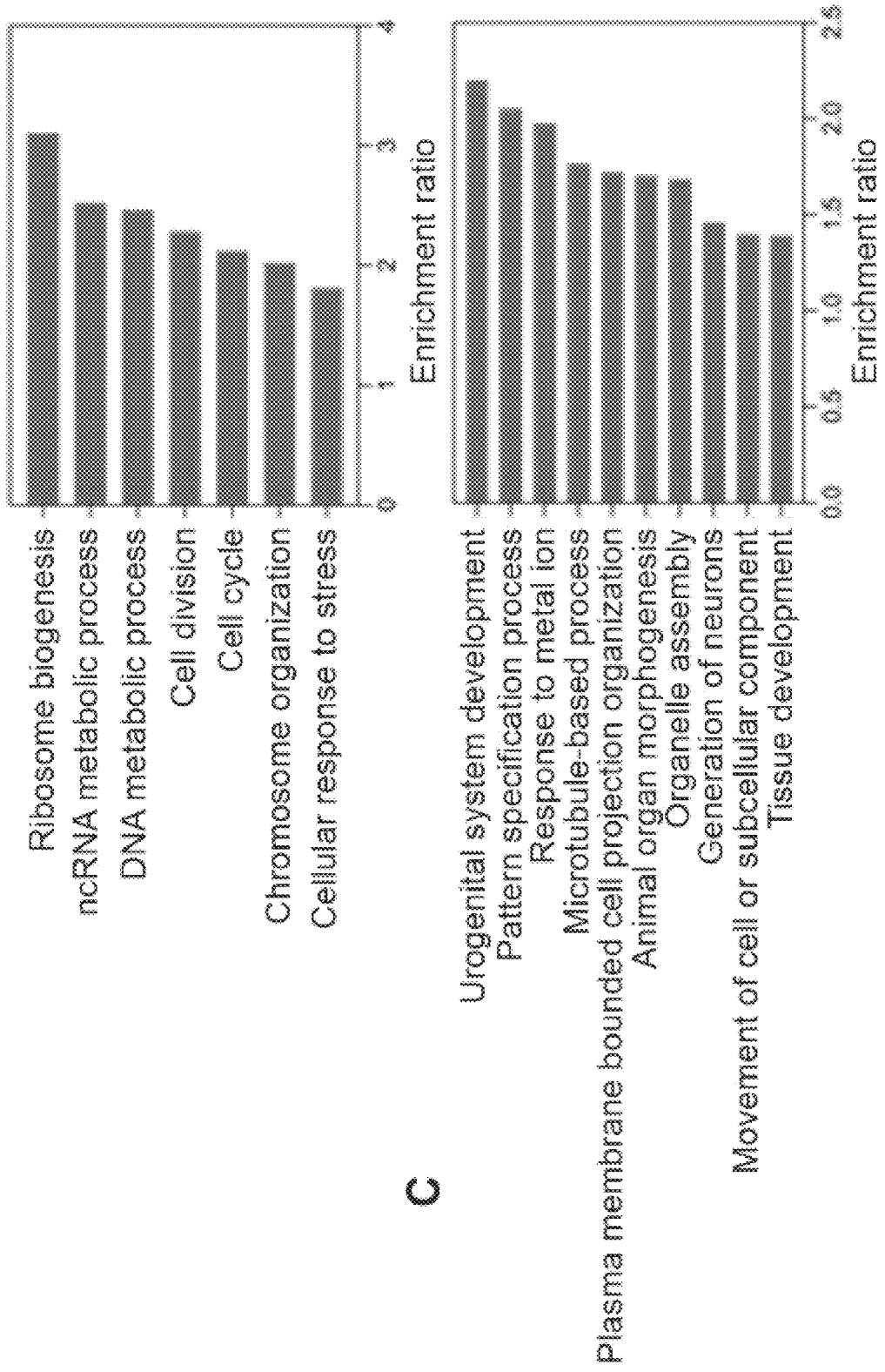
Figure 7:
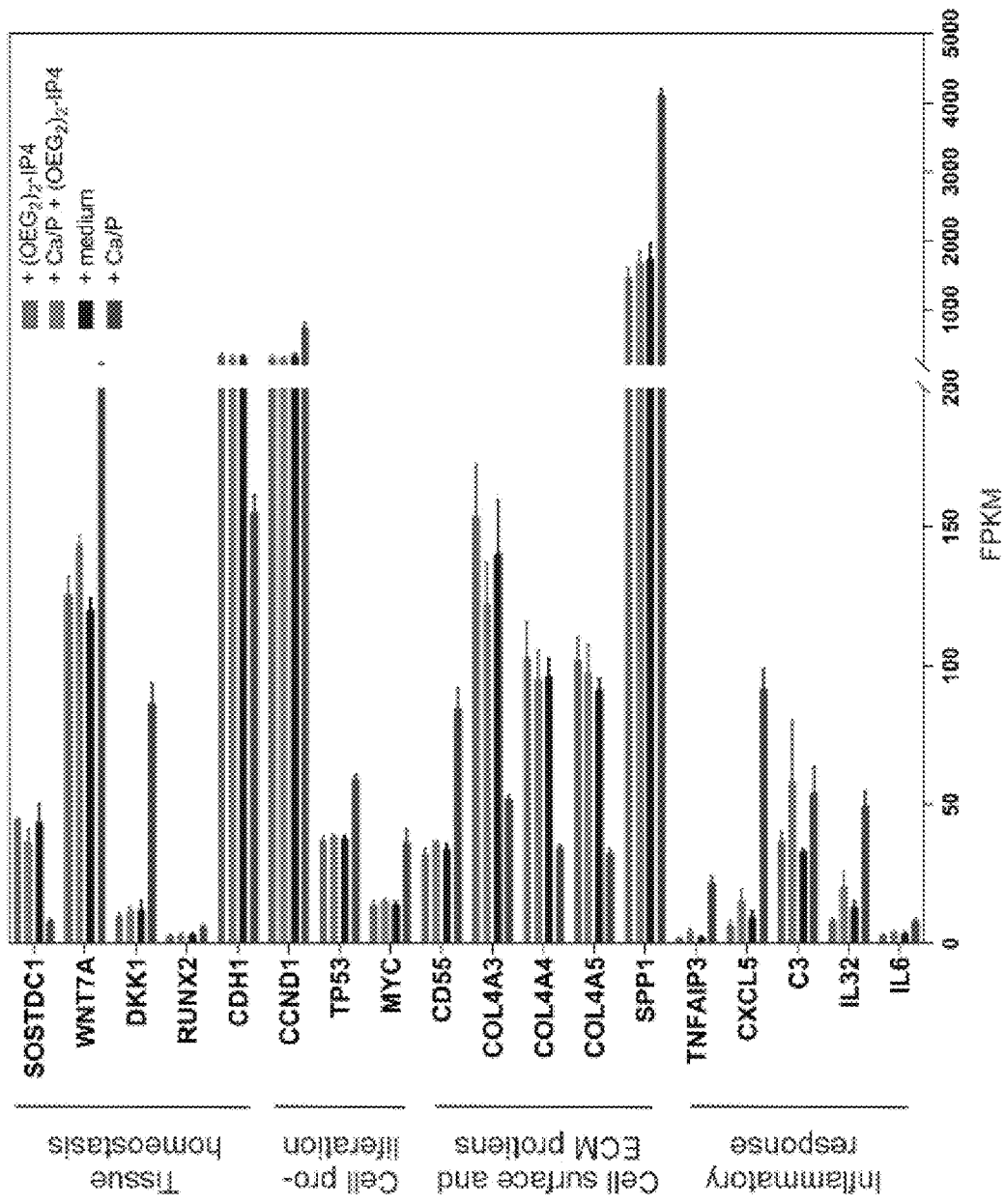

To further understand the cellular response to CaP and interpret the associated cellular morphology changes observed by imaging the inventors performed an RNA sequencing experiment. Cells were cultured as in the imaging assay and treated with Ca/P spiked medium (positive ctrl), Ca/P spiked medium premixed with 50 µM $(OEG_2)_2$-IP4, medium only (negative ctrl) or $(OEG_2)_2$-IP4 only. Hierarchical clustering of differentially expressed genes between positive and negative ctrl showed a drastic change in gene expression profile with Ca/P treatment, which was prevented by $(OEG_2)_2$-IP4 spiking (FIG. 7A). In positive ctrl vs. negative ctrl samples 2818 differentially expressed genes with a fold change ≥1.5 and p≤0.05 were detected, similar to Ca/P+$(OEG_2)_2$-IP4 and $(OEG_2)_2$-IP4 vs. positive ctrl samples (2437 and 2935 differentially expressed genes, respectively). In contrast, extremely limited numbers of differentially expressed genes were detected between Ca/P+$(OEG_2)_2$-IP4 vs. negative ctrl and vs. $(OEG_2)_2$-IP4 only (76 and 77, respectively). Thereby the drastic change induced by Ca/P treatment and the prevention thereof by $(OEG_2)_2$-IP4 was confirmed.

Overrepresentation analysis of upregulated genes in positive vs. negative ctrl samples revealed an enrichment in cell cycle, cell division and associated processes (DNA metabolic processes, ribosome biogenesis, chromosome organization), as well as cellular stress response processes (FIG. 7B). Downregulated genes enriched in structural and developmental processes (FIG. 7C).

The inventors next looked at single gene expression levels, focusing on four groups of genes, namely inflammatory response pathways, extracellular matrix (ECM) proteins, cell cycle and proliferation processes and genes involved in tissue homeostasis. Ca/P treatment of cells induced inflammatory response pathways, as reported previously for CaOx crystals (Kletzmayr, A. et al., Adv. Sci. 7, 1903337. DOI: 10.1002/advs.201903337, 2020). Upregulated genes included interleukin-6 (IL6) and interleukin-32 (IL32), complement C3 (C3), C-X-C motif chemokine ligands (e.g. CXCL5) and TNF signalling pathway genes, such as TNF alpha induced protein 3 (TNFAIP3) (FIG. 7D). Further extracellular matrix and cell surface genes were investigated. Putative calcium crystal binding proteins, such as the cell surface glycoproteins Osteopontin (SPP1) or CD55, were upregulated with Ca/P addition. In contrast, collagen IV family members (COL4A3, COL4A4, COL4A5) were downregulated. Collagen IV presents the major protein component of the tubular basement membrane. Hence, these data suggest strong alterations of the basement membrane, which might contribute to calcification of the basement membrane observed in kidney stone formers.

Overrepresentation analysis revealed a drastic deregulation of cell cycle and division processes. Upregulation of myc, a pro-proliferative gene, and cyclin D1 (CCND1), regulating the cell cycle in the G1/S transition, might indicate that renal epithelial cells enter a proliferative state upon Ca/P stimulation. This notion is further supported by the simultaneous upregulation of TP53, a regulator of DNA damage recognition and repair at the G1/S regulation point.

Furthermore, deregulation of genes involved in developmental processes and tissue homeostasis suggest changes in cellular differentiation upon Ca/P stimulation. Expression of e-cadherin (CDH1), an epithelial cell marker, was reduced upon Ca/P treatment, indicating a loss of the epithelial phenotype. The wnt signalling pathway was reported to promote osteogenic transdifferentiation of vascular cells and vascular calcification by directly modulating Runx2 gene expression. Expression of several wnt signalling pathway genes was deregulated upon Ca/P stimulation of renal epithelial cells, including Wnt family member 7A (WNT7A), sclerostin domain containing 1 (SOSTDC1) and dickkopf WNT signalling pathway inhibitor 1 (DKK1). Additionally, Runx2 expression was upregulated upon Ca/P treatment.

Therefore, RNA sequencing suggested drastic cellular alterations upon Ca/P stimulation, including a loss of the epithelial phenotype towards a more proliferative state and a change in cellular differentiation similar to vascular calcification processes. $(OEG_2)_2$-IP4 could largely prevent Ca/P induced changes, likely due to reduced cell-crystal interactions.

Example 6: $(OEG2)_2$-IP4 Reduces High Phosphate Induced Kidney Damage In Vivo

Figure 8:
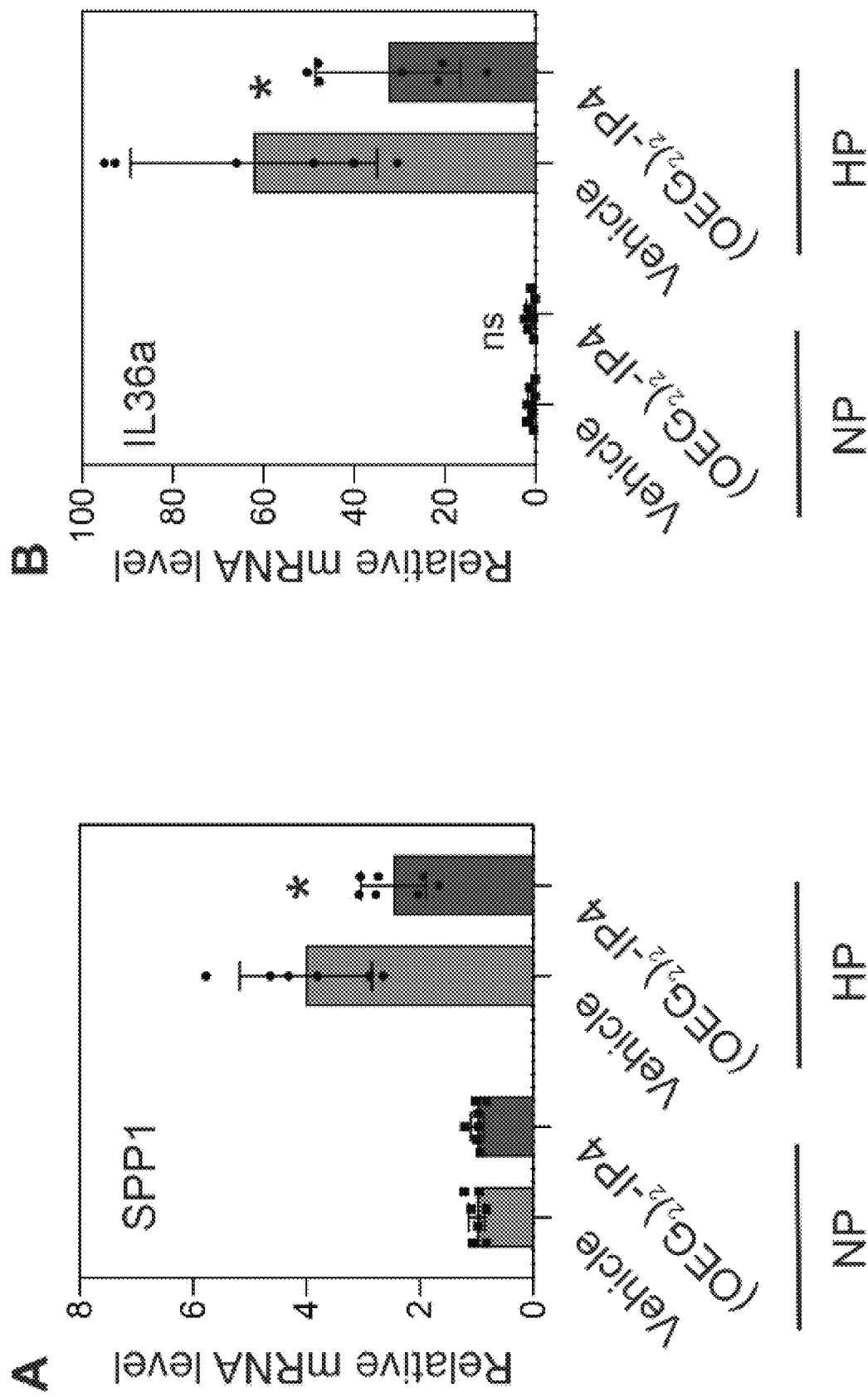
FIG. 8 shows $(OEG_2)_2$-IP4 reduces high phosphate induced kidney damage in vivo. C57BL/6 male were placed on either regular diet containing 0.35% inorganic phosphate (NP) or high phosphate diet containing 2.0% inorganic phosphate (HP). These mice were subcutaneously injected with either $(OEG_2)_2$-IP4 (100 mg/kg) or vehicle (distilled water) three times a week and then sacrificed at 20 weeks of age to harvest their blood and kidneys. Relative mRNA levels of (A) Spp1, (B) IL36a, (C) Ngal, (D) MMP3 and (E) Col1a1 in kidney tissue homogenate are shown (mean±SD, N=7, except HP vehicle group N=6, two-way ANOVA with Sidak's multiple comparison between $(OEG_2)_2$-IP4 vs. vehicle control within the respective diet group, ns—not significant, *p<0.05). (F) Collagen volume fraction following Picro-Sirius red staining of the kidneys (mean±SD, N=6, t-test between $(OEG_2)_2$-IP4 vs. vehicle, **p<0.01).
Figure 8:
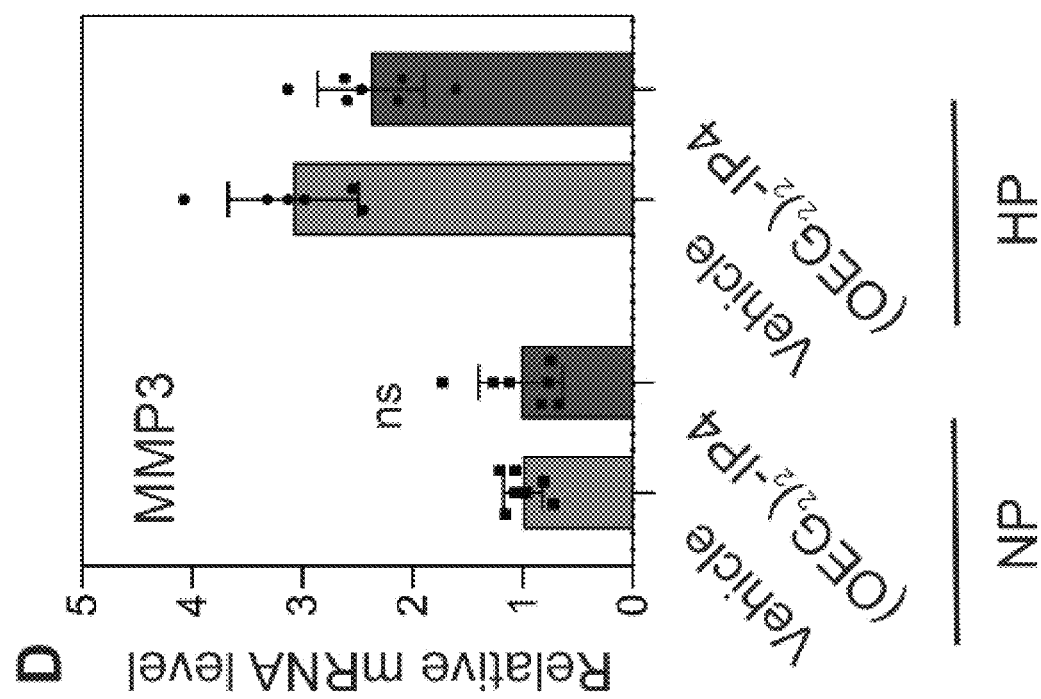
Figure 8:
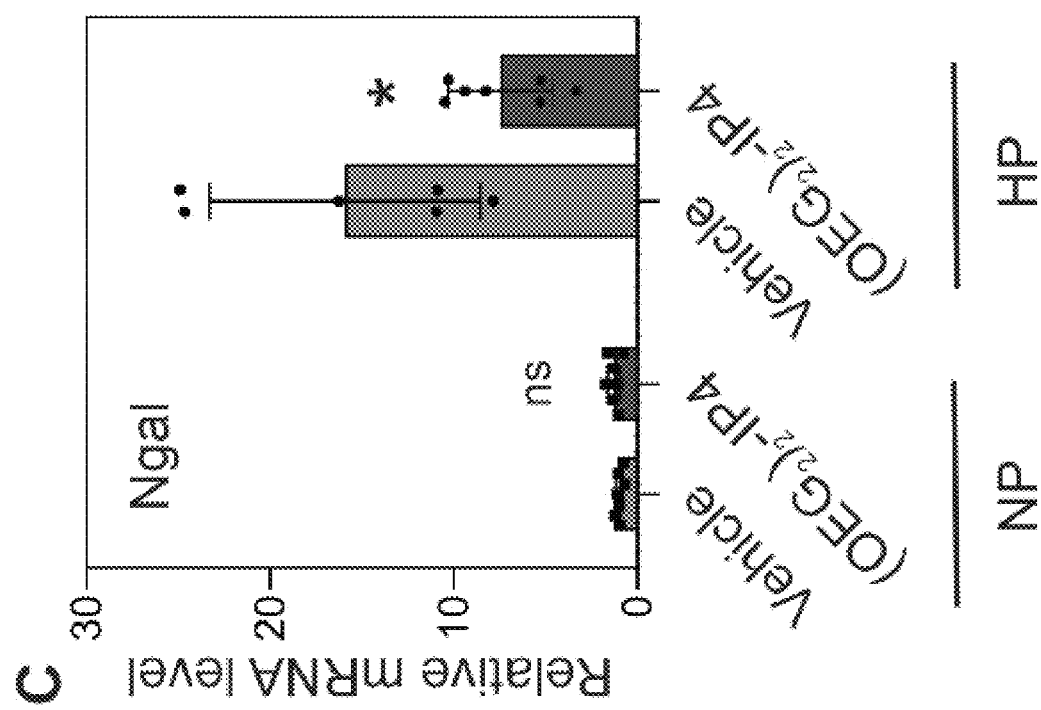
Figure 8:
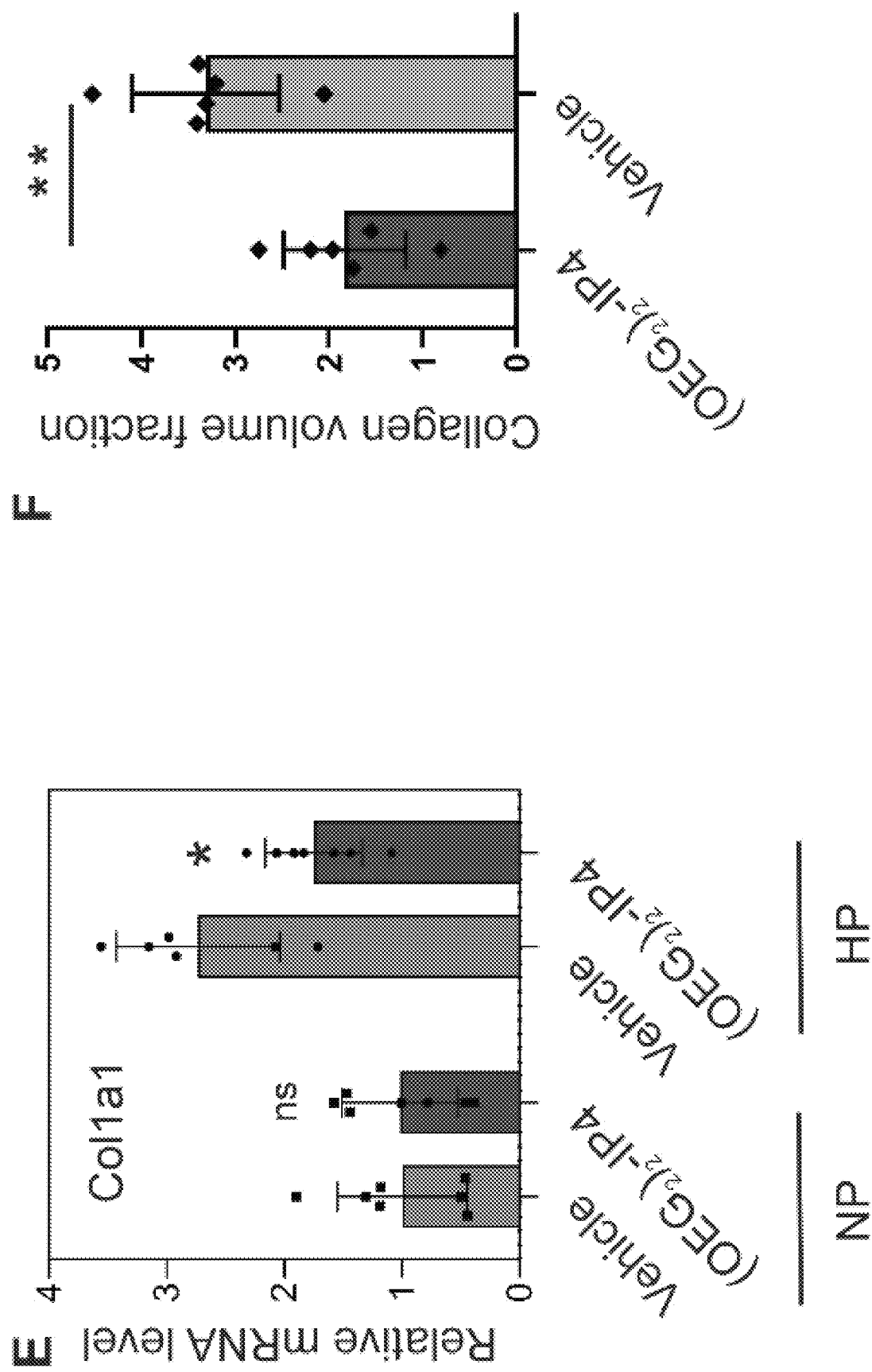
Figure 9:
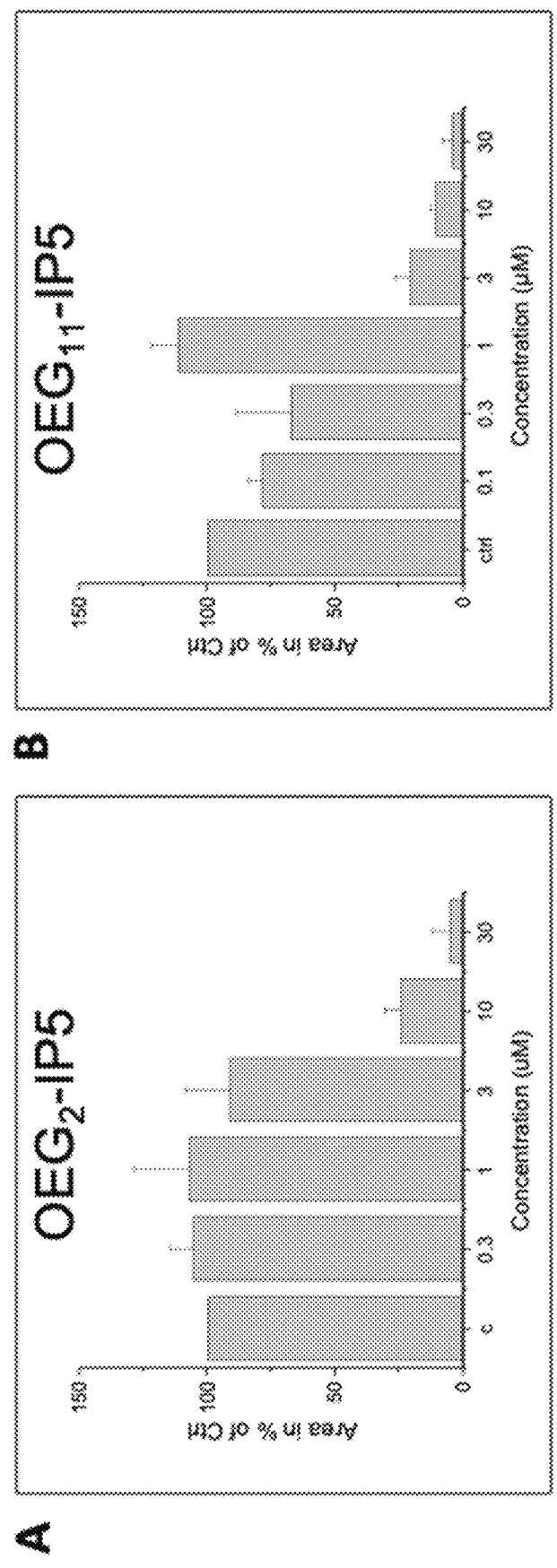
FIG. 9 shows inhibition of CaP precipitation with $OEG_2$-IP5, $OEG_{11}$-IP5, $(OEG_2)_2$-IP4, $(OEG_{11})_2$-IP4 and $OEG_B$-$(IP5)_2$. Effects of (A) $OEG_2$-IP5, (B) $OEG_{11}$-IP5, (C) $(OEG_2)_2$-IP4, (D) $(OEG_{11})_2$-IP4 and (E) $OEG_B$-$(IP5)_2$. on CaP precipitation in RTF spiked with 9 mM disodium phosphate and 8 mM calcium chloride were assessed by light microscopy followed by automated image analysis at t=4 h. Quantification of the total area covered with CaP precipitates/total area field of view (N=3, mean+SD, normalized to the control).
Figure 9:
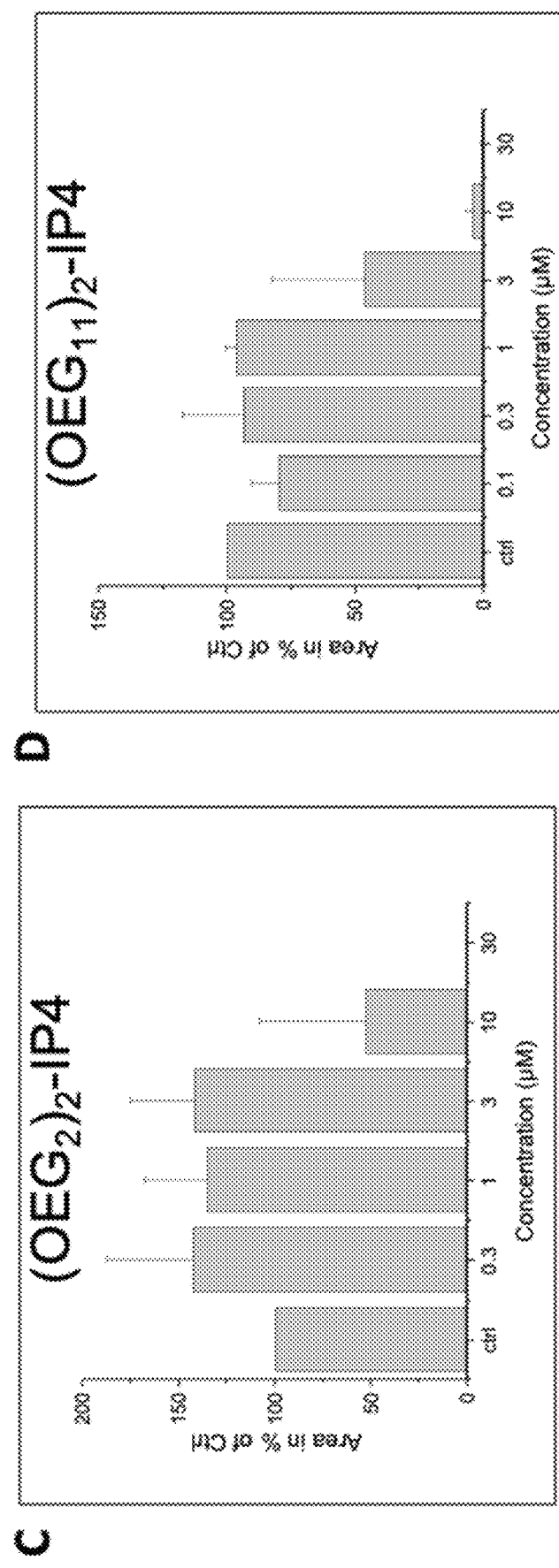
Figure 9:
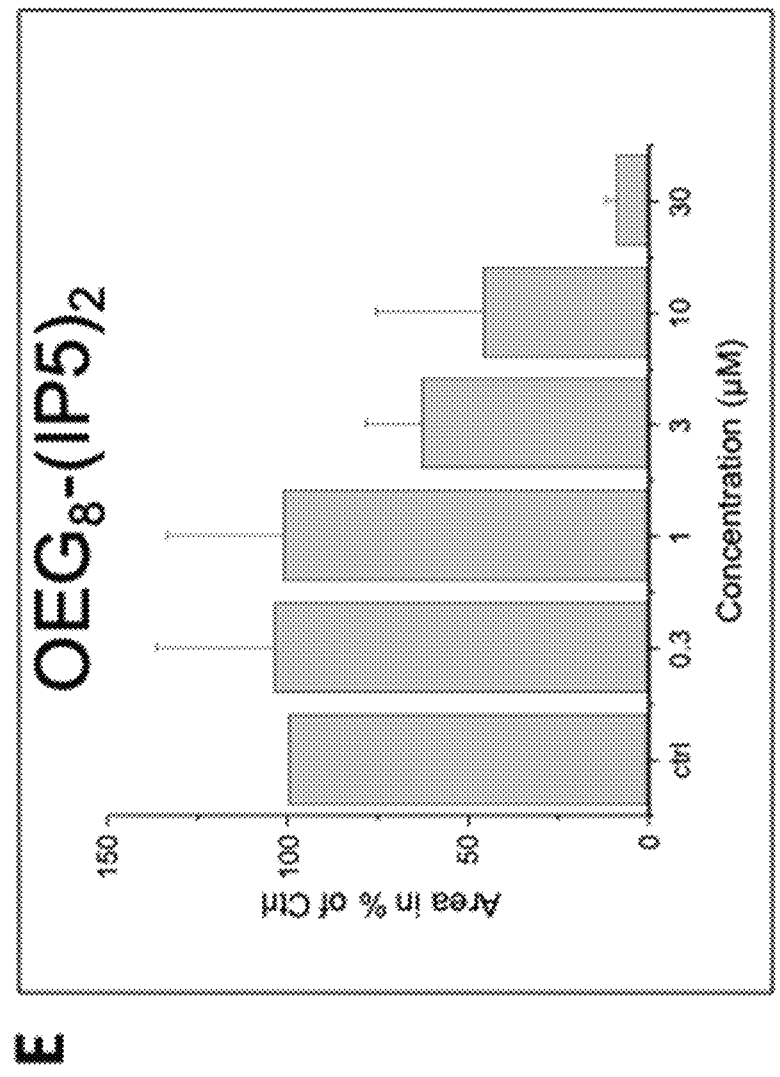

The efficacy of $(OEG_2)_2$-IP4 was further tested in a mouse model of high phosphate-induced kidney damage. Based on the previously performed characterization of $(OEG_2)_2$-IP4 pharmacokinetics in rats, a plasma concentration of roughly 80 µM after 30 min is anticipated in mice, following a subcutaneous injection of 100 mg/kg. The high phosphate diet induces FGF23 expression, compared to a normal phosphate diet, which in turn enhances renal phosphate excretion to keep serum levels within normal limits. This feedback mechanism is also suggested to contribute to high renal phosphate levels in early stage CKD. The phosphate diet induced an increase in urinary phosphate excretion from 1.9 to 35.6 mg/day, with no significant difference between the vehicle and treatment group (Table 2). Furthermore, no significant differences between the vehicle and treatment group were observed in serum phosphate, CaP or urine calcium at the end of the treatment period (Table 2). Mice on the high phosphate diet showed elevated markers of kidney damage, such as an increase in Spp1, IL-36a and Ngal (FIG. 8A-C). Further, heightened kidney expression levels of fibrosis markers, such as matrix metallopeptidase-3 (MMP) and Collagen 1α1 (Col1a1) were measured in the high phosphate vs. the normal phosphate vehicle control group. Concurrent treatment with 100 mg/kg $(OEG_2)_2$-IP4 3 times/week subcutaneously significantly reduced kidney damage and fibrosis markers compared to the vehicle control group in the high phosphate diet group (FIG. 8A-E). Furthermore, $(OEG_2)_2$-IP4 significantly reduces fibrosis, as measured by a reduced collagen volume fraction following Picro-Sirius red staining of the kidneys (FIG. 8F). Hence, the inventors' preliminary results suggest a beneficial effect of $(OEG_2)_2$-IP4 on phosphate-induced kidney injury in vivo.

DISCUSSION

Renal tubules are exposed to a wide variety of metabolites at high concentrations, sometimes causing their precipitation and cellular damage. Calcium precipitation in the form of CaP and CaOx is of particular concern, due to the associated kidney calcification, tissue damage and potentially accelerated progression of CKD. Because of the wide variety of nephrotoxic environmental perturbations, the inventors first aimed at establishing a simple in vitro image-based profiling tool that could allow the rapid testing of a multitude of renal perturbations, focusing on calcification conditions, and possible inhibitory molecules.

The proposed image-based calcification profiling platform allowed for simple and fast alterations of calcification conditions, i.e. ionic conditions triggering different types of calcium crystals. The inventors implemented an automated analysis pipeline, quantifying both single cell changes, as well as CaP deposition by fluorescent staining with calcein. Advantages of using an image-based profiling approach vs.

e.g. RNA sequencing of bulk cells, are the possibility to detect localized changes and its high-throughput adaptability.

The inventors demonstrated a gradual change in the feature profile of renal epithelial cell monolayers with increasing Ca/P concentration in the culture medium. A loss of the distinct cobblestone-like epithelial phenotype towards an enlarged cell shape was observed. In line, RNA sequencing confirmed a loss of the epithelial marker e-cadherin and a more proliferative state of cells stimulated with Ca/P. These findings are in agreement with literature reports suggesting dedifferentiation and cellular injury processes occur upon cell-crystal interactions. Signalling pathway alterations similar to pathological changes involved in vascular calcification, suggested a possible transdifferentiation of epithelial cells towards an osteoblast-like phenotype. Interestingly, the inventors also observed changes in CaP deposition patterns. Upon lowering Ca/P load, CaP precipitation and/or adhesion were favoured at sites of cell injury and high membrane staining. At those sites, CaP accumulated, causing further injury, cell detachment and formation of CaP-membrane clusters.

Previous studies support the idea of preferred attachment of CaP to specific crystal-binding proteins, which may be expressed mainly on dedifferentiated or regenerating renal epithelial cells. RNA sequencing confirmed an enhanced expression of crystal binding cell surface and ECM proteins, such as osteopontin. The enhanced proliferation of Ca/P stimulated cells might favour uncontrolled multi-layer growth and subsequent cell detachment, which could explain the derangements in cell membrane staining and contribute to the CaP cluster formation.

Additionally, collagen IV family members, the main components of the renal tubule basement membrane, were downregulated upon Ca/P stimulation. Calcification of the basement membrane is considered the first step of CaP plaque formation in kidney stone formers, however to date, the initial calcification process remains unclear. Hence collagen IV downregulation could provide a first insight into CaP plaque formation and suggests the utility of the calcification platform for mimicking pathophysiological processes. Further studies will be needed to clarify whether initial attachment sites are formed by the CaP load, or a certain extent of cell injury precedes and is then amplified by CaP binding. The results suggest the existence of active cellular involvement in the process of kidney calcification, thus supporting the profiling of a wide array of molecules, which could act on multiple steps of the process.

In a next step, the inventors investigated the efficacy of a library of IP6 analogues on effect on renal CaP precipitation in solution and cellular adhesion in vitro. The chosen lead compound $(OEG_2)_2$-IP4 dose-dependently reverted the cell feature profile towards the negative ctrl profile, inhibiting single cell changes, as well as CaP deposition. Protective effects of the compound on high Ca/P induced cellular changes were confirmed by RNA sequencing. This effect might be the result of both inhibition of CaP growth and CaP adhesion. Importantly, the protective effect of the compound translated to efficacy in a mouse model of high phosphate induced kidney damage. Hence, the inventors believe that, by inhibiting CaP precipitation and CaP-cell interactions, $(OEG_2)_2$-IP4 has the potential to prevent CaP-accelerated injury of the kidney. Additionally, the compound reduced CaP-induced CaOx crystallization on the cell monolayer in vitro. These results suggest a potential therapeutic benefit of the molecule in CaP-initiated kidney diseases.

We claim:

1. A method for treatment of a condition associated with formation of, and/or tissue exposure to, calcium salt crystals, comprising administering to a subject in need thereof a compound described by a general formula (I), or its pharmaceutically acceptable salt,

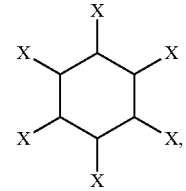

wherein
one or two or three X are oligo-ethylene glycol and the remaining X are $OPO_3^{2-}$
and wherein the condition is selected from the group consisting of
renal fibrosis, particularly when associated with calcification of renal tissue,
renal inflammation, particularly when associated with calcification of renal tissue,
nephritis,
interstitial nephritis,
glomerulonephritis,
phosphate-induced renal fibrosis,
phosphate-induced chronic kidney disease,
chronic kidney disease associated with hyperphosphatemia,
phosphate toxicity,
hyperphosphaturia,
hyperphosphatemia, and/or
hyper-FGF23-emia.

2. The method of claim 1, wherein two X are oligo-ethylene glycol and the remaining four X are $OPO_3^{2-}$.

3. The method of claim 1, wherein three X are oligo-ethylene glycol and the remaining three X are $OPO_3^{2-}$.

4. The method of claim 1, wherein one X is oligo-ethylene glycol and the remaining five X are $OPO_3^{2-}$.

5. The method of claim 1, wherein the oligo-ethylene glycol is described by a formula $O-(CH_2-CH_2-O)_nCH_3$, with n being selected from an integer between 2 and 20, particularly n being 2 to 12.

6. The method of claim 5, wherein n is 2.

7. The method of claim 2, wherein the compound is described by any one of the formulas:

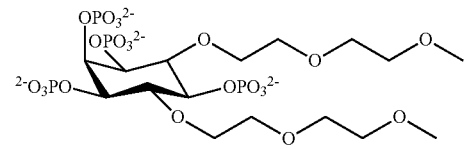

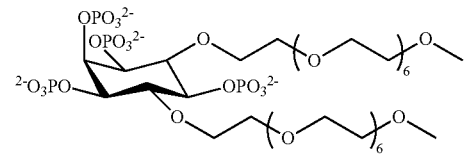

-continued

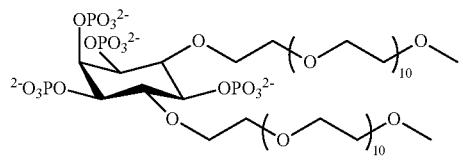
(Ic)

8. The method of claim 4, wherein the compound is described by any one of the formulas:

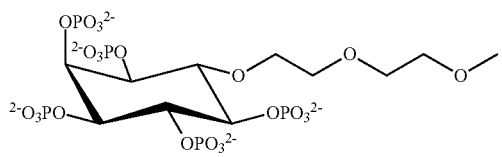
(I-d)

-continued

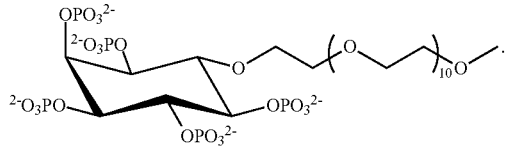
(I-e)

9. The method of claim 1, wherein the inositol moiety of formula (I) is myo-inositol.

10. The method of claim 1, wherein the condition associated is a condition associated with the formation of calcium phosphate salt or precipitate.

11. The method of claim 1, wherein the condition associated is a condition associated with the formation of calcium oxalate salt or precipitate.

12. The method of claim 1, wherein the condition associated is a condition associated with the formation of a mixed calcium phosphate oxalate precipitate.

* * * * *